US012715936B2

(12) United States Patent
Bogen et al.

(10) Patent No.: US 12,715,936 B2
(45) Date of Patent: Aug. 25, 2026

(54) HUMANIZED SINGLE-DOMAIN ANTIBODIES BINDING TO EPITOPE TAGS

(71) Applicant: NANO TAG BIOTECHNOLOGIES GMBH, Goettingen (DE)

(72) Inventors: Jan Patrick Bogen, Mainz (DE); Joycelyn Wüstehube-Lausch, Mainz (DE); Hans-Ulrich Schmoldt, Mainz (DE)

(73) Assignee: NANO TAG BIOTECHNOLOGIES GMBH, Goettingen (DE)

( * ) Notice: Subject to any disclaimer, the term of this patent is extended or adjusted under 35 U.S.C. 154(b) by 0 days.

(21) Appl. No.: 19/312,137

(22) Filed: Aug. 27, 2025

(65) Prior Publication Data

US 2026/0008872 A1 Jan. 8, 2026

Related U.S. Application Data

(63) Continuation of application No. PCT/EP2024/078372, filed on Oct. 9, 2024.

(30) Foreign Application Priority Data

Oct. 10, 2023 (EP) .................................... 23202684

(51) Int. Cl.
*C07K 16/44* (2006.01)

(52) U.S. Cl.
CPC .......... *C07K 16/44* (2013.01); *C07K 2317/24* (2013.01); *C07K 2317/569* (2013.01); *C07K 2317/92* (2013.01)

(58) Field of Classification Search
None
See application file for complete search history.

(56) References Cited

U.S. PATENT DOCUMENTS

2023/0093123 A1 3/2023 Wu et al.

FOREIGN PATENT DOCUMENTS

WO 94/04678 A1 3/1994
WO 2020/053239 A1 3/2020

OTHER PUBLICATIONS

Gotzke et al. The ALFA-tag is a highly versatile tool for nanobody-based bioscience applications. Nature Communications (doi.org/10.1038/s41467-019-12301-7), 2019.*

Wang et al. ALFA nanobody-guided endogenous labeling. Nature Chemical Biology 21: 1992-2001, 2025.*

Carter et al., "Humanization of an anti-p185HER2 antibody for human cancer therapy", Proc Natl Acad Sci U S A. May 15, 1992;89(10):4285-9. doi: 10.1073/pnas.89.10.4285.

Chothia et al., "Structural repertoire of the human VH segments", J Mol Biol. Oct. 5, 1992;227(3):799-817. doi: 10.1016/0022-2836(92)90224-8.

Co et al., "Chimeric and humanized antibodies with specificity for the CD33 antigen", J Immunol. Feb. 15, 1992;148(4):1149-54.

Co et al., "Humanized antibodies for antiviral therapy", Proc Natl Acad Sci U S A. Apr. 1, 1991;88(7):2869-73. doi: 10.1073/pnas.88.7.2869.

Dondelinger et al., 'Understanding the Significance and Implications of Antibody Numbering and Antigen-Binding Surface/Residue Definition', 2018; doi: 10.3389/fimmu.2018.02278.

Fernández-Quintero et al., "Antibody humanization-the Influence of the antibody framework on the CDR-H3 loop ensemble in solution", Protein Eng Des Sel. Dec. 31, 2019;32(9):411-422. doi: 10.1093/protein/gzaa004.

Gorman et al., "Reshaping a therapeutic CD4 antibody", Proc Natl Acad Sci U S A. May 15, 1991;88(10):4181-5. doi: 10.1073/pnas.88.10.4181.

Götzke et al., "The ALFA-tag is a highly versatile tool for nanobody-based bioscience applications", Nat Commun. Sep. 27, 2019;10(1):4403. doi: 10.1038/s41467-019-12301-7.

Kettleborough et al., "Humanization of a mouse monoclonal antibody by CDR-grafting: the importance of framework residues on loop conformation", Protein Eng. Oct. 1991;4(7):773-83. doi: 10.1093/protein/4.7.773.

Laver et al., "Epitopes on protein antigens: misconceptions and realities", Cell. May 18, 1990;61(4):553-6. doi: 10.1016/0092-8674(90)90464-p.

Maass et al., "Alpaca (*Lama pacos*) as a convenient source of recombinant camelid heavy chain antibodies (VHHs)", J Immunol Methods. Jul. 31, 2007;324(1-2):13-25. doi: 10.1016/j.jim.2007.04.008. Epub May 15, 2007.

Maeda et al., "Construction of reshaped human antibodies with HIV-neutralizing activity", Hum Antibodies Hybridomas. Jul. 1991;2(3):124-34.

Mitwasi et al., ""UniCAR"-modified off-the-shelf NK-92 cells for targeting of GD2-expressing tumour cells", Sci Rep. Feb. 7, 2020;10(1):2141. doi: 10.1038/s41598-020-59082-4.

Reiter et al., "Stabilization of the Fv fragments in recombinant immunotoxins by disulfide bonds engineered into conserved framework regions", Biochemistry. May 10, 1994;33(18):5451-9. doi: 10.1021/bi00184a014.

Riechmann et al., "Reshaping human antibodies for therapy", Nature. Mar. 24, 1988;332(6162):323-7. doi: 10.1038/332323a0.

Sato et al., "Reshaping a human antibody to inhibit the interleukin 6-dependent tumor cell growth", Cancer Res. Feb. 15, 1993;53(4):851-6.

Sela, M., "Antigenicity: some molecular aspects", Science. Dec. 12, 1969;166(3911):1365-74. doi: 10.1126/science.166.3911.1365.

(Continued)

*Primary Examiner* — Christine J Saoud
(74) *Attorney, Agent, or Firm* — Michael A. Whittaker

(57) ABSTRACT

The present invention provides humanized versions of single-domain antibodies specifically binding the epitope tag of SRLEEELRRRLTE (SEQ ID NO: 2), which can be used for binding, detection, immobilization, isolation or purification a protein comprising the said epitope tag. Furthermore, the present invention relates to a nucleic acid encoding the humanized antibody and a vector comprising the nucleic acid, as well as a host cell comprising the nucleic acid or the vector described herein.

17 Claims, 5 Drawing Sheets

Specification includes a Sequence Listing.

(56) References Cited

OTHER PUBLICATIONS

Tempest et al., "Reshaping a human monoclonal antibody to inhibit human respiratory syncytial virus infection in vivo", Biotechnology (N Y). Mar. 1991;9(3):266-71. doi: 10.1038/nbt0391-266.
Tomlinson et al., "The structural repertoire of the human V kappa domain", EMBO J. Sep. 15, 1995;14(18):4628-38. doi: 10.1002/j.1460-2075.1995.tb00142.x.
Verhoeyen et al., "Reshaping human antibodies: grafting an antilysozyme activity", Science. Mar. 25, 1988;239(4847):1534-6. doi: 10.1126/science.2451287.
Wilkinson et al., "Systematic analysis of the varied designs of 819 therapeutic antibodies and Fc fusion proteins assigned international nonproprietary names", MAbs. Jan.-Dec. 2022;14(1):2123299. doi: 10.1080/19420862.2022.2123299.

* cited by examiner

HUMANIZED SINGLE-DOMAIN ANTIBODIES BINDING TO EPITOPE TAGS

CROSS-REFERENCE TO RELATED APPLICATIONS

The present invention is a continuation of International Application No. PCT/EP2024/078372, filed Oct. 9, 2024, which claims the right of priority of European Patent Application No. 23202684.9 filed Oct. 10, 2023. The entire disclosures of the above-identified priority applications are hereby fully incorporated herein by reference.

SEQUENCE LISTING

The instant application contains a Sequence Listing which has been submitted electronically in .XML format and is hereby incorporated by reference in its entirety. Said .XML copy, created on Aug. 15, 2025, is named "SCH-44000-TR1_SeqListing.xml" and is 124,259 bytes in size. The sequence listing contained in this .XML file is part of the specification and is hereby incorporated by reference herein in its entirety.

FIELD OF THE INVENTION

The present invention provides a humanized version of single-domain antibodies specifically binding the epitope tag of SRLEEELRRRLTE (SEQ ID NO: 2), which can be used for binding, detection, immobilization, isolation or purification a protein comprising the said epitope tag. Furthermore, the present invention relates to a nucleic acid encoding the humanized antibody and a vector comprising the nucleic acid, as well as a host cell comprising the nucleic acid or the vector described herein.

BACKGROUND

In 2019, Götzke et al. published the article '*The ALFA-tag is a highly versatile tool for nanobody-based bioscience applications*' (Götzke et al., Nat Commun. 2019 Sep. 27; 10(1): 4403. doi: 10.1038/s41467-019-12301-7). The ALFA®-tag is a rationally designed peptide with a unique sequence that forms a stable alpha helix in solution, is electroneutral and highly soluble at physiological conditions. It can be fused to a binding partner in different orientations (N- or C-terminal or in between two domains of a fusion protein) without loss of structure and function and can be detected with a high affinity (double-digit pM Kd) single-domain antibody (VHH) that the authors have identified from an immunized alpaca via a selection method based on the isolation of target specific B-cells (CELLINE). A detailed description of the ALFA®/NbALFA epitope tag system can be found in the PCT patent publication WO 2020/053239 A1. Thus, the ALFA®-tag and the NbALFA single-domain antibody specific for the tag have a great potential in bioscience applications.

NbALFA is derived from immunized alpaca and alpaca-derived single-domain antibodies (VHHs) in general share a low degree of homology to human sequences. However, for in vivo applications of the ALFA®/NbALFA tool in humans, higher sequence homology to human counterpart sequence would be desirable.

SUMMARY OF THE INVENTION

The present invention relates to a single-domain antibody that specifically binds to an epitope tag comprising the sequence SRLEEELRRRLTE (SEQ ID NO: 2), wherein the antibody comprises the CDR1 sequence as shown in SEQ ID NO: 94, the CDR2 sequence as shown in SEQ ID NO: 97, and the CDR3 sequence as shown in SEQ ID NO: 98, and wherein the antibody further comprises at positions corresponding to sequence position 47, 48, and 50 of SEQ ID NO: 1 the following amino acid residues: Arg at position 47, Arg at position 48, Met at position 50, and wherein the antibody comprises a sequence having at least 90% sequence identity to any one of SEQ ID NOs: 118-125.

The present invention also relates to a protein comprising the amino acid sequence of the antibody of the invention.

The present invention also relates to a complex comprising a protein comprising the amino acid sequence of X1-X2-L-E-X5-E-X7-R-R-R-L-X12-X13 (SEQ ID NO: 3), wherein X1 is G or S or P or T, X2 is R or G or P, X5 is E or Q, X7 is L or I, X12 is S or T or P or A or D or E, and wherein X13 is P or A or S or K or D or E or no amino acid; and an antibody of the invention.

The present invention also relates to a nucleic acid encoding an antibody of the invention.

The present invention also relates to a vector comprising the nucleic acid of the invention.

The present invention also relates to a host cell comprising the nucleic acid of the invention or the vector of the invention or expressing the antibody of the invention.

The present invention also relates to use of the antibody of the invention for the binding, detection, immobilization, isolation, or purification of a protein comprising the amino acid sequence of X1-X2-L-E-X5-E-X7-R-R-R-L-X12-X13 (SEQ ID NO: 3), wherein X1 is G or S or P or T, X2 is R or G or P, X5 is E or Q, X7 is L or I, X12 is S or Tor P or A or D or E, and wherein X13 is P or A or S or K or D or E or no amino acid.

The present invention also relates to a method of binding or detecting a protein comprising the amino acid sequence of X1-X2-L-E-X5-E-X7-R-R-R-L-X12-X13 (SEQ ID NO: 3), wherein X1 is G or S or P or T, X2 is R or G or P, X5 is E or Q, X7 is L or I, X12 is S or T or P or A or D or E, and wherein X13 is P or A or S or K or D or E or no amino acid, comprising contacting the protein with an antibody of the invention and optionally detecting the antibody or a label comprised in the antibody.

The present invention also relates to a method of producing the antibody of the invention comprising cultivating the host cell of the invention under conditions allowing the expression of the antibody.

Figure 1:
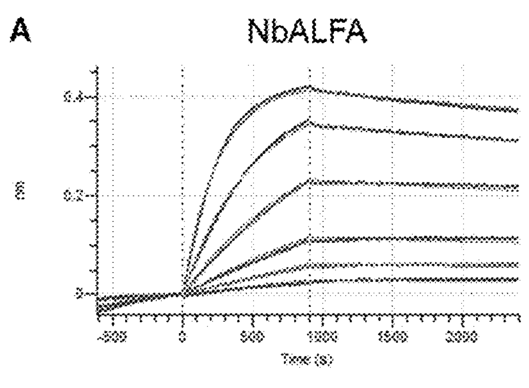
FIG. 1: Affinity of humanized NbALFA variants generated by CDR grafting. A, affinity measurements of the original alpaca-derived NbALFA (wtNbALFA) for the peptide of SEQ ID NO: 2. B, affinity measurements of variant 3 for the peptide of SEQ ID NO: 2. C, affinity measurements of variant 4 for the peptide of SEQ ID NO: 2. D, affinity measurements of variant 5 for the peptide of SEQ ID NO: 2. E, affinity measurements of variant 6 for the peptide of SEQ ID NO: 2. F, affinity measurements of variant 7 for the peptide of SEQ ID NO: 2. Affinity was determined using biolayer interferometry as described in Method 1 of the Examples.
Figure 1:
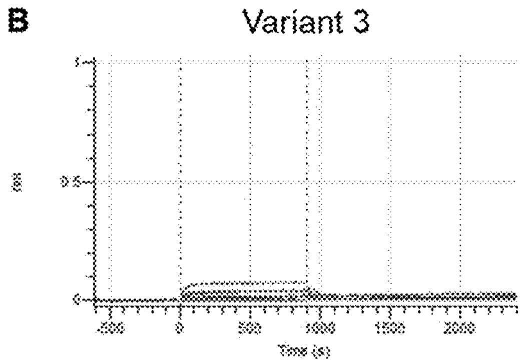
Figure 1:
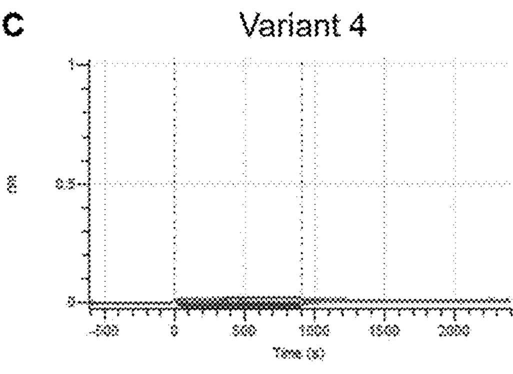
Figure 1:
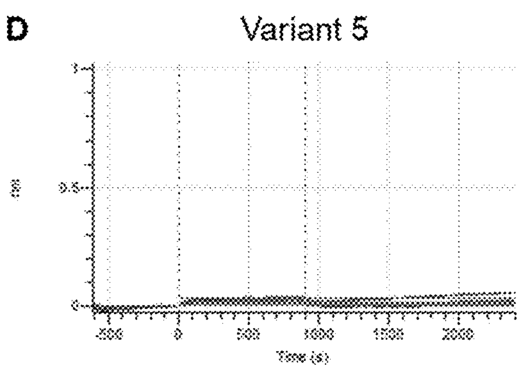
Figure 1:
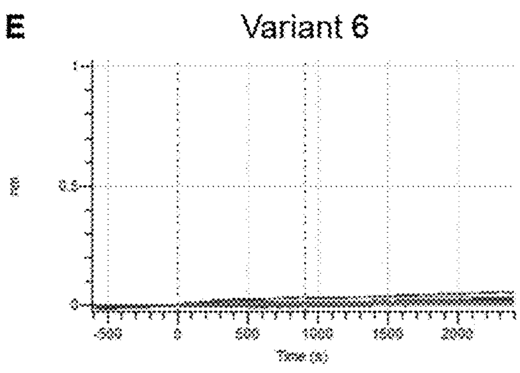
Figure 1:
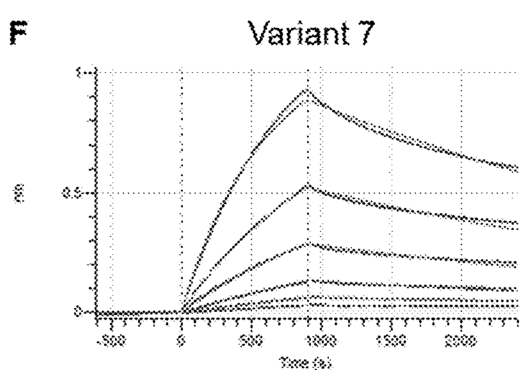
Figure 2:
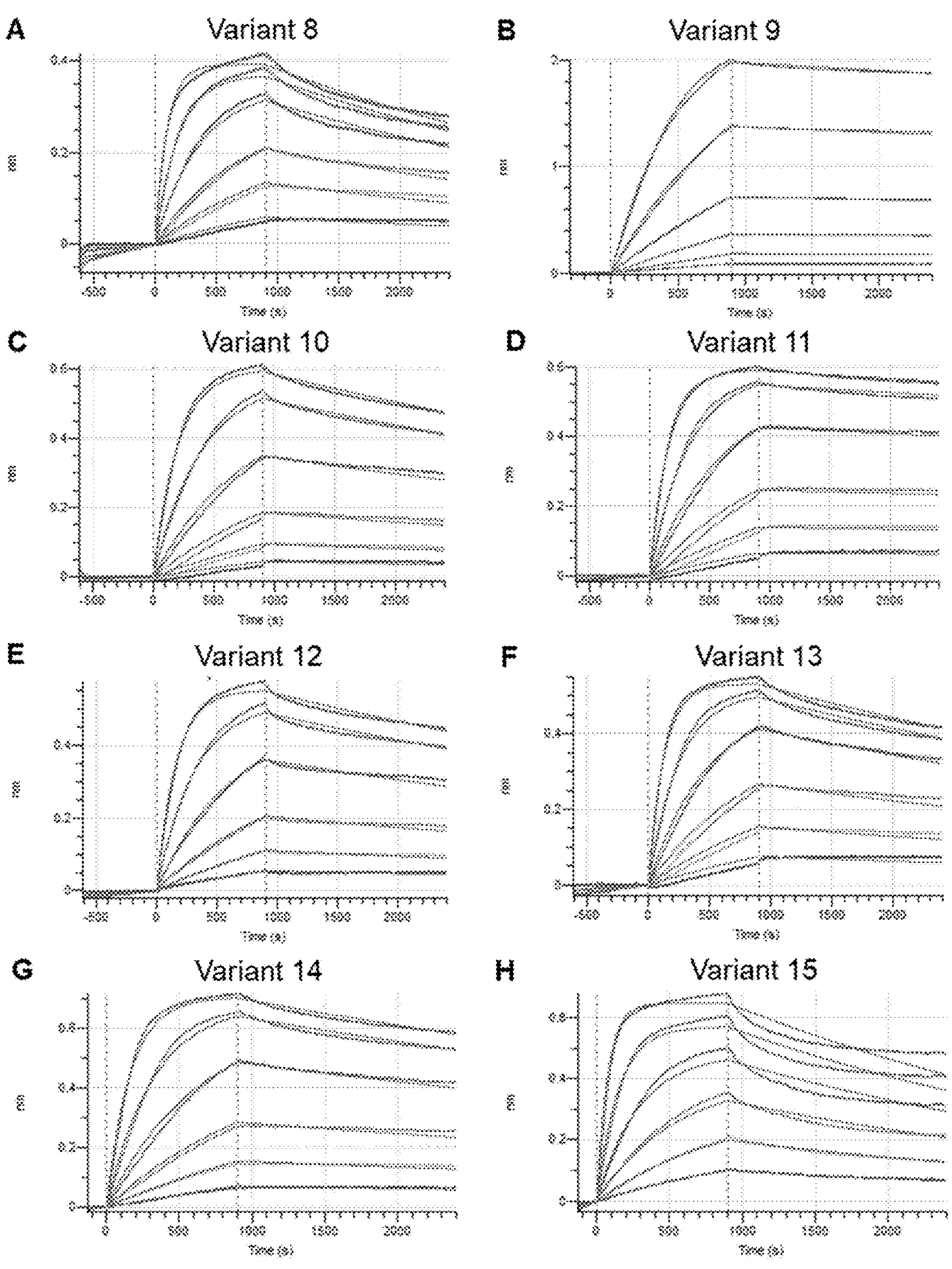
FIG. 2: Affinity of further engineered humanized NbALFA variants. A, affinity measurements of variant 8 for the Peptide of SEQ ID NO: 2. B, affinity measurements of variant 9 for the peptide of SEQ ID NO: 2. C, affinity measurements of variant 10 for the peptide of SEQ ID NO.

2. D, affinity measurements of variant 11 for the peptide of SEQ ID NO: 2. E, affinity measurements of variant 12 for the peptide of SEQ ID NO: 2. F, affinity measurements of variant 13 for the peptide of SEQ ID NO: 2. G, affinity measurements of variant 14 for the peptide of SEQ ID NO: 2. H, affinity measurements of variant 15 for the peptide of SEQ ID NO: 2. Affinity was determined using biolayer interferometry as described in Method 1 of the Examples.

Figure 3:
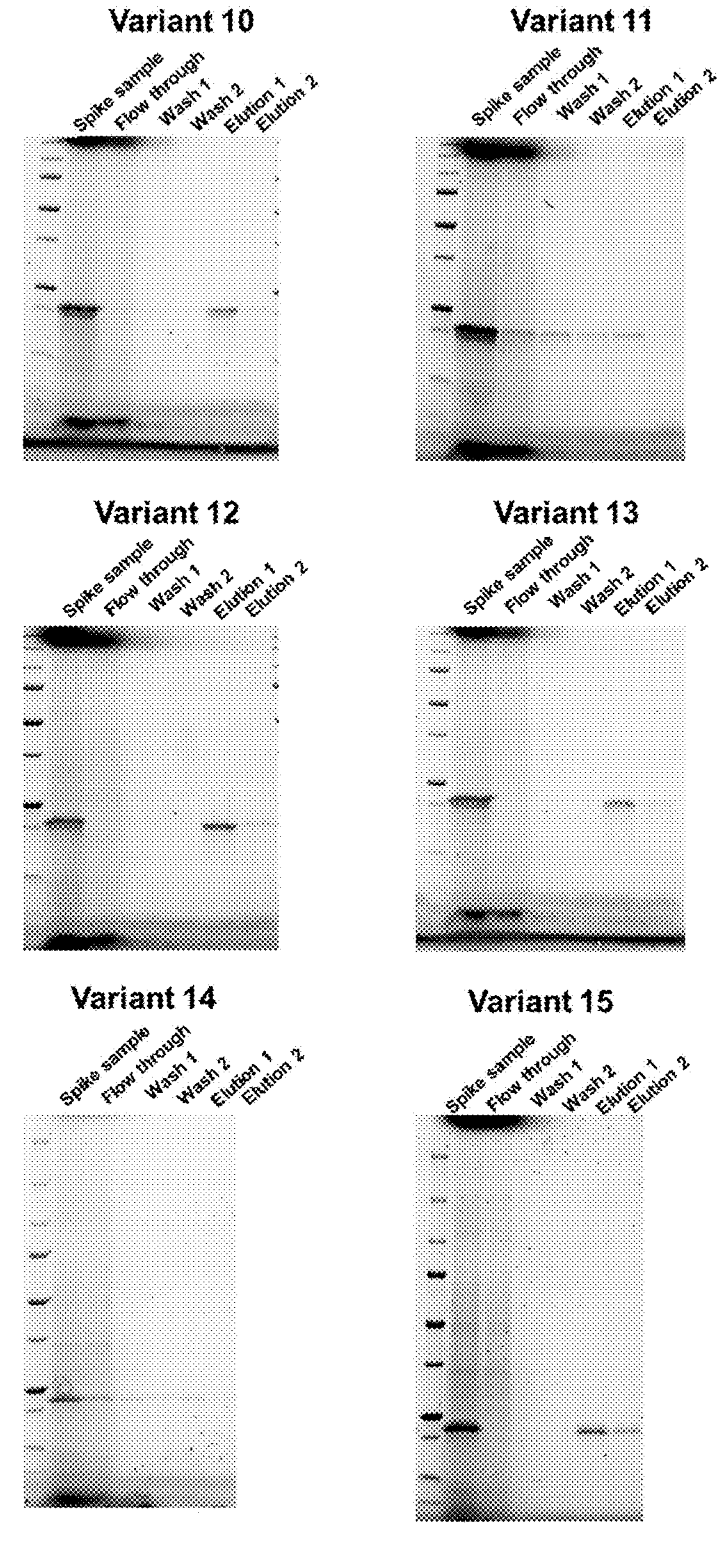

FIG. 3: SpA-assisted purification of humanized NbALFA variants. SpA purification of SpA binding-optimized variants. Spiking experiments of the variants into cell culture supernatant were performed followed by SpA chromatography using spin columns.

Figure 4:
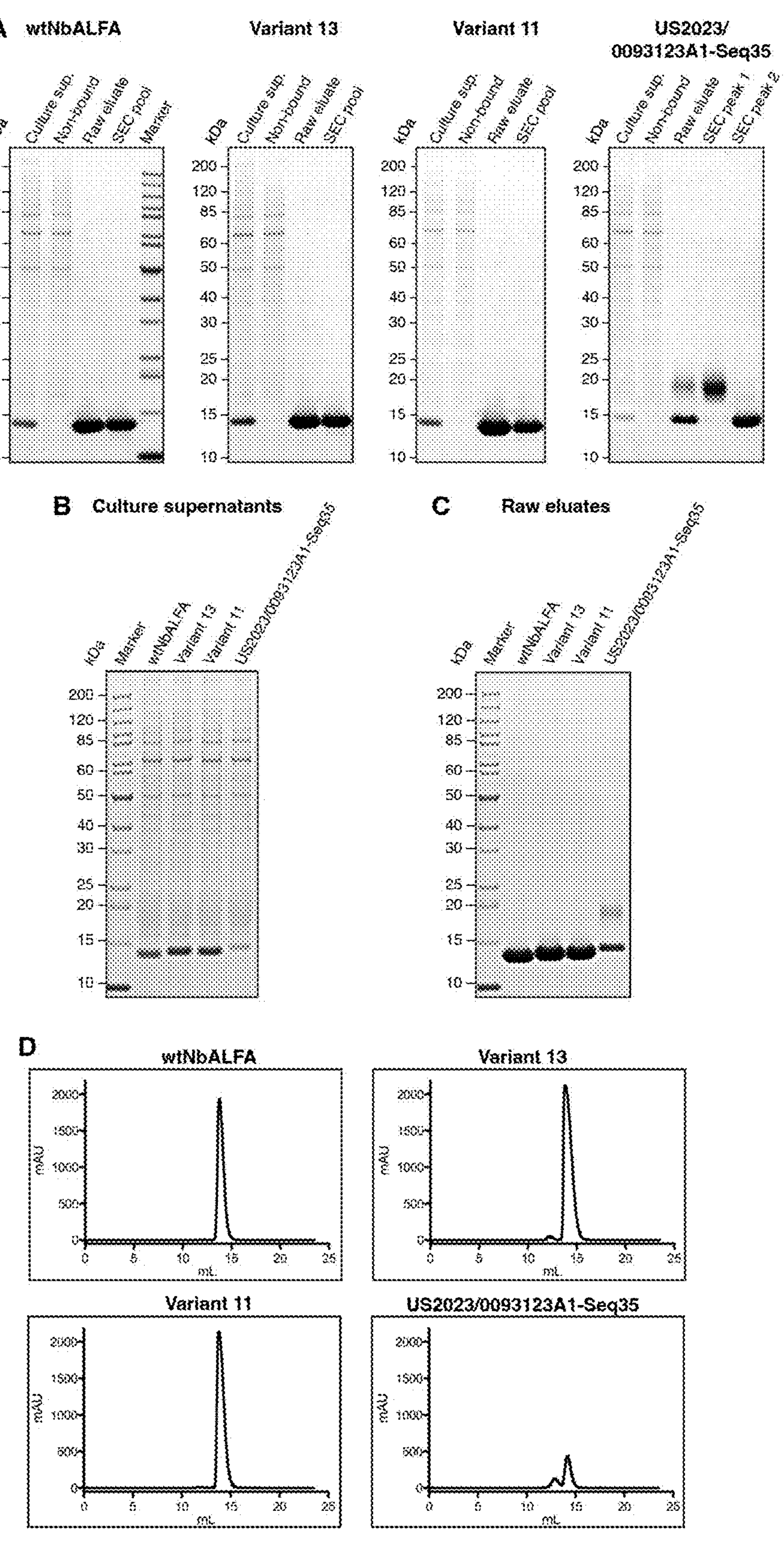

FIG. 4: Direct comparison of NbALFA with three humanized NbALFA variants. A. Purification of NbALFA variants. Indicated fractions were analyzed by SDS-PAGE and Coomassie staining. Analyzed fractions correspond to 2.5 μL of culture supernatant and non-bound material, respectively, and 1 μL of raw eluate after concentration to 1 mL volume. All protein pools after SEC were normalized to two μg per lane. Note that US2023/0093123A1-Seq35 is the only NbALFA variant showing two distinct protein species that can clearly be separated by size-exclusion chromatography (SEC). B. Direct comparison of culture supernatants. Culture supernatants from all four parallel expression cultures were analyzed by SDS-PAGE and Coomassie staining. Analyzed fractions correspond to 5 μL of each culture supernatant. C. Direct comparison of raw eluates. Raw eluates obtained from ALP3 agarose resin were concentrated using spin columns and analyzed by SDS-PAGE and Coomassie staining. Analyzed fractions correspond to 1 μL of concentrated raw eluate. D. Preparative size exclusion chromatography. Raw eluates obtained from ALP3 agarose resin were concentrated to 1 mL final volume and separated on a Superdex 75 increase column equilibrated with PBS. Given are trace files measured at 280 nm at identical scaling. Only for US2023/0093123A1-Seq35, two distinct peaks with significant contribution could be separated. These correspond to glycosylated (peak 1) and non-glycosylated (peak 2) species.

Figure 5:
Figure 5:
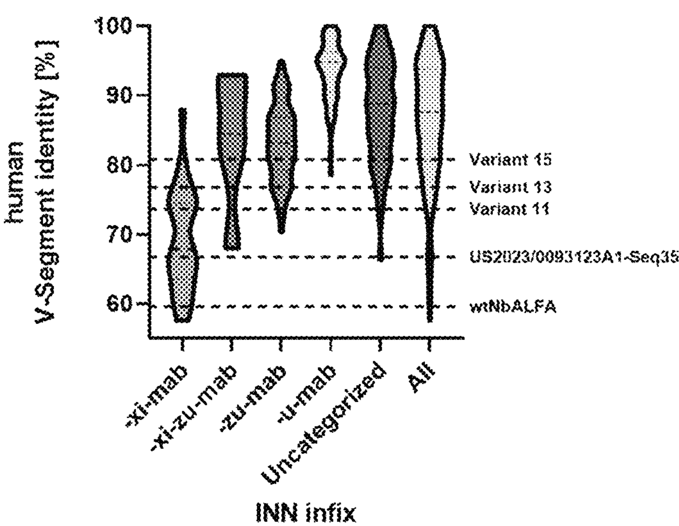

FIG. 5: Human IGHV germline identity of 339 VH domains of antibodies which received INNs. The antibodies were categorized according to their infixes and the germline identity of the respective sub-group was plotted. The V-segment identity of some of the humanized VHHs presented herein are depicted as dashed lines.

DETAILED DESCRIPTION

Humanized antibodies offer the advantage of reduced immunogenicity, as they are engineered to closely resemble human antibodies, minimizing the risk of triggering an immune response when administered to patients. Therefore, humanized antibodies have advantages for in vivo applications, such as for imaging techniques. Furthermore, antibodies binding to epitope tags are becoming increasingly interesting for various therapeutic applications (Mitwasi et al., Sci. Rep. 2020; doi:10.1038/s41598-020-59082-4).

The inventors of the present application have therefore contemplated, that there is a need in the art for providing humanized single-domain antibodies that bind to the peptide of SEQ ID NO: 2 with high affinity. Therefore, the inventors of the present invention aimed to humanize the NbALFA antibody to bridge the gap in the art.

Humanization of antibodies can be conducted for classical VH/VL-based molecules as well as their single domain counterparts. One approach that is commonly used is CDR grafting onto humanized acceptor frameworks, in order to retain the spatial orientation of the original variable region from which the donor CDRs are derived. For humanization of VHH regions, the CDRs can be grafted into a compatible human light chain variable region framework. However, sequence grafting can have unexpected and undesired effect on antibody conformation (Fernández-Quintero et al., Prot. Eng. Des. and Sel., 2019; doi: 10.1093/protein/gzaa004). As a result, the provision of humanized antibodies that has at least comparable binding affinity as the original antibody remains challenging.

When the inventors of the present invention attempted to humanize the wt NbALFA single domain antibody, they initially generated seven humanized variants (variants 1-7) by CDR grafting into various humanized acceptor frameworks. However, the resulting single-domain antibodies either could not be expressed or their affinity for the target antigen was completely lost or significantly impaired (see Example 1).

Having realized that CDR grafting does not straightforwardly result in the generation of high-affinity humanized versions of NbALFA, the inventors of the present application have analysed the structure of the antibody in detail and tested the effect of retaining residues that may be relevant for high affinity binding. Thereby, they have unexpectedly found that, in addition to CDR grafting, several key residues of wt NbALFA should be retained in order to arrive at humanized versions of NbALFA, which retain their high affinity for peptide of SEQ ID NO: 2 or which surprisingly have an even improved affinity (see Example 2). Furthermore, the inventors of the present application have surprisingly found, that so-generated humanized versions of NbALFA can even have an improved thermal stability (see Example 4).

Without wishing to be bound by theory, the inventors of the present application consider that the arginine residue at position 47 of wt NbALFA is important for the interaction of the antibody with the C-terminus of the peptide of SEQ ID NO: 2, and, therefore, retaining Arg 47 of the original camelid VHH framework was considered to improve binding behavior. Furthermore, without wishing to be bound by theory, the inventors of the present application consider that the methionine at position 50 is important for the formation the hydrophobic pocket which would be shielded by the peptide of SEQ ID NO: 2 upon binding, adding free energy to the interaction of antibody and antigen. Thus, retaining Met 50 of the original camelid VHH framework was also considered to improve binding behavior. Further, without wishing to be bound by theory, the inventors of the present application consider that the arginine residue at position 48 of wt NbALFA is also important for binding of the peptide of SEQ ID NO: 2. Hence, retaining Arg 48 of the original camelid VHH framework was also considered to improve binding behavior. These three positions, Arg 47, Arg 48, and Met 50 where thus considered as key residues, which should be retained in a humanized version of NbALFA. In fact, tested variants 8-15 in Example 2 all comprise these three key residues and all variants 8-15 have a binding affinity that is at least comparable to wt NbALFA.

Without wishing to be bound by theory, the inventors of the present application further considered that His 99 and/or Val 100 may be involved in NbALFA binding. These two amino acid residues are believed to influence the conformation of CDR3.

A further residue that is considered to improve the binding of the peptide of SEQ ID NO: 2 is Tyr 40 of wt NbALFA. Without wishing to be bound by theory, the inventors of the present application consider that Tyr 40 forms a hydrogen bond with the R11' side chain on the peptide, which is found in wt NbALFA. By retaining Tyr 40 in a humanized version of NbALFA, antigen binding can be further improved. However, as shown in variant 8, which comprises a Phe at position 40, a binding affinity that is comparable to wt NbALFA can also be achieved without a Tyr residue at position 40. However, by replacing the Phe at position 40 with Tyr, as shown in variant 9, the binding affinity to the peptide of SEQ ID NO: 2 can be further improved.

On the other hand, the inventors of the present application have surprisingly found that Met 61 and Glu 64 which would form part of CDR2 as determined according to Kabat, are not essential for binding to the peptide of SEQ ID NO: 2. These residues can be mutated to their human germline counterparts, e.g., to further humanize the antibody, while the high binding affinity to the peptide of SEQ ID NO: 2 can be retained.

Following this rational, the inventors of the present application have created humanized versions of the NbALFA single domain antibody with reduced immunogenic potential and which can be preferably used in in vivo applications in human patients, such as diagnostic or therapeutic applications.

Furthermore, the inventors of the present invention have surprisingly found that in addition to their reduced immunogenicity, several humanized versions of NbALFA can be bound by Staphylococcal protein A (SpA; see Example 3). Antibodies that can be bound by SpA have the advantage, that GMP production of the antibody is facilitated. Therefore, the binding affinity towards SpA is a further advantage of some humanized antibodies of the present invention. Surprisingly, the inventors of the present application found that introducing mutations into CDR2 as determined according to IMGT, in particular the mutation Ala 60→Thr, and/or into positions that would fall within the CDR2, if determined according to Kabat, in particular the mutation Gln 67→Lys, retains the high binding affinity to the peptide of SEQ ID NO: 2, while promoting SpA binding.

Accordingly, the present invention relates to a single-domain antibody, that specifically binds to an epitope comprising the sequence SRLEEELRRRLTE (SEQ ID NO: 2), wherein the antibody comprises the CDR1 sequence as shown in SEQ ID NO: 94 or a sequence having 1 or 2 mutations relative to said sequence, the CDR2 sequence as shown in SEQ ID NO: 97 or a sequence having 1 or 2 mutations relative to said sequence, and the CDR3 sequence as shown in SEQ ID NO: 98 or a sequence having 1 or 2 mutations relative to said sequence. The antibody preferably further comprises at positions corresponding to sequence position 47, 48, and/or 50 of SEQ ID NO: 1 at least one of the following amino acid residues: Arg at position 47, Arg at position 48, and/or Met at position 50.

The term "antibody" generally refers to a proteinaceous binding molecule with immunoglobulin-like functions. Typical examples of an antibody are, but are not limited to, immunoglobulins, as well as derivatives or functional fragments thereof which still retain the binding specificity. Techniques for the production of antibodies are well known in the art. The term "antibody" also includes immunoglobulins (Ig's) of different classes (i.e. IgA, IgG, IgM, IgD, IgE, IgY etc.) and subclasses (such as IgG1, IgG2 etc.), even if recombinantly produced in foreign hosts using techniques known to those skilled in the art. Illustrative examples of an antibody are full length immunoglobulins, Fab fragments, $F(ab')_2$, Fv fragments, single-chain Fv fragments (scFv), diabodies or domain antibodies. Domain antibodies may be single-domain antibodies, single variable domain antibodies or immunoglobulin single variable domain having only one variable domain, which may be VH or VL, that specifically bind an antigen or epitope independently of other V regions or domains. A particularly preferred single-domain antibody is a VHH domain of a heavy chain only antibody. Such an immunoglobulin single variable domain may not only encompass an isolated antibody single variable domain polypeptide, but also a larger polypeptide that includes or consists of one or more monomers of an antibody single variable domain polypeptide sequence. It is understood that a single-domain antibody may comprise a VHH domain and a fusion partner, such as a protein or peptide, which may be a tag. The definition of the term "antibody" thus also includes embodiments such as chimeric, single chain and humanized antibodies. The term "antibody" may also include fragments of antibodies.

An immunoglobulin when used herein, may be a dimeric glycosylated protein composed of two heavy chains such as a camelid heavy chain only IgG (hcIgG) or a shark IgNAR. An immunoglobulin as used herein may also be a tetrameric glycosylated protein composed of two light (L) chains of approximately 25 kDa each and two heavy (H) chains of approximately 50 kDa each.

The terms "Fab", "Fab region", "Fab portion" or "Fab fragment" are understood to define a polypeptide that includes a $V_H$, a $C_H1$, a $V_L$, and a $C_L$ immunoglobulin domain. Fab may refer to this region in isolation, or this region in the context of an antibody molecule according to the invention, as well as a full-length immunoglobulin or immunoglobulin fragment. Typically a Fab region contains an entire light chain of an antibody. A Fab region can be taken to define "an arm" of an immunoglobulin molecule. It contains the epitope-binding portion of that Ig. The Fab region of a naturally occurring immunoglobulin can be obtained as a proteolytic fragment by a partial papain-digestion. A "$F(ab')_2$ portion" is the proteolytic fragment of a partially pepsin-digested immunoglobulin. A "Fab' portion" is the product resulting from reducing the disulfide bonds of an $F(ab')_2$ portion. As used herein the terms "Fab", "Fab region", "Fab portion" or "Fab fragment" may further include a hinge region that defines the C-terminal end of the antibody arm (cf. above). This hinge region corresponds to the hinge region found C-terminally of the $C_H1$ domain within a full-length immunoglobulin at which the arms of the antibody molecule can be taken to define a Y. The term hinge region is used in the art because immunoglobulin has some flexibility at this region.

An "Fv" or "Fv fragment" consists of only the VL and VH domains of a "single arm" of an immunoglobulin. Thus an "Fv" is the minimum antibody fragment which contains a complete antigen-recognition and binding site. A "two-chain" Fv fragment consists of a dimer of one heavy- and one light-chain variable domain in a tight, non-covalent association. A single-chain Fv species (scFv) includes a VH and a VL domain of an immunoglobulin, with these domains being present in a single polypeptide chain in which they are covalently linked to each other by a flexible peptide linker. Typically, in a scFv fragment the variable domains of the light and heavy chain associate in a dimeric structure analogous to that in a two-chain Fv species. In single chain Fv fragments, it is possible to either have the variable domain of the light chain arranged at the N-terminus of the single polypeptide chain, followed by the linker and the variable domain of the heavy chain arranged at the C-terminus of the polypeptide chain or vice versa, having the variable domain of the heavy chain arranged on the N-terminus and the variable domain of the light chain at the C-terminus with the peptide linker arranged in between. The peptide linker can be any flexible linker known in the art, for example, made from glycine and serine residues. It is also possible to additionally stabilize the domain association between the VH and the VL domain by introducing disulfide bonds into conserved framework regions (see Reiter et al. Stabilization of the Fv fragments in recombinant immunotoxins by disulfide bonds engineered into conserved framework regions, Biochemistry 1994, 33, 6551-5459). Such scFv fragments are also known as disulfide-stabilized scFv fragments (ds-scFv).

The term "Fc region" or "Fc fragment" is used herein to define a C-terminal region of an immunoglobulin heavy chain, including native-sequence Fc regions and variant Fc regions. The Fc part mediates the effector function of antibodies, e.g. the activation of the complement system and of Fc-receptor bearing immune effector cells, such as NK cells. In human IgG molecules, the Fc region is generated by papain cleavage N-terminal to Cys226. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody molecule, or by recombinantly engineering the nucleic acid encoding a heavy chain of the antibody molecule. Accordingly, a composition of intact antibodies may include antibody populations with all K447 residues removed, antibody populations with no K447 residues removed, and antibody populations having a mixture of antibodies with and without the K447 residue. Suitable native-sequence Fc regions for use in the antibodies of the invention include mammalian, e.g. human or murine, IgG1, IgG2 (IgG2A, IgG2B), IgG3 and IgG4. The Fc region contains two or three constant domains, depending on the class of the antibody. In embodiments where the immunoglobulin is an IgG the Fc region has a CH2 and a CH3 domain.

Single-domain antibodies are antibodies whose complementary determining regions are part of a single domain polypeptide. Examples include, but are not limited to, heavy chain antibodies, antibodies naturally devoid of light chains, single-domain antibodies derived from conventional 4-chain antibodies, engineered antibodies and single domain scaffolds other than those derived from antibodies. Single-domain antibodies may be any of the art, or any future single-domain antibodies. Single-domain antibodies may be derived from any species including, but not limited to mouse, human, camel, llama, goat, rabbit, or cattle. A single-domain antibody as used herein can be derived from a naturally occurring antibody known as heavy chain antibody devoid of light chains. Such single-domain antibodies are disclosed in WO 94/04678 for example. For clarity reasons, this variable domain derived from a heavy chain antibody naturally devoid of light chain is known herein as a VHH to distinguish it from the conventional VH of four chain immunoglobulins. Such a VHH molecule can be derived from antibodies raised in Camelidae species, for example in camel, dromedary, llama, vicuña, alpaca and guanaco. Other species besides Camelidae may produce heavy chain antibodies naturally devoid of light chain. As an illustrative example, it is known that sharks produce heavy chain antibodies naturally devoid of light chains (commonly named IgNAR), which also comprise a VHH domain. Furthermore, some species have been genetically modified to artificially produce heavy chain antibodies naturally devoid of light chain, such as certain mouse strains. In addition, VHHs may be obtained from synthetic libraries. All such VHHs are within the scope of the disclosure. Single-domain antibodies as used herein also includes humanized versions of single-domain antibodies, such as humanized versions of a VHH region.

VHHs, according to the present disclosure, and as known to the skilled addressee are preferably heavy chain variable domains derived from immunoglobulins naturally devoid of light chains such as those derived from Camelidae as described in WO 94/04678 (and referred to hereinafter as VHH domains or nanobodies). VHH molecules are about 10× smaller than IgG molecules. They are single polypeptides and very stable, resisting extreme pH and temperature conditions. Moreover, they are highly resistant to the action of proteases, which is not the case for conventional antibodies. Furthermore, in vitro expression of VHHs or expression in prokaryotic or eukaryotic organisms suited for recombinant protein expression produces high yield, properly folded functional VHHs.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable regions", "HVR," or "HV," or "complementarity determining regions" (CDRs). The more conserved (i.e., non-hypervariable) portions of the variable domains are called the "framework" regions (FR). The variable domains of naturally occurring heavy and light chains each include four FR regions, largely adopting a β-sheet configuration, connected by three hypervariable regions, which form loops connecting, and in some cases forming part of, the β-sheet structure. The hypervariable regions in each chain are held together in close proximity by the FR and, with the hypervariable regions from the other chain, contribute to the formation of the antigen-binding site (see Kabat et al., see below). Generally, naturally occurring immunoglobulins include six CDRs (see below); three in the VH (H1, H2, H3), and three in the VL (L1, L2, L3). In naturally occurring immunoglobulins, H3 and L3 display the most diversity of the six CDRs, and H3 in particular is believed to play a unique role in conferring fine specificity to immunoglobulins. Immunoglobulins naturally devoid of light chains, however, include three CDRs that are in the VHH region. The constant domains are not directly involved in antigen binding, but exhibit various effector functions, such as, for example, antibody-dependent, cell-mediated cytotoxicity and complement activation.

Unless otherwise indicated, explicitly or implicitly, CDRs sequences of the present disclosure follow a hybrid Kabat/IMGT definition. Heavy chain CDR1 follows a hybrid Kabat/IMGT definition, the begin of heavy chain CDR1 follows the definition of IMGT, whereas the end of heavy chain CDR1 follows the definition of Kabat. As an illustrative example, the CDR1 of wtNbALFA according to IMGT is GVTISALNAMA (SEQ ID NO: 127), while the CDR1 of wtNbALFA according to Kabat is ALNAMAMG (SEQ ID NO: 128). According to the hybrid Kabat/IMGT definition that is preferably used in the context of the present disclosure, the CDR1 sequence of wtNbALFA is GVTISALNAMAMG (SEQ ID NO: 94). Heavy chain CDR2 and CDR3 are defined according to IMGT definition. Light chain CDR sequences are likewise defined according to IMGT definition. The reason for the hybrid definition of heavy chain CDR1 is to contain a longer sequence to assure that the CDR1 graft includes all important residues. For CDR definition see, generally, e.g., Dondelinger et al., 'Understanding the Significance and Implications of Antibody Numbering and Antigen-Binding Surface/Residue Definition', 2018; doi: 10.3389/fimmu.2018.02278. Other standards for defining CDRs exist as well, such as the definition according to Maass 2007 (Journal of Immunological Methods 324 (2007) 13-25). Another standard for characterizing the antigen binding site is to refer to the hypervariable loops as described by Chothia (see, e.g., Chothia, et al. (1992); J. Mol. Biol. 227:799-817; and Tomlinson et al. (1995) EMBO J. 14:4628-4638).

In line with the CDR definition as described herein, unless otherwise indicated, explicitly or implicitly, the FR regions as used herein follow a hybrid Kabat/IMGT definition. For heavy chain variable regions, FR1, FR3, and FR4 are defined according to IMGT definition. For FR2 of the heavy chain variable region, the beginning is defined according to Kabat definition, while the end is defined according to IMGT definition. Accordingly, as an illustrative example, FR1 of wtNbALFA is preferably defined by amino acid positions 1-25 of SEQ ID NO: 1, FR2 of wtNbALFA is preferably defined by amino acid positions 39-53 of SEQ ID NO: 1, FR3 of wtNbALFA is preferably defined by amino acid positions 61-98 of SEQ ID NO: 1, and FR4 of wtNbALFA is preferably defined by amino acid positions 112-122 of SEQ ID NO: 1.

Each VHH, VH and VL has three CDRs and four FRs, arranged from amino-terminus (N-terminus) to carboxy-terminus (C-terminus) in the following order: FR1, CDR1, FR2, CDR2, FR3, CDR3, and FR4. The variable regions of the heavy and/or light chains contain a binding domain that interacts with an epitope of an antigen. The term "immunoglobulin" may refer to protein that may have two heavy chains without light chains, such as e.g. an antibody devoid of light chains, or an antigen-binding portion thereof. An immunoglobulin may also include at least two heavy (H) chains and two light (L) chains linked by disulfide bonds, or an antigen-binding portion thereof.

An antibody according to the invention may be an isolated antibody molecule. The term "isolated antibody molecule" as used herein refers to an antibody molecule that has been identified and separated and/or recovered from a component of its natural environment. Contaminant components of its natural environment are matter that would interfere with uses for the antibody, and may include enzymes, hormones, and other proteinaceous or non-proteinaceous solutes. In some embodiments the antibody molecule is purified to greater than 95% by weight of antibody as determined by the Lowry method, such as more than 99% by weight. In some embodiments the antibody molecule is purified to a degree sufficient to obtain at least 15 residues of N-terminal or internal amino acid sequence by use of a spinning cup sequenator. In some embodiments the antibody is purified to homogeneity as judged by SDS-PAGE under reducing or non-reducing conditions using Coomassie blue or, preferably, silver stain. An isolated antibody molecule may in some embodiments be present within foreign host cells with one or more component(s) of the antibody's natural environment not being present. Typically, an isolated antibody is prepared by at least one purification step.

An antibody or antibody molecule/fragment is said to "specifically" bind to an antigen when it recognizes its target antigen within a complex mixture of proteins and/or macromolecules. Typically, the antibody is capable of specifically interacting with and/or binding to its target but does not essentially bind to another (preferably non-related) epitope or antigen. Antibodies are said to "bind to the same epitope" if the antibodies cross-compete so that only one antibody can bind to the epitope at a given point of time, i.e. one antibody prevents the binding or modulating effect of the other. An antibody or antibody molecule/fragment that specifically binds to a certain target, can however be cross-reactive with structures that are similar, such as with closely related variants of the target it specifically binds to.

Typically, binding that is considered specific may also have a high affinity, e.g. when the binding affinity is higher than $10^{-6}$ M (in terms of $K_D$). In particular, the binding affinity may be about $10^{-8}$ to $10^{-11}$ M ($K_D$), or of about $10^{-9}$ to $10^{-11}$ M or even higher. Thus, antibody molecules with an affinity in the picomolar range (with a Kd of $9.9\times10^{-10}$ M to $10^{-2}$ M) are also encompassed in the present invention. If necessary, nonspecific binding of a binding site can be reduced without substantially affecting specific binding by varying the binding conditions.

The term "epitope", also known as the "antigenic determinant", refers to the portion of an antigen to which an antibody specifically binds, thereby forming a complex. Thus, the term "epitope" includes any molecule or protein determinant capable of specific binding to an immunoglobulin or T-cell receptor. The binding site(s) (paratope) of an antibody molecule described herein may specifically bind to/interact with conformational or continuous epitopes, which are unique for the target structure. Epitopic determinants usually consist of chemically active surface groupings of molecules such as amino acids or sugar side chains and usually have specific three-dimensional structural characteristics, as well as specific charge characteristics. Epitope determinants may include chemically active surface groupings of molecules such as amino acids, sugar side chains, phosphoryl, or sulfonyl, and, in certain embodiments, may have specific three-dimensional structural characteristics, and/or specific charge characteristics. With regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen (Sela, M., Science (1969) 166, 1365-1374; Laver, W. G., et al. Cell (1990) 61, 553-556). The two or more discrete amino acid residues contributing to the epitope may be present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues, which are present in a single linear segment of a polypeptide chain. As an illustrative example, a "context-dependent" CD3 epitope refers to the conformation of said epitope. Such a context-dependent epitope, localized on the epsilon chain of CD3, can only develop its correct conformation if it is embedded within the rest of the epsilon chain and held in the right position by heterodimerization of the epsilon chain with either CD3 gamma or delta chain. In contrast thereto, a context-independent CD3 epitope may be an N-terminal 1-27 amino acid residue polypeptide or a functional fragment thereof of CD3 epsilon. Generally, epitopes can be linear in nature or can be a discontinuous epitope. Thus, as used herein, the term "conformational epitope" refers to a discontinuous epitope formed by a spatial relationship between amino acids of an antigen other than an unbroken series of amino acids. The term "epitope" also includes an antigenic determinant of a hapten, which is known as a small molecule that can serve as an antigen by displaying one or more immunologically recognized epitopes upon binding to larger matter such as a larger molecule e.g. a protein.

As used herein, an "epitope tag" refers to a stretch of amino acids to which a specific antibody or proteinaceous molecule with antibody-like function can be raised. Such an epitope tag may allow for specifically identifying and/or tracking of the tagged polypeptide or protein that may be present in a living organism or cultured cells. Detection of the tagged molecule can be achieved using a number of different techniques. of such Examples techniques include: immunohistochemistry, immunoprecipitation, flow cytometry, immunofluorescence microscopy, electron microscopy, ELISA, immunoblotting ("Western blot"), and affinity chromatography. The epitope tag adds a known epitope (antibody binding site) on the subject polypeptide, to provide binding of a known and often high-affinity antibody. An epitope tag may also be used for isolation and/or purification of the tagged molecule, e.g. by pull-down applications.

The term "mutation" as used herein refers to changes in sequences of biomolecules, such as amino acids sequence of a protein or nucleic acid sequence of DNA or RNA. Mutations include deletions, insertions, and substitutions, and these can apply to single nucleotides/amino acids as well as large sections of nucleotides/amino acid sequences.

As mentioned herein, an antibody of the invention comprises at positions corresponding to sequence position 47, 48, and/or 50 of SEQ ID NO: 1 at least one of the following amino acid residues: Arg at position 47, Arg at position 48, and/or Met at position 50.

Preferably, the antibody of the invention comprises at the position corresponding to sequence position 47 of SEQ ID NO: 1 an Arg residue. Preferably, the antibody of the invention comprises at the position corresponding to sequence position 48 of SEQ ID NO: 1 an Arg residue. Preferably, the antibody of the invention comprises at the position corresponding to sequence position 50 of SEQ ID NO: 1 a Met residue. Any one of these residues are believed to contribute to the binding of NbALFA to the target of SEQ ID NO: 2.

Preferably, the antibody of the invention comprises at positions corresponding to sequence positions 47, 48, and/or 50 of SEQ ID NO: 1 at least two of the following amino acid residues: Arg at position 47, Arg at position 48, and/or Met at position 50. More preferably, the antibody of the invention preferably comprises at positions corresponding to sequence positions 47, 48, and 50 of SEQ ID NO: 1 the following amino acid residues: Arg at position 47, Arg at position 48, and Met at position 50.

Apart from positions 47, 48, and 50, also retaining a Tyr residue at position 40 is considered to improve and antibody of the invention's affinity to SEQ ID NO: 2. While also single-domain antibodies not having a Tyr residue at position 40 may have comparably binding affinity to SEQ ID NO: 2 as compared to wtNbALFA, such as variant 8, other variants having a Tyr at said position may show further improved affinity. Accordingly, an antibody of the present invention may preferably comprise a Tyr residue at the position corresponding to sequence position 40 of SEQ ID NO: 1. Thus, the antibody of the invention preferably comprises at positions corresponding to sequence positions 40, 47, 48, and 50 of SEQ ID NO: 1 the following amino acid residues: Tyr at position 40, Arg at position 47, Arg at position 48, and Met at position 50.

Further, it is also postulated that the His residue at position 99 and/or Val residue at position 100 may positively influence the binding affinity to SEQ ID NO: 2 of an antibody of the invention. Accordingly, an antibody of the present invention may preferably comprise a His residue at the position corresponding to sequence position 99 of SEQ ID NO: 1. Accordingly, an antibody of the present invention may preferably comprise a Val residue at the position corresponding to sequence position 100 of SEQ ID NO: 1. Thus, an antibody of the present invention may preferably comprise a His residue at the position corresponding to sequence position 99 of SEQ ID NO: 1 and a Val residue at the position corresponding to sequence position 100 of SEQ ID NO: 1. Thus, an antibody of the invention preferably comprises at positions corresponding to sequence positions 47, 48, 50, 99, and 100 of SEQ ID NO: 1 the following amino acid residues: Arg at position 47, Arg at position 48, Met at position 50, His at position 99, and Val at position 100. Thus, an antibody of the invention preferably comprises at positions corresponding to sequence positions 40, 47, 48, 50, 99, and 100 of SEQ ID NO: 1 the following amino acid residues: Tyr at position 40, Arg at position 47, Arg at position 48, Met at position 50, His at position 99, and Val at position 100.

In the antibodies of the present invention, further native amino acids of wtNbALFA may be retained. Accordingly, an antibody of the invention may comprise a Gln residue at the position corresponding to sequence position 5 of SEQ ID NO: 1. However, without wishing to be bound by theory, Gln at position 5 is believed to be of minor importance for binding the peptide of SEQ ID NO: 2, in a preferred embodiment the position 5 corresponding to SEQ ID NO: 1 comprises Val. Further, an antibody of the invention preferably comprises a Gln residue at the position corresponding to sequence position 117 of SEQ ID NO: 1. However, without wishing to be bound by theory, Gln at position 117 is believed to be of minor importance for binding of the peptide of SEQ ID NO: 2, however, Gln 117 is believed to increase solubility. Thus, an antibody of the invention preferably comprises a Val residue at the position corresponding to sequence position 5 of SEQ ID NO: 1 and a Gln residue at the position corresponding to sequence position 117 of SEQ ID NO: 1. Preferably, the antibody of the invention comprises at positions corresponding to sequence positions 5, 47, 48, 50, and 117 of SEQ ID NO: 1 the following amino acid residues: Val at position 5, Arg at position 47, Arg at position 48, Met at position 50, and Gln at position 117. Preferably, the antibody of the invention comprises at positions corresponding to sequence positions 5, 47, 48, 50, 99, 100, and 117 of SEQ ID NO: 1 the following amino acid residues: Val at position 5, Arg at position 47, Arg at position 48, Met at position 50, His at position 99, and Val at position 100, and Gln at position 117. Preferably, the antibody of the invention comprises at positions corresponding to sequence positions 5, 40, 47, 48, 50, 99, 100, and 117 of SEQ ID NO: 1 the following amino acid residues: Val at position 5, Tyr at position 40, Arg at position 47, Arg at position 48, Met at position 50, His at position 99, and Val at position 100, and Gln at position 117. In wt NbALFA, Met 61 and Glu 64 form part of CDR2 determined according to Kabat. Nevertheless, the inventors of the present application have surprisingly found that these two residues are not crucial for binding of the peptide of SEQ ID NO: 2. By mutating the two residues to the human IGHV3-23 derived sequence counterparts, Tyr 61 and/or Asp 64, high binding affinity to the peptide of SEQ ID NO: 2 can be retained, as shown in variants 13 and 15. An antibody of the invention may also comprise a Tyr residue at the position corresponding to sequence position 61 of SEQ ID NO: 1. An antibody of the invention may also comprise an Asp residue at the positions corresponding to sequence position 64 of SEQ ID NO: 1. An antibody of the invention may also comprises a Tyr residue at the position corresponding to sequence position 61 of SEQ ID NO: 1 and an Asp residue at the position corresponding to sequence position 64 of SEQ ID NO: 1.

When used in connection with a protein or peptide, the term "amino acid" or "amino acid residue" typically refers to an α-amino carboxylic acid having its art recognized definition such as an amino acid selected from the group consisting of: L-alanine (Ala or A); L-arginine (Arg or R); L-asparagine (Asn or N); L-aspartic acid (Asp or D); L-cysteine (Cys or C); L-glutamine (Gln or Q); L-glutamic acid (Glu or E); glycine (Gly or G); L-histidine (His or H); L-isoleucine (Ile or I): L-leucine (Leu or L); L-lysine (Lys or K); L-methionine (Met or M); L-phenylalanine (Phe or F); L-proline (Pro or P); L-serine (Ser or S); L-threonine (Thr or T); L-tryptophan (Trp or W); L-tyrosine (Tyr or Y); and L-valine (Val or V), although modified, synthetic, or rare amino acids such as e.g. taurine, ornithine, selenocysteine, homocystine, hydroxyproline, thioproline, iodo-tyrosine, 3-nitro-tyrosine, ornithine, citrulline, canavanine, 5-hydroxytryptophane, carnosine, cycloleucine, 3,4-dihydroxy phenylalanine, N-acetylcysteine, prolinol, allylglycine or acetidine-2-carboxylic acid may be used as desired. Generally, amino acids can be grouped as having a nonpolar side chain (e.g., Ala, Cys, Ile, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr).

A single-domain antibody of the invention preferably comprises a sequence having at least 80%, at least 85%, at least 90%, at least 95%, at least 98%, or at least 99% sequence identity or being identical to any one of SEQ ID NOs: 118-125. Preferably, an antibody of the invention comprises a sequence having at least 90% sequence identity to any one of SEQ ID NOs: 118-125. Preferably, an antibody of the invention comprises a sequence having at least 95% sequence identity to any one of SEQ ID NOs: 118-125. Preferably, an antibody of the invention comprises a sequence having at least 98% sequence identity to any one of SEQ ID NOs: 118-125. Preferably, an antibody of the invention comprises a sequence having at least 99% sequence identity to any one of SEQ ID NOs: 118-125. Preferably, an antibody of the invention comprises or consist of an amino acid sequence selected from the group consisting of:

```
a.
                                              (SEQ ID NO: 118)
EVQLVESGGGLVQPGGSLRLSCAASGVTISALNAMAMGWFRQAPGKR

REMVAAVSERGNAMYRESVQGRFTISRDNAKRMVYLQMNSLRAEDTA

VYYCHVLEDRVDSFHDYWGQGTQVTVSS;

b.
                                              (SEQ ID NO: 119)
EVQLVESGGGLVQPGGSLRLSCAASGVTISALNAMAMGWYRQAPGKR

REMVAAVSERGNAMYRESVQGRFTISRDNAKRMVYLQMNSLRAEDTA

VYYCHVLEDRVDSFHDYWGQGTQVTVSS;
```

-continued

```
c.
                                              (SEQ ID NO: 120)
EVQLVESGGGLVQPGGSLRLSCAASGVTISALNAMAMGWYRQAPGKR

REMVAAVSERGNTMYRESVQGRFTISRDNAKRMVYLQMNSLRAEDTA

VYYCHVLEDRVDSFHDYWGQGTQVTVSS;

d.
                                              (SEQ ID NO: 121)
EVQLVESGGGLVQPGGSLRLSCAASGVTISALNAMAMGWYRQAPGKR

REMVAAVSERGNAMYRESVKGRFTISRDNAKRMVYLQMNSLRAEDTA

VYYCHVLEDRVDSFHDYWGQGTQVTVSS;

e.
                                              (SEQ ID NO: 122)
EVQLVESGGGLVQPGGSLRLSCAASGVTISALNAMAMGWYRQAPGKR

REMVAAVSERGNTMYRESVKGRFTISRDNAKRMVYLQMNSLRAEDTA

VYYCHVLEDRVDSFHDYWGQGTQVTVSS;

f.
                                              (SEQ ID NO: 123)
EVQLVESGGGLVQPGGSLRLSCAASGVTISALNAMAMGWYRQAPGKR

REMVAAVSERGNTYYRDSVKGRFTISRDNAKRMVYLQMNSLRAEDTA

VYYCHVLEDRVDSFHDYWGQGTQVTVSS;

g.
                                              (SEQ ID NO: 124)
EVQLVESGGGLVQPGGSLRLSCAASGVTISALNAMAMGWYRQAPGKR

REMVAAVSERGNAMYRESVKGRFTISRDNSKNTLYLQMNSLRAEDTA

VYYCHVLEDRVDSFHDYWGQGTQVTVSS;
and

h.
                                              (SEQ ID NO: 125)
EVQLVESGGGLVQPGGSLRLSCAASGVTISALNAMAMGWYRQAPGKR

REMVAAVSERGNTYYRDSVKGRFTISRDNSKNTLYLQMNSLRAEDTA

VYYCHVLEDRVDSFHDYWGQGTQVTVSS.
```

A single-domain antibody of the invention preferably comprises a sequence having at least 80%, at least 85%, at least 90%, at least 95%, at least 98%, or at least 99% sequence identity or being identical to SEQ ID NO: 118. Preferably, an antibody of the invention comprises a sequence having at least 90% sequence identity to SEQ ID NO: 118. Preferably, an antibody of the invention comprises a sequence having at least 95% sequence identity to SEQ ID NO: 118. Preferably, an antibody of the invention comprises a sequence having at least 98% sequence identity to SEQ ID NO: 118. Preferably, an antibody of the invention comprises a sequence having at least 99% sequence identity to SEQ ID NO: 118. Preferably, an antibody of the invention comprises or consist of the amino acid sequence set forth in SEQ ID NO: 118.

A single-domain antibody of the invention preferably comprises a sequence having at least 80%, at least 85%, at least 90%, at least 95%, at least 98%, or at least 99% sequence identity or being identical to SEQ ID NO: 119. Preferably, an antibody of the invention comprises a sequence having at least 90% sequence identity to SEQ ID NO: 119. Preferably, an antibody of the invention comprises a sequence having at least 95% sequence identity to SEQ ID NO: 119. Preferably, an antibody of the invention comprises a sequence having at least 98% sequence identity to SEQ ID NO: 119. Preferably, an antibody of the invention comprises a sequence having at least 99% sequence identity to SEQ ID NO: 119. Preferably, an antibody of the invention comprises or consist of the amino acid sequence set forth in SEQ ID NO: 119.

A single-domain antibody of the invention preferably comprises a sequence having at least 80%, at least 85%, at least 90%, at least 95%, at least 98%, or at least 99% sequence identity or being identical to SEQ ID NO: 120. Preferably, an antibody of the invention comprises a sequence having at least 90% sequence identity to SEQ ID NO: 120. Preferably, an antibody of the invention comprises a sequence having at least 95% sequence identity to SEQ ID NO: 120. Preferably, an antibody of the invention comprises a sequence having at least 98% sequence identity to SEQ ID NO: 120. Preferably, an antibody of the invention comprises a sequence having at least 99% sequence identity to SEQ ID NO: 120. Preferably, an antibody of the invention comprises or consist of the amino acid sequence set forth in SEQ ID NO: 120.

A single-domain antibody of the invention preferably comprises a sequence having at least 80%, at least 85%, at least 90%, at least 95%, at least 98%, or at least 99% sequence identity or being identical to SEQ ID NO: 121. Preferably, an antibody of the invention comprises a sequence having at least 90% sequence identity to SEQ ID NO: 121. Preferably, an antibody of the invention comprises a sequence having at least 95% sequence identity to SEQ ID NO: 121. Preferably, an antibody of the invention comprises a sequence having at least 98% sequence identity to SEQ ID NO: 121. Preferably, an antibody of the invention comprises a sequence having at least 99% sequence identity to SEQ ID NO: 121. Preferably, an antibody of the invention comprises or consist of the amino acid sequence set forth in SEQ ID NO: 121.

A single-domain antibody of the invention preferably comprises a sequence having at least 80%, at least 85%, at least 90%, at least 95%, at least 98%, or at least 99% sequence identity or being identical to SEQ ID NO: 122. Preferably, an antibody of the invention comprises a sequence having at least 90% sequence identity to SEQ ID NO: 122. Preferably, an antibody of the invention comprises a sequence having at least 95% sequence identity to SEQ ID NO: 122. Preferably, an antibody of the invention comprises a sequence having at least 98% sequence identity to SEQ ID NO: 122. Preferably, an antibody of the invention comprises a sequence having at least 99% sequence identity to SEQ ID NO: 122. Preferably, an antibody of the invention comprises or consist of the amino acid sequence set forth in SEQ ID NO: 122.

A single-domain antibody of the invention preferably comprises a sequence having at least 80%, at least 85%, at least 90%, at least 95%, at least 98%, or at least 99% sequence identity or being identical to SEQ ID NO: 123. Preferably, an antibody of the invention comprises a sequence having at least 90% sequence identity to SEQ ID NO: 123. Preferably, an antibody of the invention comprises a sequence having at least 95% sequence identity to SEQ ID NO: 123. Preferably, an antibody of the invention comprises a sequence having at least 98% sequence identity to SEQ ID NO: 123. Preferably, an antibody of the invention comprises a sequence having at least 99% sequence identity to SEQ ID NO: 123. Preferably, an antibody of the invention comprises or consist of the amino acid sequence set forth in SEQ ID NO: 123.

A single-domain antibody of the invention preferably comprises a sequence having at least 80%, at least 85%, at least 90%, at least 95%, at least 98%, or at least 99% sequence identity or being identical to SEQ ID NO: 124. Preferably, an antibody of the invention comprises a sequence having at least 90% sequence identity to SEQ ID NO: 124. Preferably, an antibody of the invention comprises a sequence having at least 95% sequence identity to SEQ ID NO: 124. Preferably, an antibody of the invention comprises a sequence having at least 98% sequence identity to SEQ ID NO: 124. Preferably, an antibody of the invention comprises a sequence having at least 99% sequence identity to SEQ ID NO: 124. Preferably, an antibody of the invention comprises or consist of the amino acid sequence set forth in SEQ ID NO: 124.

A single-domain antibody of the invention preferably comprises a sequence having at least 80%, at least 85%, at least 90%, at least 95%, at least 98%, or at least 99% sequence identity or being identical to SEQ ID NO: 125. Preferably, an antibody of the invention comprises a sequence having at least 90% sequence identity to SEQ ID NO: 125. Preferably, an antibody of the invention comprises a sequence having at least 95% sequence identity to SEQ ID NO: 125. Preferably, an antibody of the invention comprises a sequence having at least 98% sequence identity to SEQ ID NO: 125. Preferably, an antibody of the invention comprises a sequence having at least 99% sequence identity to SEQ ID NO: 125. Preferably, an antibody of the invention comprises or consist of the amino acid sequence set forth in SEQ ID NO: 125.

"Percent (%) sequence identity" with respect to amino acid sequences disclosed herein is defined as the percentage of amino acid residues in a candidate sequence that are pair-wise identical with the amino acid residues in a reference sequence, i.e. an antibody molecule of the present disclosure, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The same is true for nucleotide sequences disclosed herein.

As disclosed herein, an antibody of the invention may comprise the CDR1 sequence GVTISALNAMAMG (SEQ ID NO: 94) or a sequence having 1 or 2 mutations relative to said sequence, the CDR2 sequence VSERGNX1, wherein X1 is A or T (SEQ ID NO: 97) or a sequence having 1 or 2 mutations relative to said sequence, and the CDR3 sequence HVLEDRVDSFHDY (SEQ ID NO: 98) or a sequence having 1 or 2 mutations relative to said sequence. Preferably, an antibody of the invention may comprise the CDR1 sequence GVTISALNAMAMG (SEQ ID NO: 94) or a sequence having 1 mutation relative to said sequence, the CDR2 sequence VSERGNX1, wherein X1 is A or T (SEQ ID NO: 97) or a sequence having 1 mutation relative to said sequence, and the CDR3 sequence HVLEDRVDSFHDY (SEQ ID NO: 98) or a sequence having 1 mutation relative to said sequence. More preferably, an antibody of the invention may comprise the CDR1 sequence GVTISALNAMAMG (SEQ ID NO: 94), the CDR2 sequence VSERGNX1, wherein X1 is A or T (SEQ ID NO: 97), and the CDR3 sequence HVLEDRVDSFHDY (SEQ ID NO: 98).

An antibody of the invention preferably comprises a CDR2 sequence having at least 80%, at least 85%, at least 90%, or at least 95% sequence identity or being identical to any one of SEQ ID NO: 95 or 96. Such an antibody of the invention may comprise the CDR2 sequence VSERGNA (SEQ ID NO: 95) or a sequence having 1 or 2 mutations relative to said sequence, or the CDR2 sequence VSERGNT (SEQ ID NO: 96) or a sequence having 1 or 2 mutations relative to said sequence. Preferably, an antibody of the invention comprises the CDR2 sequence of SEQ ID NO: 95 or a sequence having 1 mutation relative to said sequence, or the CDR2 sequence of SEQ ID NO: 96 or a sequence having 1 mutation relative to said sequence. Preferably, an antibody of the invention comprises the CDR2 sequence of SEQ ID NO: 95 or SEQ ID NO: 96.

An antibody of the invention may comprise the CDR1 sequence set forth in SEQ ID NO: 94 or a sequence having 1 or 2 mutations relative to said sequence, the CDR2 sequence set forth in SEQ ID NO: 95 or a sequence having 1 or 2 mutations relative to said sequence, and the CDR3 sequence set forth in SEQ ID NO: 98 or a sequence having 1 or 2 mutations relative to said sequence. Preferably, an antibody of the invention may comprise the CDR1 sequence set forth in SEQ ID NO: 94 or a sequence having 1 mutation relative to said sequence, the CDR2 sequence set forth in SEQ ID NO: 95 or a sequence having 1 mutation relative to said sequence, and the CDR3 sequence set forth in SEQ ID NO: 98 or a sequence having 1 mutation relative to said sequence. More preferably, an antibody of the invention may comprise the CDR1 sequence set forth in SEQ ID NO: 94, the CDR2 sequence set forth in SEQ ID NO: 95, and the CDR3 sequence set forth in SEQ ID NO: 98.

An antibody of the invention may comprise the CDR1 sequence set forth in SEQ ID NO: 94 or a sequence having 1 or 2 mutations relative to said sequence, the CDR2 sequence set forth in SEQ ID NO: 96 or a sequence having 1 or 2 mutations relative to said sequence, and the CDR3 sequence set forth in SEQ ID NO: 98 or a sequence having 1 or 2 mutations relative to said sequence. Preferably, an antibody of the invention may comprise the CDR1 sequence set forth in SEQ ID NO: 94 or a sequence having 1 mutation relative to said sequence, the CDR2 sequence set forth in SEQ ID NO: 96 or a sequence having 1 mutation relative to said sequence, and the CDR3 sequence set forth in SEQ ID NO: 98 or a sequence having 1 mutation relative to said sequence. More preferably, an antibody of the invention may comprise the CDR1 sequence set forth in SEQ ID NO: 94, the CDR2 sequence set forth in SEQ ID NO: 96, and the CDR3 sequence set forth in SEQ ID NO: 98.

It is understood that such an antibody is a single-domain antibody. It is further understood that an antibody of the invention in which 1 or 2 mutations have been introduced to one, two, or all three of the CDR sequences is preferably still capable of specifically binding the peptide of SEQ ID NO: 2 with at least comparable binding affinity as wtNbALFA.

An antibody of the invention preferably comprises an FR1 sequence having at least 80%, at least 85%, at least 90%, or at least 95% sequence identity or being identical to the sequence of EVQLVESGGGLVQPGGSLRLSCAAS (SEQ ID NO: 99).

An antibody of the invention preferably comprises a FR2 sequence at least 80%, at least 85%, at least 90%, or at least 95% sequence identity or being identical to the sequence of WXIRQAPGKRREMVAA wherein X1 is F or Y (SEQ ID NO: 102).

An antibody of the invention preferably comprises a FR3 sequence at least 80%, at least 85%, at least 90%, or at least 95% sequence identity or being identical to the sequence of X1YRX2SVX3GRFTISRDNX4KX5X6X7YLQMNSLRAEDTAVYYC, wherein X1 is M or Y, X2 is D or E, X3 is Q or K, X4 is A or S, X5 is N or R, X6 is M or T, X7 is V or L (SEQ ID NO: 108).

An antibody of the invention preferably comprises a FR4 sequence at least 80%, at least 85%, at least 90%, or at least 95% sequence identity or being identical to the sequence of WGQGTQVTVSS (SEQ ID NO: 109).

Accordingly, an antibody of the invention preferably comprises FR1, FR2, FR3, and FR4 sequences, which each have at least 80%, at least 85%, at least 90%, or at least 95% sequence identity or are identical to the sequences of SEQ ID NOs: 99, 102, 108, and 109, respectively.

An antibody of the invention preferably comprises an FR2 sequence having at least 80%, at least 85%, at least 90%, or at least 95% sequence identity or being identical to any one of SEQ ID NO: 100 or 101. Such an antibody of the invention may comprise the FR2 sequence having at least 80%, at least 85%, at least 90%, or at least 95% sequence identity or being identical to WFRQAPGKRREMVAA (SEQ ID NO: 100). Such an antibody of the invention may also comprise the FR2 sequence having at least 80%, at least 85%, at least 90%, or at least 95% sequence identity or being identical to WYRQAPGKRREMVAA (SEQ ID NO: 101).

An antibody of the invention preferably comprises a FR3 sequence having at least 80%, at least 85%, at least 90%, or at least 95% sequence identity or being identical to any one of SEQ ID NOs: 103-107. Such an antibody of the invention may comprise a FR3 sequence having at least 80%, at least 85%, at least 90%, or at least 95% sequence identity or being identical to the sequence MYRESVQGRFTISRDNAKRMVYLQMNSLRAEDTAVYYC (SEQ ID NO: 103). Such an antibody of the invention may comprise a FR3 sequence having at least 80%, at least 85%, at least 90%, or at least 95% sequence identity or being identical to the sequence MYRESVKGRFTISRDNAKRMVYLQMNSLRAEDTAVYYC (SEQ ID NO: 104). Such an antibody of the invention may comprise a FR3 sequence having at least 80%, at least 85%, at least 90%, or at least 95% sequence identity or being identical to the sequence YYRDSVKGRFTISRDNAKRMVYLQMNSLRAEDTAVYYC (SEQ ID NO: 105). Such an antibody of the invention may comprise a FR3 sequence having at least 80%, at least 85%, at least 90%, or at least 95% sequence or identity being identical to the sequence MYRESVKGRFTISRDNSKNTLYLQMNSLRAEDTAVYYC (SEQ ID NO: 106). Such an antibody of the invention may comprise a FR3 sequence having at least 80%, at least 85%, at least 90%, or at least 95% sequence identity or being identical to the sequence YYRDSVKGRFTISRDNSKNTLYLQMNSLRAEDTAVYYC (SEQ ID NO: 107).

An antibody of the invention preferably comprises FR1, FR2, FR3, and FR4 sequences, which each have at least 80%, at least 85%, at least 90%, or at least 95% sequence identity or are identical to the sequences set forth in SEQ ID NOs: 99, 100, 103, and 109, respectively.

An antibody of the invention preferably comprises FR1, FR2, FR3, and FR4 sequences, which each have at least 80%, at least 85%, at least 90%, or at least 95% sequence identity or are identical to the sequences set forth in SEQ ID NOs: 99, 101, 103, and 109, respectively.

An antibody of the invention preferably comprises FR1, FR2, FR3, and FR4 sequences, which each have at least 80%, at least 85%, at least 90%, or at least 95% sequence identity or are identical to the sequences set forth in SEQ ID NOs: 99, 101, 104, and 109, respectively.

An antibody of the invention preferably comprises FR1, FR2, FR3, and FR4 sequences, which each have at least 80%, at least 85%, at least 90%, or at least 95% sequence identity or are identical to the sequences set forth in SEQ ID NOs: 99, 101, 105, and 109, respectively.

An antibody of the invention preferably comprises FR1, FR2, FR3, and FR4 sequences, which each have at least 80%, at least 85%, at least 90%, or at least 95% sequence identity or are identical to the sequences set forth in SEQ ID NOs: 99, 101, 106, and 109, respectively.

An antibody of the invention preferably comprises FR1, FR2, FR3, and FR4 sequences, which each have at least 80%, at least 85%, at least 90%, or at least 95% sequence identity or are identical to the sequences of SEQ ID NOs: 99, 101, 107, and 109, respectively.

An antibody of the invention preferably comprises the CDR1, CDR2, and CDR3 sequences set forth in SEQ ID NO: 94, 97, and 98, and further comprises FR1, FR2, FR3, and FR4 sequences which each have at least 80%, at least 85%, at least 90%, or at least 95% sequence identity or are identical to the sequences set forth in SEQ ID NOs: 99, 102, 108, and 109, respectively.

An antibody of the invention preferably comprises the CDR1, CDR2, and CDR3 sequences set forth in SEQ ID NO: 94, 95, and 98, and further comprises FR1, FR2, FR3, and FR4 sequences which each have at least 80%, at least 85%, at least 90%, or at least 95% sequence identity or are identical to the sequences set forth in SEQ ID NOs: 99, 100, 103, and 109, respectively.

An antibody of the invention preferably comprises the CDR1, CDR2, and CDR3 sequences set forth in SEQ ID NO: 94, 95, and 98, and further comprises FR1, FR2, FR3, and FR4 sequences which each have at least 80%, at least 85%, at least 90%, or at least 95% sequence identity or are identical to the sequences set forth in SEQ ID NOs: 99, 101, 103, and 109, respectively.

An antibody of the invention preferably comprises the CDR1, CDR2, and CDR3 sequences set forth in SEQ ID NO: 94, 96, and 98, and further comprises FR1, FR2, FR3, and FR4 sequences which each have at least 80%, at least 85%, at least 90%, or at least 95% sequence identity or are identical to the sequences set forth in SEQ ID NOs: 99, 101, 103, and 109, respectively.

An antibody of the invention preferably comprises the CDR1, CDR2, and CDR3 sequences set forth in SEQ ID NO: 94, 95, and 98, and further comprises FR1, FR2, FR3, and FR4 sequences which each have at least 80%, at least 85%, at least 90%, or at least 95% sequence identity or are identical to the sequences set forth in SEQ ID NOs: 99, 101, 104, and 109, respectively.

An antibody of the invention preferably comprises the CDR1, CDR2, and CDR3 sequences set forth in SEQ ID NO: 94, 96, and 98, and further comprises FR1, FR2, FR3, and FR4 sequences which each have at least 80%, at least 85%, at least 90%, or at least 95% sequence identity or are identical to the sequences set forth in SEQ ID NOs: 99, 101, 104, and 109, respectively.

An antibody of the invention preferably comprises the CDR1, CDR2, and CDR3 sequences set forth in SEQ ID NO: 94, 96, and 98, and further comprises FR1, FR2, FR3, and FR4 sequences which each have at least 80%, at least 85%, at least 90%, or at least 95% sequence identity or are identical to the sequences set forth in SEQ ID NOs: 99, 101, 105, and 109, respectively.

An antibody of the invention preferably comprises the CDR1, CDR2, and CDR3 sequences set forth in SEQ ID NO: 94, 95, and 98, and further comprises FR1, FR2, FR3, and FR4 sequences which each have at least 80%, at least 85%, at least 90%, or at least 95% sequence identity or are identical to the sequences set forth in SEQ ID NOs: 99, 101, 106, and 109, respectively.

An antibody of the invention preferably comprises the CDR1, CDR2, and CDR3 sequences set forth in SEQ ID NO: 94, 96, and 98, and further comprises FR1, FR2, FR3, and FR4 sequences which each have at least 80%, at least 85%, at least 90%, or at least 95% sequence identity or are identical to the sequences set forth in SEQ ID NOs: 99, 101, 107, and 109, respectively.

Preferably, the framework sequence of the antibody is defined by the amino acid positions corresponding to positions 1-25, 39-53, 61-98, and 112-122 of SEQ ID NO: 1.

Preferably, the FR1, FR2, FR3, and/or FR4 regions of an antibody of the invention correspond to the amino acid positions 1-25, 39-53, 61-98, and 112-122 of SEQ ID NO: 1.

The antibody of the present invention is preferably humanized.

The term "humanization" as used herein refers to a process of modifying non-human antibodies, typically derived from animals, to maximize their amino acid sequence identity to the closest human equivalent. This alteration involves genetic engineering that retains the antibody's ability to recognize and bind to specific antigens while minimizing potential adverse reactions when administered to humans. Typically, degree of humanization of an antibody is defined as percent identity of V segment or framework regions with the human counterpart.

It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) Cancer Res 53:851-856. Riechmann, L., et al., (1988) Nature 332:323-327; Verhoeyen, M., et al., (1988) Science 239:1534-1536; Kettleborough, C. A., et al., (1991) Protein Engineering 4:773-3783; Maeda, H., et al., (1991) Human Antibodies Hybridoma 2:124-134; Gorman, S. D., et al., (1991) Proc Natl Acad Sci USA 88:4181-4185; Tempest, P. R., et al., (1991) Bio/Technology 9:266-271; Co, M. S., et al., (1991) Proc Natl Acad Sci USA 88:2869-2873; Carter, P., et al., (1992) Proc Natl Acad Sci USA 89:4285-4289; and Co, M. S. et al., (1992) J Immunol 148:1149-1154.

In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In the context of the present invention, in particular in the context of humanized versions of wtNbALFA, the term "humanized" preferably refers to an antibody that has higher degree of framework sequence identity to a given human germline sequence than wtNbALFA. The given human germline sequence is preferably the human germline sequence(s) that has the highest sequence identity to the framework regions of wtNbALFA. More preferably, the given human germline sequence is IGHV3-23*4 set forth in SEQ ID NO: 110 for the V segment and IGHJ6*01 for the J segment set forth in SEQ ID NO: 126.

The term "germline sequence" refers to an amino-acid sequence that represents the unaltered, naturally occurring protein derived from the genetic sequence present in the germ cells (sperm or egg cells) of an organism. This sequence serves as the baseline genetic information and the term "germline sequence" is used to distinguish the protein derived from the original genetic makeup and the protein comprising any modifications to the protein sequence (i.e., mutations), that might be introduced for specific purposes.

As used herein "framework identity" refers to the percentage identity of the germline-encoded framework of the closest human germline (e.g., IGHV3-23 or one of its allotypes) to the framework of the humanized or wtNbALFA to which it was compared. The frameworks are defined as described herein (SEQ ID NOs: 99-109). The alignment was calculated using the global alignment algorithm of Needleman and Wunsch, accessible via the Pairwise Sequence Alignment tool (https://www.ebi.ac.uk/Tools/psa/emboss_needle/). As MATRIX, the Blosum62 matrix was utilized with a GAP OPEN value of 10, a GAP EXTENDED value of 0.5, the END GAP PENALTY was set to false, an END GAP OPEN value of 0 and an END GAP EXTEND value of 0.5. These values represent the standard running parameters of the tool. After running the algorithm, the identity value was given. As used herein, an "overall framework identity" refers to the weighted average framework identity that is calculated as average identity of FR1 to FR4 normalized by the sequence length of the respective region (i.e., 25, 15, 38, and 11 amino acids for FR1, FR2, FR3, and FR4, respectively; see Table 3).

An antibody of the invention preferably comprises a sequence that has at least about 71%, at least about 75%, or preferably at least about 80%, overall framework identity to the closest human germline sequence(s). An antibody of the invention may even comprise a sequence that has at least about 85%, or at least about 90% overall framework identity to the closest human germline sequence(s). An antibody of the invention preferably comprises a sequence that has at least about 71%, at least about 75%, or preferably at least about 80% overall framework identity to the framework regions of IGHV3-23*4 as shown in SEQ ID NO: 110 (for FR1, FR2, and FR3) and IGHJ6*01 as shown in SEQ ID NO: 126 (for FR4). An antibody of the invention may even comprise a sequence that has at least about 85%, or at least about 90% overall framework identity to the framework regions of IGHV3-23*4 as shown in SEQ ID NO: 110 (for FR1, FR2, and FR3) and IGHJ6*01 as shown in SEQ ID NO:126 (for FR4).

As used herein "V segment identity" refers to the percentage identity of the germline-encoded FR1, CDR1, FR2, CDR2, FR3 of the closest human germline (e.g., IGHV3-23 or one of its allotypes) to the FR1, CDR1, FR2, CDR2, FR3 of the humanized or wtNbALFA to which it was compared. For this, the DomainGapAlign tool of IMGT was used (https://www.imgt.org/3Dstructure-DB/cgi/DomainGapAlign.cgi). The Domain type was set to "V", as species "any" or "*Homo sapiens* (human)" was chosen and the Smith-Waterman score was set to be above 0. The E values was chosen as 200, the Gap penalty for query was set to −5 and the Gap penalty for the reference was set to −20. These values represent the standard running parameters of the tool. The antibody sequence of interest was inserted in the FASTA format. The tool calculated the closest germline sequences and provided a "V-REGION identity percentage" value for each one of them. The "V-REGION identity percentage" of the closest related human sequence was reported as V segment identity herein.

An antibody of the invention preferably comprises a sequence that has at least about 60%, at least about 65% or preferably at least about 70% V segment identity to the closest human germline sequence. An antibody of the invention preferably comprises a sequence that has at least about 60%, at least about 65% or preferably at least about 70% V segment identity to IGHV3-23*4 as shown in SEQ ID NO: 110.

An antibody of the invention preferably has an affinity for the epitope tag shown in SEQ ID NO: 2 that is at least comparable with the affinity of the antibody of SEQ ID NO: 1. As used herein, "at least comparable" preferably means that the $K_D$ of a given antibody is not more than by about factor 2.5 higher than the $K_D$ of the reference antibody it is compared to, such as the antibody of SEQ ID NO: 1. The $K_D$ of a given antibody and the reference antibody is preferably measured using the same method. Any suitable method for determining the $K_D$ can be used in the art. Known methods for determining $K_D$ include, but are not limited to, e.g., ELISA, surface plasmon resonance (SPR), or biolayer interferometry (BLI). Preferably, the affinity is measured by biolayer interferometry, preferably by a method as essentially described in Method 1.

Preferably, an antibody of the invention has a $K_D$ for the epitope tag shown in SEQ ID NO: 2 that is not more than by about factor 2.5 higher than the $K_D$ of wtNbALFA for said epitope tag. More preferably, an antibody of the invention has a $K_D$ for the epitope tag shown in SEQ ID NO: 2 that is not more than by about factor 2 higher than the $K_D$ of wtNbALFA for said epitope tag. More preferably, an antibody of the invention has a $K_D$ for the epitope tag shown in SEQ ID NO: 2 that is not more than by about factor 1.5 higher than the $K_D$ of wtNbALFA for said epitope tag. More preferably, an antibody of the invention has a $K_D$ for the epitope tag shown in SEQ ID NO: 2 that is not more than by about factor 1.2 higher than the $K_D$ of wtNbALFA for said epitope tag.

An antibody of the invention may have a $K_D$ for the epitope tag shown in SEQ ID NO: 2, that is not higher than the $K_D$ of wtNbALFA for said epitope tag. Preferably, an antibody of the invention may have a $K_D$ for the epitope tag shown in SEQ ID NO: 2, that is lower than the $K_D$ of wtNbALFA for said epitope tag. Preferably, an antibody of the invention may have a $K_D$ for the epitope tag shown in SEQ ID NO: 2, that is at least by about factor 1.5 lower than the $K_D$ of wtNbALFA for said epitope tag. Preferably, an antibody of the invention may have a $K_D$ for the epitope tag shown in SEQ ID NO: 2, that is at least by about factor 2.0 lower than the $K_D$ of wtNbALFA for said epitope tag. Preferably, an antibody of the invention may have a $K_D$ for the epitope tag shown in SEQ ID NO: 2, that is at least by about factor 2.5 lower than the $K_D$ of wtNbALFA for said epitope tag.

An antibody of the invention may have a $K_D$ for the epitope tag shown in SEQ ID NO: 2 that is from about factor 2.5 higher to about factor 100 lower than the $K_D$ of wtNbALFA for said epitope tag. An antibody of the invention may have a $K_D$ for the epitope tag shown in SEQ ID NO: 2 that is from about factor 2.5 higher to about factor 50 lower than the $K_D$ of wtNbALFA for said epitope tag. An antibody of the invention may have a $K_D$ for the epitope tag shown in SEQ ID NO: 2 that is from about factor 2.5 higher to about factor 40 lower than the $K_D$ of wtNbALFA for said epitope tag. An antibody of the invention may have a $K_D$ for the epitope tag shown in SEQ ID NO: 2 that is from about factor 2.5 higher to about factor 30 lower than the $K_D$ of wtNbALFA for said epitope tag. An antibody of the invention may have a $K_D$ for the epitope tag shown in SEQ ID NO: 2 that is from about factor 2.5 higher to about factor 20 lower than the $K_D$ of wtNbALFA for said epitope tag. An antibody of the invention may have a $K_D$ for the epitope tag shown in SEQ ID NO: 2 that is from about factor 2.5 higher to about factor 15 lower than the $K_D$ of wtNbALFA for said epitope tag. An antibody of the invention may have a $K_D$ for the epitope tag shown in SEQ ID NO: 2 that is from about factor 2.5 higher to about factor 10 lower than the $K_D$ of wtNbALFA for said epitope tag. An antibody of the invention may have a $K_D$ for the epitope tag shown in SEQ ID NO: 2 that is from about factor 2.5 higher to about factor 5 lower than the $K_D$ of wtNbALFA for said epitope tag. An antibody of the invention may have a $K_D$ for the epitope tag shown in SEQ ID NO: 2 that is from about factor 2.5 higher to about factor 4 lower than the $K_D$ of wtNbALFA for said epitope tag. An antibody of the invention may have a $K_D$ for the epitope tag shown in SEQ ID NO: 2 that is from about factor 2.5 higher to about factor 3 lower than the $K_D$ of wtNbALFA for said epitope tag.

Preferably, an antibody of the invention has a $K_D$ for the epitope tag shown in SEQ ID NO: 2 that is not more than by about factor 2.5 higher than the $K_D$ of the antibody of SEQ ID NO: 121 for said epitope tag. More preferably, an antibody of the invention has a $K_D$ for the epitope tag shown in SEQ ID NO: 2 that is not more than by about factor 2 higher than the $K_D$ of the antibody of SEQ ID NO: 121 for said epitope tag. More preferably, an antibody of the invention has a $K_D$ for the epitope tag shown in SEQ ID NO: 2 that is not more than by about factor 1.5 higher than the $K_D$ of the antibody of SEQ ID NO: 121 for said epitope tag. More preferably, an antibody of the invention has a $K_D$ for the epitope tag shown in SEQ ID NO: 2 that is not more than by about factor 1.2 higher than the $K_D$ of the antibody of SEQ ID NO: 121 for said epitope tag. An antibody of the invention may have a $K_D$ for the epitope tag shown in SEQ ID NO: 2, that is not higher than the $K_D$ of the antibody of SEQ ID NO: 121 for said epitope tag.

An antibody of the invention may have a $K_D$ for the epitope tag shown in SEQ ID NO: 2 that is from about factor 2.5 higher to about factor 100 lower than the $K_D$ of the antibody set forth in SEQ ID NO: 121 for said epitope tag. An antibody of the invention may have a $K_D$ for the epitope tag shown in SEQ ID NO: 2 that is from about factor 2.5 higher to about factor 50 lower than the $K_D$ of the antibody set forth in SEQ ID NO: 121 for said epitope tag. An antibody of the invention may have a $K_D$ for the epitope tag shown in SEQ ID NO: 2 that is from about factor 2.5 higher to about factor 40 lower than the $K_D$ of the antibody set forth in SEQ ID NO: 121 for said epitope tag. An antibody of the invention may have a $K_D$ for the epitope tag shown in SEQ ID NO: 2 that is from about factor 2.5 higher to about factor 30 lower than the $K_D$ of the antibody set forth in SEQ ID NO: 121 for said epitope tag. An antibody of the invention may have a $K_D$ for the epitope tag shown in SEQ ID NO: 2 that is from about factor 2.5 higher to about factor 20 lower than the $K_D$ of the antibody set forth in SEQ ID NO: 121 for said epitope tag. An antibody of the invention may have a $K_D$ for the epitope tag shown in SEQ ID NO: 2 that is from about factor 2.5 higher to about factor 15 lower than the $K_D$ of the antibody set forth in SEQ ID NO: 121 for said epitope tag. An antibody of the invention may have a $K_D$ for the epitope tag shown in SEQ ID NO: 2 that is from about factor 2.5 higher to about factor 10 lower than the $K_D$ of the antibody set forth in SEQ ID NO: 121 for said epitope tag. An antibody of the invention may have a $K_D$ for the epitope tag shown in SEQ ID NO: 2 that is from about factor 2.5 higher to about factor 5 lower than the $K_D$ of the antibody set forth in SEQ ID NO: 121 for said epitope tag. An antibody of the invention may have a $K_D$ for the epitope tag shown in SEQ ID NO: 2 that is from about factor 2.5 higher to about factor 4 lower than the $K_D$ of the antibody set forth in SEQ ID NO: 121 for said epitope tag. An antibody of the invention may have a $K_D$ for the epitope tag shown in SEQ ID NO: 2 that is from about factor 2.5 higher to about factor 3 lower than the $K_D$ of the antibody set forth in SEQ ID NO: 121 for said epitope tag.

Preferably, an antibody of the invention has a $K_D$ for the epitope tag shown in SEQ ID NO: 2 that is not more than by about factor 2.5 higher than the $K_D$ of the antibody of SEQ ID NO: 123 for said epitope tag. More preferably, an antibody of the invention has a $K_D$ for the epitope tag shown in SEQ ID NO: 2 that is not more than by about factor 2 higher than the $K_D$ of the antibody of SEQ ID NO: 123 for said epitope tag. More preferably, an antibody of the invention has a $K_D$ for the epitope tag shown in SEQ ID NO: 2 that is not more than by about factor 1.5 higher than the $K_D$ of the antibody of SEQ ID NO: 123 for said epitope tag. More preferably, an antibody of the invention has a $K_D$ for the epitope tag shown in SEQ ID NO: 2 that is not more than by about factor 1.2 higher than the $K_D$ of the antibody of SEQ ID NO: 123 for said epitope tag. An antibody of the invention may have a $K_D$ for the epitope tag shown in SEQ ID NO: 2, that is not higher than the $K_D$ of the antibody of SEQ ID NO: 123 for said epitope tag.

An antibody of the invention may have a $K_D$ for the epitope tag shown in SEQ ID NO: 2 that is from about factor 2.5 higher to about factor 100 lower than the $K_D$ of the antibody set forth in SEQ ID NO: 123 for said epitope tag. An antibody of the invention may have a $K_D$ for the epitope tag shown in SEQ ID NO: 2 that is from about factor 2.5 higher to about factor 50 lower than the $K_D$ of the antibody set forth in SEQ ID NO: 123 for said epitope tag. An antibody of the invention may have a $K_D$ for the epitope tag shown in SEQ ID NO: 2 that is from about factor 2.5 higher to about factor 40 lower than the $K_D$ of the antibody set forth in SEQ ID NO: 123 for said epitope tag. An antibody of the invention may have a $K_D$ for the epitope tag shown in SEQ ID NO: 2 that is from about factor 2.5 higher to about factor 30 lower than the $K_D$ of the antibody set forth in SEQ ID NO: 123 for said epitope tag. An antibody of the invention may have a $K_D$ for the epitope tag shown in SEQ ID NO: 2 that is from about factor 2.5 higher to about factor 20 lower than the $K_D$ of the antibody set forth in SEQ ID NO: 123 for said epitope tag. An antibody of the invention may have a $K_D$ for the epitope tag shown in SEQ ID NO: 2 that is from about factor 2.5 higher to about factor 15 lower than the $K_D$ of the antibody set forth in SEQ ID NO: 123 for said epitope tag. An antibody of the invention may have a $K_D$ for the epitope tag shown in SEQ ID NO: 2 that is from about factor 2.5 higher to about factor 10 lower than the $K_D$ of the antibody set forth in SEQ ID NO: 123 for said epitope tag. An antibody of the invention may have a $K_D$ for the epitope tag shown in SEQ ID NO: 2 that is from about factor 2.5 higher to about factor 5 lower than the $K_D$ of the antibody set forth in SEQ ID NO: 123 for said epitope tag. An antibody of the invention may have a $K_D$ for the epitope tag shown in SEQ ID NO: 2 that is from about factor 2.5 higher to about factor 4 lower than the $K_D$ of the antibody set forth in SEQ ID NO: 123 for said epitope tag. An antibody of the invention may have a $K_D$ for the epitope tag shown in SEQ ID NO: 2 that is from about factor 2.5 higher to about factor 3 lower than the $K_D$ of the antibody set forth in SEQ ID NO: 123 for said epitope tag.

An antibody of the invention may have a $K_D$ for the epitope tag shown in SEQ ID NO: 2 of about $5\times10^{-10}$ M or lower, preferably $3\times10^{-10}$ M or lower, as preferably measured by biolayer interferometry, preferably by a method as essentially described in Method 1. An antibody of the invention may also have a $K_D$ for the epitope tag shown in SEQ ID NO: 2 of about $2\times10^{-10}$ M or lower or $2\times10^{-10}$ M or lower, as preferably measured by biolayer interferometry, preferably by a method as essentially described in Method 1.

An antibody of the invention preferably has a higher Tm as compared to the antibody of SEQ ID NO: 1.

The term "Tm" as used herein refers to the temperature at which half of all molecules are denatured and half of all molecules retain their conformation. For example, a Tm of 60° C. means that at this temperature, 50% of antibodies present in the sample are not denatured while the other 50% of antibodies is denatured. Tm can be measured as essentially described in Method 2.

An antibody of the invention preferably has a Tm of at least about 62° C., preferably at least about 63° C. The antibody of the invention may also have a Tm that is at least about 64° C., at least about 65° C. or even at least about 66° C. The Tm is preferably measured as essentially described in Method 2.

An antibody of the invention preferably comprises a protein A binding site.

As used herein, staphylococcal Protein A (SpA) or protein A refers to a molecule derived from the cell wall of the bacteria *Staphylococcus aureus* with a strong affinity to immunoglobulins, particularly human IgG. SpA's unique ability to specifically interact with the Fc region of antibodies offers significant potential for various biotechnological applications, including antibody purification, immobilization, and detection in diagnostic and therapeutic settings. SpA affinity purification is currently the most applied affinity system for antibody purification.

In the context of the present application, it is believed that up to 13 amino acid positions may be involved in the recognition of SpA: residues at positions corresponding to sequence positions 15, 17, 19, 60, 62, 67, 68, 69, 71, 73, 84, 86, and 87 of SEQ ID NO: 1. In particular, the residues Gly 15, Ser 17, Arg 19, Thr 60, Tyr 62, Lys 67, Gly 68, Arg 69, Thr 71, Ser 73, Gln 84, Asn 86, Ser 87 are important for SpA binding. The residues Gly 15, Ser 17, Arg 19, Tyr 62, Gly 68, Arg 69, Thr 71, Gln 84 are already present in wt NbALFA. The residues Ser 73, Asn 86, and Ser 87, are not comprised in wtALFA, but in all acceptor frameworks that are used for generating the CDR variants 1-7. Position 60, however, is located within the CDR2 region according to the present disclosure, whereas position 67 would be located within the CDR2 region, if determined according to Kabat. Since wt NbALFA comprises the residues Ala 60 and Gln 67, these two residues would have to be mutated to improve SpA binding. Although these two residues are within the CDR2 region or would be in the CDR2 region if determined according to Kabat, the inventors of the present application have surprisingly found that introducing the mutations Ala 60→Thr and/or Gln 67→Lys retains the high binding affinity to the epitope tag of SEQ ID NO: 2, as shown for variants 10-13 and 15. However, introducing the mutations Ala 60→Thr and/or Gln 67→Lys can promote SpA binding, as shown in Example 3 and Table 4.

An antibody of the invention may comprise a Thr residue at the position corresponding to sequence position 60 of SEQ ID NO: 1. An antibody of the invention may comprise a Lys residue at the position corresponding to sequence position 67 of SEQ ID NO: 1.

An antibody of the invention may comprise at positions corresponding to sequence positions 60 and 67 of SEQ ID NO: 1 the following amino acid residues: a Thr at position 60 and a Lys at position 67.

An antibody of the invention may comprise a Gly residue at the position corresponding to sequence position 15. An antibody of the invention may comprise a Ser residue at the position corresponding to sequence position 17. An antibody of the invention may comprise an Arg residue at the position corresponding to sequence position 19. An antibody of the invention may comprise a Tyr residue at the position corresponding to sequence position 62. An antibody of the invention may comprise a Gly residue at the position corresponding to sequence position 68. An antibody of the invention may comprise a Arg residue at the position corresponding to sequence position 69. An antibody of the invention may comprise a Thr residue at the position corresponding to sequence position 71. An antibody of the invention may comprise a Ser residue at the position corresponding to sequence position 73. An antibody of the invention may comprise a Gln residue at the position corresponding to sequence position 84. An antibody of the invention may comprise an Asn residue at the position corresponding to sequence position 86. An antibody of the invention may comprise a Ser residue at the position corresponding to sequence position 87.

An antibody of the invention may comprise at positions corresponding to sequence positions 15, 17, 19, 62, 68, 69, 71, 73, 84, 86, 87 of SEQ ID NO: 1, at least 1, at least 2, at least 3, at least 4, at least 5, at least 6, at least 7, at least 8, at least 9, at least 10, or preferably all of the following amino acid residues: a Gly at position 15, Ser at position 17, Arg at position 19, Tyr at position 62, Gly at position 68, Arg at position 69, Thr at position 71, Ser at position 73, Gln at position 84, Asn at position 86, and Ser at position 87.

An antibody of the invention may comprise at positions corresponding to sequence positions 15, 17, 19, 60, 62, 67, 68, 69, 71, 73, 84, 86, 87 of SEQ ID NO: 1, at least 1, at least 2, at least 3, at least 4, at least 5, at least 6, at least 7, at least 8, at least 9, at least 10, at least 11, at least 12, or preferably all of the following amino acid residues: a Gly at position 15, Ser at position 17, Arg at position 19, a Thr at position 60, Tyr at position 62, Lys at position 67, Gly at position 68, Arg at position 69, Thr at position 71, Ser at position 73, Gln at position 84, Asn at position 86, and Ser at position 87.

An antibody of the invention preferably does not comprise a N×T/S motif, for example an NXT motif, for example an NKT motif. Said N×T/S motif is a classical glycosylation site. Glycosylation is often undesired due to its heterogeneity and consequently this renders a glycosylated antibody less interesting in particular for in vivo applications, such as therapeutic applications. The reference antibody of SEQ ID NO: 129 comprises an NKT motif at amino acid positions 78-80. As shown in Example 5, glycosylation was observed for SEQ ID NO: 129, while no glycosylation was observed for wild type and humanized NbALFA versions that do not comprise an N×T/S motif.

An antibody of the invention may be conjugated to a detectable label.

The term "detectable label" generally refers to any appropriate chemical substance or enzyme, which directly or indirectly generates a detectable compound or signal in a chemical, physical, optical, or enzymatic reaction. For example, a fluorescent or radioactive label can be conjugated to the antibody to generate fluorescence or X-rays as detectable signal. Alkaline phosphatase, horseradish peroxidase and B-galactosidase are examples of enzyme labels (and at the same time optical labels), which catalyze the formation of chromogenic reaction products. The detectable label refers to detectable entities that can be used for the detection of the target of interest such as in microscopy, immunohistochemistry, flow cytometry, or in vivo application, such as in vivo imaging. Preferably, the label does not negatively affect the characteristics of the antibody to which the label is conjugated. There are many types of detectable labels, including a fluorescent label, a chromophore label, an isotope label, a metal label, and a radioactive label. The presence of the peptide of SEQ ID NO: 2 may be detected by contacting the fusion protein with an antibody of the invention conjugated to a detectable label and detecting the signal of the detectable label. Non-exhaustive examples for a suitable chromophore label are alkaline phosphatase or peroxidase exposed to TMB (3,3',5,5' tetramethylbenzidine), DAB (3,3',4,4' diaminobenzidine), and 4CN (4-chloro-1-naphthol). ABTS (2,2'-azino-di [3-ethyl-benzthiazoline] sulfonate), OPD (o-phenylenediamine), and to BCIP/NBT (5-bromo-4-chloro-3-indolyl-phosphate/nitroblue tetrazolium). Non-exhaustive examples for isotope labels are 13C, 15N, 19F, 27Al, 11B, 1271 or different Lanthanides isotopes. Non-exhaustive examples for a metal label are Au, Pd, Pb, Pt Ag, Hg and Os. The label may be a direct label, i.e. a label that is directly detectable. Alternatively, the label may be an indirect label, i.e. a label which is an affinity tag (or epitope tag) that can be specifically bound by another specific binding partner that is conjugated to another detectable label, such as a fluorescent or chromophore label. Examples of suitable epitope tags include, but are not limited to, FLAG-tag, Strep-tag, Myc-tag, HA-tag, VSV-G-tag, HSV-tag, V5-tag, SPOT-tag, BC2 tag, and EPEA tag. The antigen may also be a protein, for example, glutathione-S-transferase (GST), maltose binding protein (MBP), chitin binding protein (CBP) or thioredoxin as an antigen.

According to further embodiments of the invention, the detectable label can be a fluorescent label. Examples of fluorescent labels are phycoerythrin, allophycocyanin (APC), Brilliant Violet 421, Alexa Fluor 488, coumarin or rhodamines to name only a few. Detection of a fluorescent label means detection of emitted light upon excitation of the fluorescent label. Non-exhaustive examples for suitable fluorescent labels are "green" emitters (Atto488, Alexa488, Cy2, etc.), "orange" emitters (Atto542, alexa555, Cy3, etc.), "Red-far-Red" emitters (Alexa633, Atto 647N, Cy5, etc.), infrared emitters (Atto 700, LiCor IRDye700, LiCor IRDye800, etc.), ultra-violet absorbing fluorescent dyes (Atto390 or Alexa405). A fluorescent label may also be a fluorescent protein, such as GFP, eGFP, YFP, RFP, CFP, BFP, mCherry, or near-infrared fluorescent proteins.

According to further embodiments of the invention, the detectable label can be an affinity tag.

The term "affinity tag" refers to a stretch of amino acids that can be specifically bound by another specific binding partner that is conjugated to another detectable label, such as a fluorescent or chromophore label. In such a case, detection of the detectable label attached to the antibody of the invention may be conducted by contacting the antibody with a specific binding partner that specifically binds to the detectable label conjugated to the antibody of the invention. The specific binding partner may be labeled with a further detectable label that can preferably be distinguished from the first detectable label, such as a fluorescent or chromophore label. The specific binding partner may however be a structure, which can be recognized by another specific (labeled) binding reagent. For example, the specific binding partner that binds to the detectable label conjugated to the antibody of the invention may be a (primary) antibody, which may be specifically recognized by a (secondary) antibody, which carries a detectable label that is preferably distinguishable from the first detectable label, such as a fluorescent label. The method of detecting the fusion protein may thus comprise the step of contacting the fusion protein and the antibody of the invention with a specific binding partner for the detectable label comprised in the antibody of the invention. Where a second detectable label is present, the method may comprise the step of detecting the first and/or the second detectable label.

According to methods where the detectable label conjugated to the antibody of the invention is an affinity tag, the method of detecting the fusion protein may comprise, in a first step, contacting the antibody of the invention with a sample comprising or suspected to comprise the fusion protein comprising the peptide. In a second step, a (secondary) specific binding partner can be contacted with the sample comprising the fusion protein bound to the antibody of the invention. In cases where the (secondary) specific binding partner is not conjugated to a detectable label or where the detectable label is an affinity tag, the method may further comprise the step of contacting a further specific binding partner, such as a further antibody that specifically binds to the (secondary) specific binding partner or its detectable label. The further specific binding partner may comprise a detectable label, such as a fluorescent label that can be used for detection of the fusion protein. Presence, amount and/or localization of the tagged polypeptide or protein can be detected or determined by measuring or observing a reporter signal obtained from a detectable label comprised in the (secondary) specific binding partner or further specific binding partner.

The present invention relates to a protein comprising the amino acid sequence of the antibody of the invention. The protein may be a fusion protein comprising the antibody of the invention and another protein.

The term "protein" as used herein comprises one or more polypeptides. The term "fusion protein" as used herein refers to a polypeptide or protein comprising two or more subunits. At least one of the subunits is preferably a protein or polypeptide. Within the fusion protein, these subunits may be linked by covalent or non-covalent linkage. Preferably, the fusion protein is a translational fusion between the two or more subunits. The translational fusion may be generated by genetically engineering the coding nucleotide sequence for one subunit in a reading frame with the coding nucleotide sequence of a further subunit. Subunits may be interspersed by a linker. If one or more of the subunits is part of a protein (complex) that consists of more than one polypeptide chain, the term "fusion protein" may also refer to the protein comprising the fused sequences and all other polypeptide chain(s) of the protein (complex).

The term "polypeptide" as used herein usually refers to a peptide having at least about 30, at least about 40, or at least about 50 amino acids.

The term "peptide" as used herein refers to a linear series of amino acids connected one to the other preferably by peptide bonds between the alpha-amino and carboxy groups of adjacent residues. As used herein the term "amino acid" refers to either natural and/or unnatural or synthetic amino acids, including glycine and both the D or L optical isomers, and amino acid analogs and peptidomimetics, with proteogenic amino acids being preferred. A "proteinogenic amino acid" is an amino acid that can be incorporated biosynthetically into proteins during translation. Currently, there are 22 known genetically encoded (proteinogenic) amino acids, 20 in the standard genetic code and an additional 2 that can be incorporated by special translation mechanisms. The "peptide" as used herein preferably comprises no more than about 50 amino acids.

The present invention relates to a complex comprising a protein comprising the amino acid sequence of X1-X2-L-E-X5-E-X7-R-R-R-L-X12-X13 (SEQ ID NO: 3), wherein X1 is G or S or P or T, X2 is R or G or P, X5 is E or Q, X7 is L or I, X12 is S or T or P or A or D or E, and wherein X13 is Por A or S or K or D or E or no amino acid, and an antibody of the invention. Accordingly, an antibody of the invention may be in complex with an epitope it specifically binds to. Such an epitope may be the epitope tag as described herein or a peptide set forth in any one of SEQ ID NOs: 2-93. Preferably, the protein comprises the amino acid sequence of SEQ ID NO: 2.

The present invention also relates to a nucleic acid encoding an antibody of the invention as described herein. The nucleic acid molecule may allow expression of the antibody. It may include sequence elements that contain information regarding transcriptional and/or translational regulation, and such sequences may be "operably linked" to the nucleotide sequence encoding the protein. An operable linkage is a linkage in which the regulatory sequence elements and the sequence to be expressed are connected in a way that enables gene expression. The precise nature of the regulatory regions necessary for gene expression may vary among species, but in general these regions include a promoter, which, in prokaryotes, contains both the promoter per se, i.e., DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native protein to a specific compartment of a host cell.

The nucleic acid encoding an antibody of the invention may be a DNA.

Alternatively, the nucleic acid encoding an antibody of the invention may be an RNA, such as an mRNA.

The present invention relates to a vector comprising the nucleic acid encoding the antibody of the invention. Thus, the nucleic acid molecules of the invention may be part of a vector or any other kind of cloning or expression vehicle. Such a vehicle described herein may include, aside from the regulatory sequences described herein and a nucleic acid sequence encoding a peptide or protein described herein, replication and control sequences derived from a species compatible with a host cell that is used for expression as well as selection markers conferring a selectable phenotype on transformed or transfected cells. Large numbers of suitable cloning vectors are known in the art and are commercially available, such as a plasmid, a phagemid, a phage, a baculovirus, a cosmid or an artificial chromosome.

The present invention further relates to a host cell comprising the nucleic acid of the invention or the vector of the invention, or a host cell expressing the antibody of the invention. Thus, cloning or expression of nucleic acid molecule or the vector of the invention can be conducted at least partially using host cells transformed with the nucleic acid or vector, or to which the nucleic acid molecule or vector has been transferred by other means including transduction or transfection. Transfer of DNA can be performed using standard techniques.

A host cell of the invention can be prokaryotic or eukaryotic. Prokaryotic host cells include bacterial cells such as *Escherichia coli* (*E. coli*) or *Bacillus subtilis*. Eukaryotic may be microbial cells, such as yeast cells, such as *Saccharomyces cerevisiae, Pichia pastoris*, plant cells, or animal cells, such as insect cells, such as SF9 or High5 insect cells, avian cells, or mammalian cells. Mammalian cells may be derived from any species, such as mouse, rat, rabbit, monkey, ape, or human. In some embodiments, the host cell is a non-human host cell. A host cell may be an immortalized mammalian cell lines (e.g., HeLa cells or CHO cells) or a primary mammalian cell. A host cell of the invention is preferably an isolated host cell.

The present invention also relates to a method of producing antibody of the invention. The antibody according to the invention may be produced using any known and well-established method, including the use of well-established expression systems and/or recombinant cell culturing technology. The method can be carried out in vivo, the antibody can for example be produced in a bacterial or eukaryotic host organism and then isolated from this host organism or its culture. It is also possible to produce a protein in vitro, for example by use of an in vitro translation system.

When producing the antibody in vivo a nucleic acid encoding such antibody introduced into a suitable bacterial or eukaryotic host organism by means of recombinant DNA technology (as already outlined above). For this purpose, the host cell is first transformed with a cloning vector that includes a nucleic acid molecule encoding antibody as described herein using established standard methods. The host cell is then cultured under conditions, which allow expression of the heterologous DNA and thus the synthesis of the corresponding polypeptide. Subsequently, the antibody may be recovered either from the cell or from the cultivation medium.

Accordingly, a method of producing the antibody of the invention may comprise the step of cultivating a host cell as disclosed herein under conditions allowing the expression of the antibody of the invention. The method may further comprise recovering and/or isolating the antibody from the cell or from the cultivation medium.

An antibody of the present invention may be produced in transgenic organisms such as a goat or a plant. An antibody may also be produced by chemical synthesis.

The present invention relates to use of the antibody of the invention for the binding, detection, immobilization, isolation, or purification of a protein comprising the amino acid sequence of X1-X2-L-E-X 5-E-X7-R-R-R-L-X12-X13 (SEQ ID NO: 3), wherein X1 is G or S or P or T, X2 is R or G or P, X5 is E or Q, X7 is L or I, X12 is S or T or P or A or D or E, and wherein X13 is P or A or S or K or D or E or no amino acid. Preferably, the protein comprises the amino acid sequence of SEQ ID NO: 2.

The present invention also relates to antibody of the invention for use in the binding, detection, immobilization, isolation, or purification of a protein comprising the amino acid sequence of X1-X2-L-E-X5-E-X7-R-R-R-L-X12-X13 (SEQ ID NO: 3), wherein X1 is G or S or P or T, X2 is R or G or P, X5 is E or Q, X7 is L or I, X12 is S or T or P or A or D or E, and wherein X13 is P or A or S or K or D or E or no amino acid. Preferably, the protein comprises the amino acid sequence of SEQ ID NO: 2.

The present invention also relates to a method of binding or detecting a protein comprising the amino acid sequence of X1-X2-L-E-X5-E-X7-R-R-R-L-X12-X13 (SEQ ID NO: 3), wherein X1 is G or S or P or T, X2 is R or G or P, X5 is E or Q, X7 is L or I, X12 is S or T or P or A or D or E, and wherein X13 is P or A or S or K or D or E or no amino acid, comprising contacting the protein with an antibody of the invention and optionally detecting the antibody or a label comprised in the antibody. Preferably, the protein comprises the amino acid sequence of SEQ ID NO: 2.

SEQ ID NO: 3 defines the core structure of a peptide that can be bound by the antibody of the invention, which may further comprise up to two additional amino acids at the N terminus and up to two additional amino acids at the C terminus. Such additional amino acids at the ends of the core structure of the peptide usually do not necessarily influence the secondary structure of the of the peptide or specific binding of the peptide to an antibody specific for the peptide, but may serve as linker structures in the fusion protein. Accordingly, type and number of the additional amino acids may depend on the location of the peptide in the fusion protein and may vary depending on whether the peptide is located on N-terminus or C-terminus or somewhere in between of the polypeptide. Accordingly, the peptide sequence may comprise N-terminal of X1 the amino acids Xa-Xb, wherein Xa is D or S or G or M or P or no amino acid and Xb is S or D or P or M or R or G no amino acid. The peptide may also comprise C-terminal of X13 the amino acids Xy-Xz, wherein Xy is G or S or P or D or A or E or K or no amino acid, and Xz is S or P or no amino acid.

Detection can be optical detection, isotopic detection, or detection by electron microscopy. The method comprises contacting a protein comprising the amino acid sequence of SEQ ID NO: 2 or a variant sequence thereof, such as any one of SEQ ID NOs: 3-93 with an antibody of the invention, preferably under conditions allowing the formation of a complex between said protein and the antibody. The antibody of the invention may carry a detectable label as defined herein. Where the detectable label is a fluorescent label, chromophore label, isotope label, or metal label attached to it, it is understood that the antibody preferably has a defined number of labels attached to it. The method may comprise the step of detecting the detectable label. The method may comprise expressing the fusion protein comprising the peptide prior to contacting the fusion protein with the antibody of the invention.

The term "detection" as used herein includes both direct detection of a target (i.e. wherein the target is detected by a signal deriving from a target) and indirect detection of a target (i.e. wherein the target is detected by a signal that does not directly derive from the target, e.g. by a signal that derives from another molecule attached to the target). The term "detection" as used herein further includes both qualitative and quantitative detection. The term "detection" may refer to determination of the presence, subcellular localization, or amount of a given molecule or structure, such as a protein comprising the amino acid sequence of SEQ ID NO: 2 or a variant sequence thereof, such as any one of SEQ ID NOs: 3-93. Such protein to be detected, located and/or quantified can be detected at its intracellular location in a host cell, for example in the cell nucleus, in cell membranes or another cell compartment. The protein to be detected, and/or to be quantified can also be detected in a solution comprising said protein, for example a cell lysate obtained from a host cell or a tissue comprising the host cell.

The term "optical", as used herein, preferably refers to visible light but is generally not limited to it. The term may also refer to infrared, ultraviolet and other regions of the electromagnetic spectrum.

As used herein, "isotopic detection" relates to the detection of a molecule in which one or more atoms have been replaced (i.e., "labeled") with another isotope that commonly has a detectable variation. The isotopic label can be detected by multiple means, such as their mass (e.g. by mass spectrometry, matrix-assisted laser desorption/ionization (MALDI), desorption electrospray ionization (DESI), laser-ablation inductively coupled plasma mass spectrometry (LA-ICP-MS), or secondary-ion mass spectrometry (SIMS), vibrational mode (e.g. by infrared spectroscopy), gyromagnetic ratios (e.g. by nuclear magnetic resonance), or radioactive decay (e.g. an ionization chamber or autoradiographs of gels).

Electron microscopy relates to a method of detection using an electron microscope. Types of electron microscopes include transmission electron microscope (TEM), scanning electron microscope (SEM), reflection electron microscope (REM), scanning transmission electron microscope (STEM), and Correlative Light and Electron Microscopy (CLEM).

In a first step of a detection method, an antibody of the invention specifically binding the peptide comprised in the fusion protein may be contacted with a sample comprising the fusion protein. The sample may be a host cell, a tissue, a solution comprising cell lysate of a host cell or any other sample that comprises the fusion protein, such as a supernatant, as obtained after centrifugation of a liquid comprising the host cell, wherein the host cell is capable of secreting the polypeptide of interest into the liquid or another specimen like a body fluid.

This contacting step is preferably carried out at conditions that allow specific interaction of the antibody and the protein comprising the sequence the antibody specifically binds to. Such conditions are well known to the person of skill in the art. Washing steps typically follow the contacting step of an antibody to its antigen, and the skilled person knows how and when to apply said washing steps. Upon contacting with the sample, the antibody will specifically interact with the fusion protein. This interaction can be detected, monitored and quantified by measuring or observing the reporter signal obtained from the detectable label. For example, if the detectable label is a fluorescent label, fluorescence can be measured and observed upon excitation.

An advantage of a two-step detection method using two types of binding partners is that the tag-specific interaction is separated from the actual detection step. This allows that the antibody of the invention remains unchanged, as it does not need to comprise an additional detectable moiety. This may in some cases enhance its specificity or affinity compared to an antibody comprising an additional detectable label, as the detectable label could in some cases influence the interaction of the peptide comprised in the fusion protein of the invention and the antibody of the invention. Thus, the reliability and efficiency of the detection method could be enhanced in some cases. Furthermore, using the antibody of the invention simply as a capture antibody and not as a capture and detection antibody, allows separation of the capture and the detection steps if only presence and amount of the protein is to be determined. Therefore, the first step using the antibody of the invention could be followed by an isolation or enrichment step, yielding the captured protein of interest. The detection step could then be carried out on the isolated and/or enriched protein, leading to an enhanced reliability of the obtained quantification and an easier handling of the detection step.

Suitable biophysical or biomolecular detection methods for qualitatively detecting an epitope tag/antibody interaction comprise any suitable method known in the art. Such methods include, without being limited thereto, methods as applied for qualitative or quantitative assays, e.g. for Enzyme-linked Immunosorbent Assay (ELISA), ELISPOT assay, Western Blot, or immunoassays. Such methods comprise e.g. optical, radioactive or chromatographic methods, preferably when using any of the above labels, markers or linkers, more preferably fluorescence detection methods, radioactivity detection methods, Coomassie-Blue staining, silver staining or other protein staining methods, electron microscopy methods, methods for staining tissue sections by immunohistochemistry or by direct or indirect immunofluorescence, etc. Such methods may be applied either with the antibody or may involve the use of further tools, e.g. the use of a secondary binding partner, specifically binding to a part of the fusion protein, the antibody of the invention, or the complex.

In some embodiments, the subcellular localization of the tagged polypeptide or protein of interest can also be determined. For example, distinct subcellular structures such as the intermediate filamentous network or an essential part of the replication machinery can be visualized and monitored.

Detection of the fusion protein can also be carried out using an antibody of the invention that is an intrabody. An "intrabody" as used herein refers to an antibody that is located within a cell to bind to an intracellular protein. Due to the lack of a reliable mechanism for bringing an antibody into a living cell from the extracellular environment, this typically requires the expression of the antibody within the target cell. After expression, the antibody may remain in the cytoplasm, or it may have a nuclear localization signal, or it may undergo co-translational translocation across the membrane into the lumen of the endoplasmic reticulum, provided that it is retained in that compartment through a KDEL sequence. A detectable label conjugated to an intrabody may be a proteinaceous label, which can be expressed as fusion protein with the intrabody. Ideally, such a label may be optically detectable, such as by fluorescence. The detectable label may thus be a fluorescent protein.

The term "immobilization" or in the context of the present invention refers to conjugation of an antibody of the invention to a solid support, which may be any type of carrier material that can be used for immobilization of affinity ligands such as antibodies or parts thereof and it can refer to material in particulate (e. g. beads or granules, generally used in extraction columns) or in sheet form (e. g. membranes or filters, glass or plastic slides, microtiter assay plates, dipstick, capillary fill devices or such like) which can be flat, pleated, or hollow fibers or tubes. Suitable and well-known matrices without being exhaustive: are silica (porous amorphous silica), agarose or polyacrylamide supports, or macroporous polymers. Examples include dextran, collagen, polystyrene, polypropylene, polyvinylchloride, polyacrylamide, methacrylate, celluloses, calcium alginate, controlled pore glass, aluminum, titanium and porous ceramics, synthetic polymers and co-polymers, latex, silica, agarose, metal, glass, and carbon. Alternatively, the solid surface may comprise part of a mass dependent sensor, for example, a surface plasmon resonance detector. A solid support can also be a magnetic bead or polymeric bead or a chromatographic stationary phase.

The use of an antibody of the present invention for isolation and/or purification can be used in solution or immobilized. To immobilize the antibody, the antibody can be bound to a sample carrier, solid support, or matrix. This immobilization step can occur prior to or after the binding of the antibody to the peptide comprised in the fusion protein. Methods for immobilizing antibodies and parts thereof are well-known to the person skilled in the art and any method that allows immobilization without impairing binding properties can be used.

If the antibody of the present invention is not immobilized to a solid support, then the method may comprise a further step of isolating the complex, for example by using a specific binding partner for the complex, such as a secondary antibody that is specific for example for the complex or for the antibody or for a detectable label, such as an affinity tag, that is conjugated to the antibody. The secondary binding partner can be in solution or can be immobilized or immobilizable to a solid support.

In an optional further step following the capture step, the solid support comprising the immobilized antibody bound to the protein is washed to remove unbound and unspecifically bound constituents.

Optionally, in a further step, the protein can be eluted to obtain the isolated protein. Elution of the protein bound to the immobilized antibody can be achieved by methods known in the art. For example, the protein can be eluted by competitive elution with an epitope peptide as described herein in isolated form. This isolated epitope peptide will then be in competition with the protein to bind the immobilized tag-specific antibody. If the isolated peptide is added in surplus concentration, the reaction balance of the binding will be shifted to the binding of the immobilized antibody with the isolated epitope tag. This results in the release of the protein. The epitope peptide used for elution may be the same epitope peptide that is comprised in the protein. The epitope peptide used for elution may also be a different peptide than the epitope peptide comprised in the protein. If the epitope peptide used for elution is a different one, it is preferred that the epitope peptide used for elution has a higher binding affinity to the antibody than the epitope peptide comprised in the protein. Additional steps for further purifying the released polypeptide can optionally be added, such as method steps well-known to the skilled person.

The protein may also remain immobilized to the solid support, such as (magnetic) beads, and processed further in downstream application such as mass spectrometry, without the elution step.

The protein may comprise a linker with a cleavage site that can be cleaved with an appropriate means, for example a protease, to remove the peptide. Thereby the polypeptide of the protein may be released from the immobilized antibody, and the polypeptide can be obtained in its native form. For this embodiment, the nucleic acid sequence encoding the protein should not only comprise a sequence encoding the epitope tag but also a sequence encoding a linker with a breakable site, for example a cleavage site recognized by a protease. The release step by enzymatic cleave can replace or follow the elution step.

The peptide sequence comprised in protein that is comprised in the complex of the invention, or that is to be bound, detected, immobilized, isolated, or purified in the use of the invention, or that is to be bound or detected in the method of binding or detection of the present invention, preferably comprises the sequence of X1-X2-L-E-X5-E-L-R-R-R-L-X12-X13 (SEQ ID NO: 4), wherein X1 is S or T, X2 is R or G, X5 is E or Q, X12 is T or D or E, and wherein X13 is A or D or E or no amino acid. The peptide may comprise the sequence of S-R-L-E-E-E-L-R-R-R-L-T-E (SEQ ID NO: 2) or a variant thereof, wherein the variant has as compared to SEQ ID NO: 3 1 to 5 mutations selected from the group consisting of: S1→T, R2→G, E5→Q, T12→D, and T12→E, E13→A, E13→D, and deletion of E13. The variant may have as compared to SEQ ID NO: 3 following mutations: (a) S1→T and E13→A; (b) R2→G; (c) R2→G and E5→Q; (d) R2→G, E5→Q and E13→A; (e) R2→G, E5→Q, and T12→D, and E13→A; (f) R2→G, E5→Q, and T12→E, and E13→A; (g) T12→D and E13→A; (h) T12→E and E13→A; (i) and E13→A; (j) and E13→D; or (k) deletion of E13. A peptide comprising as a core structure the sequence SEQ ID NO: 4 may comprise N-terminal of X1 the amino acids Xa-Xb, wherein Xa is S or G or M or P or no amino acid, and Xb is R or G or S or P or M or no amino acid. Xa-Xb may be selected from the group consisting of P, M-P, G-R, P-G, P-S, S-P, G-P, S-P, M, and M-S, preferably P or M-P. Such a peptide may also comprise C-terminal of X13 the amino acids Xy-Xz, wherein is P or D or A or no amino acid, and Xz is P or S or no amino acid. Xy-Xz may be selected from the group consisting of no amino acid, P, D-P, A, and A-S, preferably no amino acid or P. The peptide may comprise a combination of Xa-Xb and Xy-Xz selected from the group consisting of: (a) M-P and P; (b) P and P; and (c) P and no amino acid.

The peptide sequence comprised in protein that is comprised in the complex of the invention, or that is to be bound, detected, immobilized, isolated, or purified in the use of the invention, or that is to be bound or detected in the method of binding or detection of the present invention, preferably comprises the sequence of SRLEEELRRRLTE (SEQ ID NO: 2).

The peptide sequence comprised in protein that is comprised in the complex of the invention, or that is to be bound, detected, immobilized, isolated, or purified in the use of the invention, or that is to be bound or detected in the method of binding or detection of the present invention, may comprise a sequence selected from the group consisting of:

(a) (SEQ ID NO: 5)
MPSRLEEELRRRLTEP;

(b) (SEQ ID NO: 6)
PSRLEEELRRRLTEP;

(c) (SEQ ID NO: 7)
PSRLEEELRRRLTE;

(d) (SEQ ID NO: 8)
GRSRLEEELRRRLTA;

(e) (SEQ ID NO: 9)
PGSRLEEELRRRLTAP;

(f) (SEQ ID NO: 10)
PSTRLEEELRRRLTAP;

(g) (SEQ ID NO: 11)
SPSRLEEELRRRLTAP;

(h) (SEQ ID NO: 12)
SPSRLEEELRRRLDAP;

-continued (i) (SEQ ID NO: 13)
SPSRLEEELRRRLEAP;

(j) (SEQ ID NO: 14)
SPSRLEEELRRRLTDP;

(k) (SEQ ID NO: 15)
SPSRLEEELRRRLTEP;

(l) (SEQ ID NO: 16)
SPSRLEEELRRRLTADP;

(m) (SEQ ID NO: 17)
SPSGLEEELRRRLTEP;

(n) (SEQ ID NO: 18)
GPSRLEEELRRRLT;

(o) (SEQ ID NO: 19)
GPSRLEEELRRRLTA;

(p) (SEQ ID NO: 20)
GPSRLEEELRRRLTAA;

(q) (SEQ ID NO: 21)
GPSRLEEELRRRLTAAS;

(r) (SEQ ID NO: 22)
SPSGLEQELRRRLTAP;

(s) (SEQ ID NO: 23)
SPSGLEQELRRRLDAP;

(t) (SEQ ID NO: 24)
SPSGLEQELRRRLEAP;

(u) (SEQ ID NO: 25)
SPSGLEQELRRRLTEP;

(v) (SEQ ID NO: 26)
GPSRLEEELRRRLTAP;

(w) (SEQ ID NO: 27)
GPSRLEEELRRRLTEP;

(x) (SEQ ID NO: 28)
GPSRLEEELRRRLTE;

(y) (SEQ ID NO: 29)
MSRLEEELRRRLTEP;
and (z) (SEQ ID NO: 30)
MSSRLEEELRRRLTEP.

The peptide sequence comprised in protein that is comprised in the complex of the invention, or that is to be bound, detected, immobilized, isolated, or purified in the use of the invention, or that is to be bound or detected in the method of binding or detection of the present invention, may comprise the sequence of X1-X2-L-E-X5-E-X7-R-R-R-L-X12-X13 (SEQ ID NO: 31), wherein X1 is G or S or P, X2 is R or G, X5 is E or Q, X7 is L or I, X12 is S or T or P or A, and X13 is P or A or S or no amino acid.

The peptide sequence comprised in protein that is comprised in the complex of the invention, or that is to be bound, detected, immobilized, isolated, or purified in the use of the invention, or that is to be bound or detected in the method of binding or detection of the present invention, may comprise the sequence of G-R-L-E-E-E-L-R-R-R-L-S(SEQ ID NO: 32) or a variant thereof, wherein the variant has as compared to SEQ ID NO: 32 1 to 6 mutations selected from the group consisting of: G1→S, G1→P, R2→G, E5→Q, L7→I, S12→T, S12→P, S12→A, addition of P13, addition of A13, and addition of S13. The variant may have as compared to SEQ ID NO: 32 following mutations: (a) G1→S, R2→G, E5→Q, and addition of P13; (b) R2→G, E5→Q, S12→T, and addition of A13; (c) G1→P, R2→G, E5→Q, S12→T, and addition of A13; (d) G1→S, R2→G, E5→Q, S12→T, and addition of P13; (e) G1→S, R2→G, S12→T, and addition of A13; (f) G1→S, R2→G, E5→Q, and S12→T; (g) G1→S, R2→G, E5→Q, S12→T, and addition of A13; (h) G1→S and S12→P, and addition of P13; (i) G1→S, R2→G, E5→Q, S12→T, and addition of P13; (j) E5→Q L7→I, and addition of P13; (k) addition of P13; or (1) S12→A. A peptide comprising as a core structure the sequence SEQ ID NO: 31 may comprise N-terminal of X1 the amino acids Xa-Xb, wherein Xa is M or S or P or D or G or no amino acid, and Xb is S or D or P or no amino acid. Xa-Xb may be selected from the group consisting of M-S, S-D, P-D, P-S, D-S, S-P, and G-P, preferably M-S. Such a peptide may also comprise C-terminal of X13 the amino acids Xy-Xz, wherein Xy is G or P or A or E or K or S or no amino acid, and Xz is P or S or no amino acid. Xy-Xz may be selected from the group consisting of no amino acid, G, P, A, E-P, A-S, K, and S, preferably no amino acid. The peptide may comprise a combination of Xa-Xb and Xy-Xz that is M-S and no amino acid.

The peptide sequence comprised in protein that is comprised in the complex of the invention, or that is to be bound, detected, immobilized, isolated, or purified in the use of the invention, or that is to be bound or detected in the method of binding or detection of the present invention, may comprise a sequence selected from the group consisting of:

(a) (SEQ ID NO: 32)
GRLEEELRRRLS;

(b) (SEQ ID NO: 33)
MSGRLEEELRRRLSP;

(c) (SEQ ID NO: 34)
SDSGLEQELRRRLSPG;

(d) (SEQ ID NO: 35)
PDGGLEQELRRRLTAP;

(e) (SEQ ID NO: 36)
PSGGLEQELRRRLTAP;

(f) (SEQ ID NO: 37)
DSPGLEQELRRRLTAP;

(g) (SEQ ID NO: 38)
PDSGLEQELRRRLTPA;

-continued (h) (SEQ ID NO: 39)
SPSGLEEELRRRLTAEP;

(i) (SEQ ID NO: 40)
GPSGLEQELRRRLT;

(j) (SEQ ID NO: 41)
GPSGLEQELRRRLTAAS;

(k) (SEQ ID NO: 42)
SPSRLEEELRRRLPSK;

(l) (SEQ ID NO: 43)
SPSGLEQELRRRLTPS;

(m) (SEQ ID NO: 44)
SPGRLEQEIRRRLSPS;

(n) (SEQ ID NO: 45)
PSGRLEEELRRRLSPS;

(o) (SEQ ID NO: 46)
PSGRLEEELRRRLS;

(p) (SEQ ID NO: 47)
PSGRLEEELRRRLA;
and (q) (SEQ ID NO: 48)
PSGRLEEELRRRLSP.

The peptide sequence comprised in protein that is comprised in the complex of the invention, or that is to be bound, detected, immobilized, isolated, or purified in the use of the invention, or that is to be bound or detected in the method of binding or detection of the present invention, may comprise a peptide comprising as a core structure the sequence of X1-X2-L-E-X5-E-L-R-R-R-L-X12-X13 (SEQ ID NO: 49), wherein X1 is S or G or P, X2 is R or G or P, X5 is E or Q, X12 is S or T or D or E, and X13 is P or A or D or no amino acid. A peptide comprising as a core structure the sequence SEQ ID NO: 49 may comprise N-terminal of X1 the amino acids Xa-Xb, wherein Xa is P or D or S or G or no amino acid, and Xb is D or S or P or no amino acid. Such a peptide may also comprise C-terminal of X13 the amino acids Xy-Xz, wherein Xy is G or P or E or D or S or no amino acid, and Xz is P or no amino acid.

The peptide sequence comprised in protein that is comprised in the complex of the invention, or that is to be bound, detected, immobilized, isolated, or purified in the use of the invention, or that is to be bound or detected in the method of binding or detection of the present invention, may have the core structure of SEQ ID NO: 49 and may comprise a sequence selected from the group consisting of:

(a) (SEQ ID NO: 50)
PDSGLEQELRRRLSPG;

(b) (SEQ ID NO: 51)
PDSGLEQELRRRLTAP;

-continued

```
(c)
                                  (SEQ ID NO: 52)
PSSGLEQELRRRLTAP;

(d)
                                  (SEQ ID NO: 53)
DPSGLEQELRRRLTAP;

(e)
                                  (SEQ ID NO: 54)
DSGPLEQELRRRLTAP;

(f)
                                  (SEQ ID NO: 55)
SPSRLEEELRRRLTAEP;

(g)
                                  (SEQ ID NO: 56)
SPSGLEEELRRRLTAP;

(h)
                                  (SEQ ID NO: 57)
SPSGLEEELRRRLDAP;

(i)
                                  (SEQ ID NO: 58)
SPSGLEEELRRRLEAP;

(j)
                                  (SEQ ID NO: 59)
SPSGLEEELRRRLTDP;

(k)
                                  (SEQ ID NO: 60)
SPSGLEEELRRRLTADP;

(l)
                                  (SEQ ID NO: 61)
GPSGLEQELRRRLTA;

(m)
                                  (SEQ ID NO: 62)
SPSGLEQELRRRLTDP;

(n)
                                  (SEQ ID NO: 63)
SPSGLEQELRRRLTADP;

(o)
                                  (SEQ ID NO: 64)
SPSGLEQELRRRLTAEP;

(p)
                                  (SEQ ID NO: 37)
DSPGLEQELRRRLTAP;
and

(q)
                                  (SEQ ID NO: 65)
SPSGLEQELRRRLSPS.
```

The peptide sequence comprised in protein that is comprised in the complex of the invention, or that is to be bound, detected, immobilized, isolated, or purified in the use of the invention, or that is to be bound or detected in the method of binding or detection of the present invention, may comprise a peptide comprising as a core structure the sequence of X1-X2-X3-X4-X5-X6-X7-X8-X9-R-L-X12-X13 (SEQ ID NO: 66), wherein X1 is G or S, X2 is R or G or A or E, X3 is L or V, X4 is E or Q, X5 is E or Q, X6 is E or Q, X7 is L or I or V, X8 is R or A or Q or E, X9 is R or A or Q or E, X12 is S or Tor L or no amino acid, and X13 is K or P or S or no amino acid. A peptide comprising as a core structure the sequence SEQ ID NO: 66 may comprise N-terminal of X1 the amino acids Xa-Xb, wherein Xa is D or S or G or M or no amino acid and Xb is S or D or P or M or no amino acid. Such a peptide may also comprise C-terminal of X13 the amino acids Xy-Xz, wherein Xy is G or S or P or no amino acid, Xz is S or no amino acid.

The peptide sequence comprised in protein that is comprised in the complex of the invention, that is to be bound, detected, immobilized, isolated, or purified in the use of the invention, or to be bound or detected in the method of binding or detection of the present invention, may have the core structure of SEQ ID NO: 66 and may comprise a sequence selected from the group consisting of:

```
(a)
                                  (SEQ ID NO: 67)
DSGRLEEELRRRLSKG;

(b)
                                  (SEQ ID NO: 68)
DSGRLEEELRRRLSPG;

(c)
                                  (SEQ ID NO: 69)
SDSGLEEELRRRLSPG;

(d)
                                  (SEQ ID NO: 70)
SDSGVEEELRRRLSPG;

(f)
                                  (SEQ ID NO: 71)
SDSAVEEELRRRLSPG;

(g)
                                  (SEQ ID NO: 72)
SDSGLQEELRRRLSPG;

(h)
                                  (SEQ ID NO: 73)
SDSGLEEQLRRRLSPG;

(i)
                                  (SEQ ID NO: 74)
SDSGLEEEIRRRLSPG;

(j)
                                  (SEQ ID NO: 75)
SDSGLEEEVRRRLSPG;

(k)
                                  (SEQ ID NO: 76)
DSGELEEELRRRLSPG;

(l)
                                  (SEQ ID NO: 77)
DSGRLEQELRRRLSPG;

(m)
                                  (SEQ ID NO: 78)
DSGRLEEEIRRRLSPG;

(n)
                                  (SEQ ID NO: 79)
DSGRLEQEIRRRLSPG;

(o)
                                  (SEQ ID NO: 80)
DSGRLEQEIARRLSPG;

(p)
                                  (SEQ ID NO: 81)
DSGRLEQEIQRRLSPG;

(q)
                                  (SEQ ID NO: 82)
DSGRLEQEIERRLSPG;

(r)
                                  (SEQ ID NO: 83)
DSGRLEQEIRARLSPG;

(s)
                                  (SEQ ID NO: 84)
DSGRLEQEIRQRLSPG;
```

-continued (t) (SEQ ID NO: 85)
DSGRLEQEIRERLSPG;

(u) (SEQ ID NO: 86)
GPSRLEEELRRRL;

(v) (SEQ ID NO: 87)
MSGLEQELRRRLTPS;

(w) (SEQ ID NO: 88)
MSGRLEEELRRRLSPS;

(x) (SEQ ID NO: 89)
SPSAVEEELRRRLSPS;

(y) (SEQ ID NO: 90)
GPSAVEEELRRRLS;

(z) (SEQ ID NO: 91)
MPSGLEQELRRRLTPS;

(aa) (SEQ ID NO: 92)
MSSGLEQELRRRLTPS;
and (bb) (SEQ ID NO: 93)
MPSGRLEEELRRRLSPS.

It must be noted that as used herein, the singular forms "a", "an" and "the" include plural references and vice versa unless the context clearly indicates otherwise.

Unless otherwise indicated, the term "at least" preceding a series of elements is to be understood to refer to every element in the series.

Those skilled in the art will recognize or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

Throughout this specification and the claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms. E.g., the term "comprising" is meant to provide explicit support also for "consisting essentially of" and "consisting of", the term "consisting essentially of" is meant to provide explicit support also for "comprising" and "consisting of", the term "consisting of" is meant to provide explicit support also for "consisting essentially of" and "comprising". The possibility to replace terms with each other is not to be understood that these terms are synonymous.

The invention is further characterized by the following items:

Item 1: A single-domain antibody that specifically binds to an epitope tag comprising the sequence SRLEEELRRRLTE (SEQ ID NO: 2), wherein the antibody comprises the CDR1 sequence as shown in SEQ ID NO: 94, the CDR2 sequence as shown in SEQ ID NO: 97, and the CDR3 sequence as shown in SEQ ID NO: 98; wherein the antibody further comprises at positions corresponding to sequence position 47, 48, and 50 of SEQ ID NO: 1 the following amino acid residues: Arg at position 47, Arg at position 48, Met at position 50; and wherein the antibody comprises a sequence having at least 90% sequence identity to any one of SEQ ID NOs: 118-125.

Item 2: The antibody of item 1, wherein the antibody is humanized.

Item 3: The antibody of any one of the preceding items, wherein the antibody comprises a sequence that has at least about 70% V segment identity to the closest human germline sequence.

Item 4: The antibody of item 3, wherein the human germline sequence is IGHV3-23*4 set forth in SEQ ID NO: 110.

Item 5: The antibody of any one of the preceding items, wherein the antibody has an affinity for the epitope tag shown in SEQ ID NO: 2 that is at least comparable with the affinity of the antibody of SEQ ID NO: 1, wherein at least comparable preferably means that the $K_D$ of the antibody is not more than by factor 2.5 higher than the $K_D$ of SEQ ID NO: 1, as preferably measured by biolayer interferometry, preferably by a method as essentially described in Method 1.

Item 6: The antibody of any one of the preceding items, wherein the antibody has a $K_D$ for the epitope tag shown in SEQ ID NO: 2 of about $5\times10^{-10}$ M or lower, preferably $3\times10^{-10}$M or lower, as preferably measured by biolayer interferometry, preferably by a method as essentially described in Method 1.

Item 7: The antibody of any one of the preceding items, wherein the antibody has a higher Tm as compared to the antibody of SEQ ID NO: 1.

Item 8: The antibody of any one of the preceding items, wherein the antibody has a Tm of at least about 63° C., wherein the Tm is preferably measured as essentially described in Method 2.

Item 9: The antibody of any one the preceding items, wherein the antibody comprises a His residue at the position corresponding to sequence position 99 of SEQ ID NO: 1.

Item 10: The antibody of any one the preceding items, wherein the antibody comprises a Val residue at the position corresponding to sequence position 100 of SEQ ID NO: 1.

Item 11: The antibody of any one the preceding items, wherein the antibody comprises a Val residue at the position corresponding to sequence position 5 of SEQ ID NO: 1.

Item 12: The antibody of any one the preceding items, wherein the antibody comprises a Tyr residue at the position corresponding to sequence position 40 of SEQ ID NO: 1.

Item 13: The antibody of any one the preceding items, wherein the antibody comprises a Gln residue at the position corresponding to sequence position 117 of SEQ ID NO: 1.

Item 14: The antibody of any one of the preceding items, wherein the antibody comprises an FR1 sequence having at least 80%, at least 85%, at least 90%, or at least 95% sequence identity or being identical to the sequence of SEQ ID NO: 99.

Item 15: The antibody of any one of the preceding items, wherein the antibody comprises an FR2 sequence having at least 80%, at least 85%, at least 90%, or at least 95% sequence identity or being identical to the sequence of SEQ ID NO: 102.

Item 16: The antibody of any one of the preceding items, wherein the antibody comprises an FR3 sequence having at least 80%, at least 85%, at least 90%, or at least 95% sequence identity or being identical to the sequence of SEQ ID NO: 108.

Item 17: The antibody of any one of the preceding items, wherein the antibody comprises an FR4 sequence having at least 80%, at least 85%, at least 90%, or at least 95% sequence identity or being identical to the sequence of SEQ ID NO: 109.

Item 18: The antibody of any one of the preceding items, wherein the antibody comprises FR1, FR2, FR3, and FR4 sequences, that have at least 80%, at least 85%, at least 90%, or at least 95% sequence identity or are identical to the sequences set forth in SEQ ID NOs: 99, 102, 108, and 109, respectively.

Item 19: The antibody of any one of the preceding items, wherein the framework sequence of the antibody is defined by the amino acid positions corresponding to positions 1-25, 39-53, 61-98, and 112-122 of SEQ ID NO: 1.

Item 20: The antibody of any one of the preceding items, wherein the antibody comprises a protein A binding site.

Item 21: The antibody of any one of the preceding items, wherein the antibody comprises a Thr residue at the position corresponding to sequence position 60 of SEQ ID NO: 1.

Item 22: The antibody of any one of the preceding items, wherein the antibody comprises a Lys residue at the position corresponding to sequence position 67 of SEQ ID NO: 1.

Item 23: The antibody of any one of the preceding items, wherein the antibody comprises at positions corresponding to sequence positions 60 and 67 of SEQ ID NO: 1 the following amino acid residues: a Thr at position 60 and a Lys at position 67.

Item 24: The antibody of any one of the preceding items, wherein the antibody comprises a Tyr residue at the position corresponding to sequence position 61 of SEQ ID NO: 1.

Item 25: The antibody of any one of the preceding items, wherein the antibody comprises an Asp residue at the positions corresponding to sequence position 64 of SEQ ID NO: 1.

Item 25a: The antibody of any one of the preceding items, wherein the antibody comprises a Tyr residue at the position corresponding to sequence position 61 of SEQ ID NO: 1 and an Asp residue at the positions corresponding to sequence position 64 of SEQ ID NO: 1.

Item 26: The antibody of any one of the preceding items, wherein the antibody comprises a CDR2 sequence set forth in SEQ ID NOs: 95 or 96.

Item 26a: The antibody of any one of the preceding items, wherein the antibody comprises a CDR2 sequence set forth in SEQ ID NO: 95.

Item 26b: The antibody of any one of the preceding items, wherein the antibody comprises a CDR2 sequence set forth in SEQ ID NO: 96.

Item 27: The antibody of any one of the preceding items, wherein the antibody comprises a FR2 sequence having at least 80%, at least 85%, at least 90%, or at least 95% sequence identity or being identical to any one of SEQ ID NOs: 100, 101.

Item 28: The antibody of any one of the preceding items, wherein the antibody comprises a FR3 sequence having at least 80%, at least 85%, at least 90%, or at least 95% sequence identity or being identical to any one of SEQ ID NOs: 103-107.

Item 29: The antibody of any one of the preceding items, wherein the antibody comprises a sequence having at least 95% sequence identity to any one of SEQ ID NOs: 118-125.

Item 30: The antibody of any one of the preceding items, wherein the antibody comprises a sequence set forth in any one of SEQ ID NOs: 118-125.

Item 30a: The antibody of any one of the preceding items, wherein the antibody does not comprise a N×T/S motif.

Item 31: The antibody of any one of the preceding items, wherein the antibody is conjugated to a detectable label.

Item 32: The antibody of any one of the preceding items, wherein the detectable label is a fluorescent label.

Item 33: The antibody of any one of the preceding items, wherein the detectable label is an affinity tag.

Item 34: A protein comprising the amino acid sequence of the antibody of any one of items 1-33.

Item 35: A complex comprising a. a protein comprising the amino acid sequence of X1-X2-L-E-X5-E-X7-R-R-R-L-X12-X13 (SEQ ID NO: 3), wherein X1 is G or S or P or T, X2 is R or G or P, X5 is E or Q, X7 is L or I, X12 is S or T or P or A or D or E, and wherein X13 is P or A or S or K or D or E or no amino acid; and b. an antibody of any one of items 1-33.

Item 36: A nucleic acid encoding an antibody of any one of items 1-33.

Item 37: The nucleic acid of item 36, wherein the nucleic acid is DNA.

Item 38: The nucleic acid of item 36, wherein the nucleic acid is RNA.

Item 39: A vector comprising the nucleic acid of any one of items 34-36.

Item 40: A host cell comprising the nucleic acid of any one of items 36-38 or the vector of item 39 or expressing the antibody of any one of items 1-33.

Item 41: Use of the antibody of any one of items 1-33 for the binding, detection, immobilization, isolation, or purification of a protein comprising the amino acid sequence of X1-X2-L-E-X5-E-X7-R-R-R-L-X12-X13 (SEQ ID NO: 3), wherein X1 is G or S or P or T, X2 is R or G or P, X5 is E or Q, X7 is L or I, X12 is S or T or P or A or D or E, and wherein X13 is P or A or S or K or D or E or no amino acid.

Item 42: The use of item 41, wherein said amino acid sequence comprises the sequence of X1-X2-L-E-X5-E-L-R-R-R-L-X12-X13 (SEQ ID NO: 4), wherein X1 is S or T, X2 is R or G, X5 is E or Q, X12 is T or D or E, and wherein X13 is A or D or E or no amino acid.

Item 43: The use of item 41 or 42, wherein said amino acid sequence comprises the sequence of SRLEEELRRRLTE (SEQ ID NO: 2).

Item 44: The use of any one of items 41 to 43, wherein said amino acid sequence comprises a sequence selected from the group consisting of:

```
(a)
                                    (SEQ ID NO: 5)
MPSRLEEELRRRLTEP;

(b)
                                    (SEQ ID NO: 6)
PSRLEEELRRRLTEP;

(c)
                                    (SEQ ID NO: 7)
PSRLEEELRRRLTE;

(d)
                                    (SEQ ID NO: 8)
GRSRLEEELRRRLTA;

(e)
                                    (SEQ ID NO: 9)
PGSRLEEELRRRLTAP;

(f)
                                   (SEQ ID NO: 10)
PSTRLEEELRRRLTAP;

(g)
                                   (SEQ ID NO: 11)
SPSRLEEELRRRLTAP;

(h)
                                   (SEQ ID NO: 12)
SPSRLEEELRRRLDAP;

(i)
                                   (SEQ ID NO: 13)
SPSRLEEELRRRLEAP;

(j)
                                   (SEQ ID NO: 14)
SPSRLEEELRRRLTDP;

(k)
                                   (SEQ ID NO: 15)
SPSRLEEELRRRLTEP;

(l)
                                   (SEQ ID NO: 16)
SPSRLEEELRRRLTADP;

(m)
                                   (SEQ ID NO: 17)
SPSGLEEELRRRLTEP;

(n)
                                   (SEQ ID NO: 18)
GPSRLEEELRRRLT;

(o)
                                   (SEQ ID NO: 19)
GPSRLEEELRRRLTA;

(p)
                                   (SEQ ID NO: 20)
GPSRLEEELRRRLTAA;

(q)
                                   (SEQ ID NO: 21)
```

-continued

```
GPSRLEEELRRRLTAAS;

(r)
                                   (SEQ ID NO: 22)
SPSGLEQELRRRLTAP;

(s)
                                   (SEQ ID NO: 23)
SPSGLEQELRRRLDAP;

(t)
                                   (SEQ ID NO: 24)
SPSGLEQELRRRLEAP;

(u)
                                   (SEQ ID NO: 25)
SPSGLEQELRRRLTEP;

(v)
                                   (SEQ ID NO: 26)
GPSRLEEELRRRLTAP;

(w)
                                   (SEQ ID NO: 27)
GPSRLEEELRRRLTEP;

(x)
                                   (SEQ ID NO: 28)
GPSRLEEELRRRLTE;

(y)
                                   (SEQ ID NO: 29)
MSRLEEELRRRLTEP;
and

(z)
                                   (SEQ ID NO: 30)
MSSRLEEELRRRLTEP.
```

Item 45: The use of item 41, wherein said amino acid sequence comprises the sequence of X1-X2-L-E-X5-E-X7-R-R-R-L-X12-X13 (SEQ ID NO: 31), wherein X1 is G or S or P, X2 is R or G, X5 is E or Q, X7 is L or I, X12 is S or T or P or A, and X13 is P or A or S or no amino acid.

Item 46: The use of item 41 or 45, wherein said amino acid sequence comprises the sequence of G-R-L-E-E-E-L-R-R-R-L-S(SEQ ID NO: 32) or a variant thereof, wherein the variant has as compared to (SEQ ID NO: 32) 1 to 6 mutations selected from the group consisting of: G1→S, G1→P, R2→G, E5→Q, L7→I, S12→T, S12→P, S12→A, addition of P13, addition of A13, and addition of S13.

Item 47: The use of any one of items 41 and 45-46, wherein said amino acid sequence comprises a sequence selected from the group consisting of:

```
(a)
                                   (SEQ ID NO: 32)
GRLEEELRRRLS;

(b)
                                   (SEQ ID NO: 33)
MSGRLEEELRRRLSP;

(c)
                                   (SEQ ID NO: 34)
SDSGLEQELRRRLSPG;

(d)
                                   (SEQ ID NO: 35)
PDGGLEQELRRRLTAP;

(e)
                                   (SEQ ID NO: 36)
```

-continued

```
PSGGLEQELRRRLTAP;

(f)
                    (SEQ ID NO: 37)
DSPGLEQELRRRLTAP;

(g)
                    (SEQ ID NO: 38)
PDSGLEQELRRRLTPA;

(h)
                    (SEQ ID NO: 39)
SPSGLEEELRRRLTAEP;

(i)
                    (SEQ ID NO: 40)
GPSGLEQELRRRLT;

(j)
                    (SEQ ID NO: 41)
GPSGLEQELRRRLTAAS;

(k)
                    (SEQ ID NO: 42)
SPSRLEEELRRRLPSK;

(l)
                    (SEQ ID NO: 43)
SPSGLEQELRRRLTPS;

(m)
                    (SEQ ID NO: 44)
SPGRLEQEIRRRLSPS;

(n)
                    (SEQ ID NO: 45)
PSGRLEEELRRRLSPS;

(o)
                    (SEQ ID NO: 46)
PSGRLEEELRRRLS;

(p)
                    (SEQ ID NO: 47)
PSGRLEEELRRRLA;
and

(q)
                    (SEQ ID NO: 48)
PSGRLEEELRRRLSP.
```

Item 48: A method of binding or detecting a protein comprising the amino acid sequence of X1-X2-L-E-X5-E-X7-R-R-R-L-X12-X13 (SEQ ID NO: 3), wherein X1 is G or S or P or T, X2 is R or G or P, X5 is E or Q, X7 is L or I, X12 is S or T or P or A or D or E, and wherein X13 is P or A or S or K or D or E or no amino acid, comprising contacting the protein with an antibody of any one of items 1-33 and optionally detecting the antibody or a label comprised in the antibody.

Item 49: A method of producing the antibody of any one of items 1-33 comprising cultivating the host cell of item 40 under conditions allowing the expression of the antibody.

Item 50: The method of item 49, further comprising recovering and/or isolating the antibody from the host cell or from cultivation medium.

EXAMPLES

Example 1: CDR Grafting and Humanization of NbALFA

In the first step, the CDRs of NbALFA were grafted onto multiple acceptor frameworks. As described herein, CDRs were defined broadly by a combination of Kabat and IMGT numbering schemes. For CDR grafting, seven variants of humanized VHH acceptor frameworks were chosen. Variants 1 to 7 of humanised NbALFA antibody are set forth in SEQ ID NOs: 111 to 117.

Genes encoding variants 1 to 7 were cloned into expression vectors and subsequently produced in *E. coli* by procedures well known to a person skilled in the art. Antibody variants were purified with IMAC chromatography and subsequently tested for antigen binding with biolayer interferometry.

Variants 1 and 2 failed in production and variants 3 to 6 showed no binding to the epitope tag of SEQ ID NO: 2. Variant 7 showed binding to the epitope tag of SEQ ID NO: 2, albeit with a significantly impaired antigen recognition, demonstrated by a fast off-rate and low KD (see Table 1).

TABLE 1

Binding affinities of humanized NbALFA variants

| Variant | KD [M] | Ka [$Ms^{-1}$] | Kdis [$s^{-1}$] |
|---|---|---|---|
| wtNbALFA (SEQ ID NO: 1) | $1.60*10^{-10}$ | $3.99*10^{5}$ | $6.37*10^{-5}$ |
| Variant 1 (SEQ ID NO: 111) | | Failed production | |
| Variant 2 (SEQ ID NO: 112) | | Failed production | |
| Variant 3 (SEQ ID NO: 113) | | Loss of binding | |
| Variant 4 (SEQ ID NO: 114) | | Loss of binding | |
| Variant 5 (SEQ ID NO: 115) | | Loss of binding | |
| Variant 6 (SEQ ID NO: 116) | | Loss of binding | |
| Variant 7 (SEQ ID NO: 117) | $1.86*10^{-9}$ | $1.49*10^{5}$ | $2.76*10^{-4}$ |

Example 2: Further Engineering of Humanized Variants

Based on extensive structural analysis, 8 further variants of humanized NbALFA were generated. Variants 8 to 15 are set forth in SEQ ID NO: 118 to 125 and their affinity, on/off rates, thermal stability, aggregation behavior and IGHV3-23 framework identity are shown in Table 2. Surprisingly, all variants showed binding to SEQ ID NO: 2 with at least comparable binding affinity as compared to wtNbALFA. Strikingly, variants 9, 10, 12, 13, 14, and 15 exhibited wild type affinity, while variant 11 even showed elevated affinity towards SEQ ID NO: 2.

TABLE 2 affinity optimized variants

| Variant # | $K_D$ [M] | Ka [1/Ms] | kdis [1/s] | SEC Area [% @ 280 nm] |
|---|---|---|---|---|
| wtNbALFA (SEQ ID NO: 1) | $1.60*10^{-10}$ | $3.99*10^{5}$ | $6.37*10^{-5}$ | 100 |
| Variant 8 (SEQ ID NO: 118) | $2.63*10^{-10}$ | $1.00*10^{6}$ | $2.63*10^{-4}$ | 87.16 |
| Variant 9 (SEQ ID NO: 119) | $1.82*10^{-10}$ | $2.03*10^{5}$ | $3.69*10^{-5}$ | 100 |
| Variant 10 (SEQ ID NO: 120) | $3.06*10^{-10}$ | $4.80*10^{5}$ | $1.47*10^{-4}$ | 56.46 |
| Variant 11 (SEQ ID NO: 121) | $5.95*10^{-11}$ | $6.22*10^{5}$ | $3.70*10^{-5}$ | 100 |
| Variant 12 (SEQ ID NO: 122) | $3.48*10^{-10}$ | $6.09*10^{5}$ | $1.51*10^{-4}$ | 97.56 |
| Variant 13 (SEQ ID NO: 123) | $2.17*10^{-10}$ | $7.67*10^{5}$ | $1.67*10^{-4}$ | 100 |

TABLE 2-continued

| affinity optimized variants | | | | |
|---|---|---|---|---|
| Variant # | $K_D$ [M] | Ka [1/Ms] | kdis [1/s] | SEC Area [% @ 280 nm] |
| Variant 14 (SEQ ID NO: 124) | $2.18*10^{-10}$ | $5.96*10^{5}$ | $1.30*10^{-4}$ | 100 |
| Variant 15 (SEQ ID NO: 125) | $2.35*10^{-10}$ | $1.59*10^{6}$ | $3.02*10^{-4}$ | 100 |

TABLE 3

| Framework identity and V segment identity of humanized variants | | | | | | |
|---|---|---|---|---|---|---|
| | Framework identity [%] IGHV3-23, excluding CDRs | | | | | |
| Variant # | FR1 | FR2 | FR3 | FR4 | Overall framework identity (Weighted average) | V segment identity [%] IGHV3-23 |
| wtNbALFA (SEQ ID NO: 1) | 92.0 | 53.3 | 55.3 | 90.9 | 69.7 | 59.6 |
| Variant 8 (SEQ ID NO: 118) | 100 | 66.7 | 78.9 | 90.9 | 84.3 | 72.7 |
| Variant 9 (SEQ ID NO: 119) | 100 | 66.7 | 78.9 | 90.9 | 84.3 | 72.7 |
| Variant 10 (SEQ ID NO: 120) | 100 | 66.7 | 78.9 | 90.9 | 84.3 | 73.7 |
| Variant 11 (SEQ ID NO: 121) | 100 | 66.7 | 81.6 | 90.9 | 85.4 | 73.7 |
| Variant 12 (SEQ ID NO: 122) | 100 | 66.7 | 81.6 | 90.9 | 85.4 | 74.7 |
| Variant 13 (SEQ ID NO: 123) | 100 | 66.7 | 86.8 | 90.9 | 87.6 | 76.8 |
| Variant 14 (SEQ ID NO: 124) | 100 | 66.7 | 92.1 | 90.9 | 89.9 | 77.8 |
| Variant 15 (SEQ ID NO: 125) | 100 | 66.7 | 97.4 | 90.9 | 92.2 | 80.8 |
| US2023/0093123A 1-Seq35 (SEQ ID NO: 129) | 88.0 | 60.0 | 71.1 | 66.7 | 76.4 | 66.7 |

Example 3: Determination of SpA Binding

To further investigate the newly generated variants, SpA affinity was determined with the humanized NbALFA. Capacity of SpA binding may provide a straightforward purification process of the humanised antibody under GMP conditions and to circumvent the need to establish a new purification method. SpA binding and the capability to be purified using SpA columns were thus investigated (see FIG. 3, Table 4). The spike experiment revealed a quantitative binding of variant 10, 12, 13 and 15 to the column as the flow tough lacked any presence of the VHH. These four variants were not detectable in the two wash fractions and eluted in the two elution steps. However, variants 11 and 14 were bound by the column but remained detectable in the flow through fractions. In the washing steps a clear "bleeding" was detected, and the elution did not lead to an elevated presence of the VHH in the fraction, rendering both variants unfit for SpA-based purification.

TABLE 4

| determination of SpA binding | |
|---|---|
| Variant | SpA binding |
| wtNbALFA (SEQ ID NO: 1) | − |
| Variant 10 (SEQ ID NO: 120) | + |
| Variant 11 (SEQ ID NO: 121) | − |
| Variant 12 (SEQ ID NO: 122) | + |
| Variant 13 (SEQ ID NO: 123) | + |
| Variant 14 (SEQ ID NO: 124) | − |
| Variant 15 (SEQ ID NO: 125) | + |

Example 4: Determination of Thermal Stability

Thermal stability of the humanized variants of NbALFA was determined. Tm values representing thermal stability are shown in Table 5. Strikingly, despite the humanization, variant 8 showed comparable Tm values as wtNbALFA, while variants 9-15 even surprisingly showed higher thermal stability as wtNbALFA.

TABLE 5

| determination of thermal stability | |
|---|---|
| Variant # | Tm [° C.] |
| wtNbALFA (SEQ ID NO: 1) | 61.3 |
| Variant 8 (SEQ ID NO: 118) | 61.1 |
| Variant 9 (SEQ ID NO: 119) | 65.2 |
| Variant 10 (SEQ ID NO: 120) | 63.8 |
| Variant 11 (SEQ ID NO: 121) | 64.6 |
| Variant 12 (SEQ ID NO: 122) | 64.8 |
| Variant 13 (SEQ ID NO: 123) | 66.7 |
| Variant 14 (SEQ ID NO: 124) | 64.2 |
| Variant 15 (SEQ ID NO: 125) | 66.8 |

TABLE 6

| VHH sequences of humanized NbALFA nanobodies | |
|---|---|
| Variant # | Sequence |
| Variant 1 (SEQ ID NO: 111) | EVQLLESGGGLVQPGGSLRLSCAASGVTISALNAMAMGW YRQAPGKRREMVSAVSERGNAMYRESVQGRFTISRDNSK NTLYLQMNSLRAEDTAVYYCAKLEDRVDSFHDYWGQGT LVTVSS |
| Variant 2 (SEQ ID NO: 112) | EVQLLESGGGLVQPGGSLRLSCAASGVTISALNAMAMGW FRQAPGKEREGVSAVSERGNAMYRESVQGRFTISRDNSKN TLYLQMNSLRAEDTAVYYCAKLEDRVDSFHDYWGQGTL VTVSS |
| Variant 3 (SEQ ID NO: 113) | EVQLLESGGGLVQPGGSLRLSCAASGVTISALNAMAMGW FRQAPGKGLEFVAAVSERGNAMYRESVQGRFTISRDNSKN TLYLQMNSLRAEDTAVYYCAALEDRVDSFHDYWGQGTL VTVSS |
| Variant 4 (SEQ ID NO: 114) | EVQLLESGGGLVQPGGSLRLSCAASGVTISALNAMAMGW FRQAPGKGLEFVAAVSERGNAYYRDSVKGRFTISRDNSKN TLYLQMNSLRAEDTAVYYCAALEDRVDSFHDYWGQGTL VTVSS |
| Variant 5 (SEQ ID NO: 115) | EVQLQASGGGFVQPGGSLRLSCAASGVTISALNAMAMGW FRQAPGKEREFVSAISERGNAYYRDSVKGRFTISRDNSKN TVYLQMNSLRAEDTATYYCAALEDRVDSFHDYWGQGTQV TVSS |
| Variant 6 (SEQ ID NO: 116) | EVQLQASGGGFVQPGGSLRLSCAASGVTISALNAMAMGW FRQAPGKEREFVSAVSERGNAMYRESVQGRFTISRDNSKN TVYLQMNSLRAEDTATYYCAALEDRVDSFHDYWGQGTQ VTVSS |

TABLE 6-continued

| VHH sequences of humanized NbALFA nanobodies | |
|---|---|
| Variant # | Sequence |
| Variant 7 (SEQ ID NO: 117) | EVQLVESGGGLVQPGGSLRLSCAASGVTISALNAMAMGWFRQAPGKGRELVAAVSERGNAMYRESVQGRFTISRDNAKRMVYLQMNSLRAEDTAVYYCHVLEDRVDSFHDYWGQGTQVTVSS |
| Variant 8 (SEQ ID NO: 118) | EVQLVESGGGLVQPGGSLRLSCAASGVTISALNAMAMGWFRQAPGKRREMVAAVSERGNAMYRESVQGRFTISRDNAKRMVYLQMNSLRAEDTAVYYCHVLEDRVDSFHDYWGQGTQVTVSS |
| Variant 9 (SEQ ID NO: 119) | EVQLVESGGGLVQPGGSLRLSCAASGVTISALNAMAMGWYRQAPGKRREMVAAVSERGNAMYRESVQGRFTISRDNAKRMVYLQMNSLRAEDTAVYYCHVLEDRVDSFHDYWGQGTQVTVSS |
| Variant 10 (SEQ ID NO: 120) | EVQLVESGGGLVQPGGSLRLSCAASGVTISALNAMAMGWYRQAPGKRREMVAAVSERGNTMYRESVQGRFTISRDNAKRMVYLQMNSLRAEDTAVYYCHVLEDRVDSFHDYWGQGTQVTVSS |
| Variant 11 (SEQ ID NO: 121) | EVQLVESGGGLVQPGGSLRLSCAASGVTISALNAMAMGWYRQAPGKRREMVAAVSERGNAMYRESVKGRFTISRDNAKRMVYLQMNSLRAEDTAVYYCHVLEDRVDSFHDYWGQGTQVTVSS |
| Variant 12 (SEQ ID NO: 122) | EVQLVESGGGLVQPGGSLRLSCAASGVTISALNAMAMGWYRQAPGKRREMVAAVSERGNTMYRESVKGRFTISRDNAKRMVYLQMNSLRAEDTAVYYCHVLEDRVDSFHDYWGQGTQVTVSS |
| Variant 13 (SEQ ID NO: 123) | EVQLVESGGGLVQPGGSLRLSCAASGVTISALNAMAMGWYRQAPGKRREMVAAVSERGNTYYRDSVKGRFTISRDNAKRMVYLQMNSLRAEDTAVYYCHVLEDRVDSFHDYWGQGTQVTVSS |
| Variant 14 (SEQ ID NO: 124) | EVQLVESGGGLVQPGGSLRLSCAASGVTISALNAMAMGWYRQAPGKRREMVAAVSERGNAMYRESVKGRFTISRDNSKNTLYLQMNSLRAEDTAVYYCHVLEDRVDSFHDYWGQGTQVTVSS |
| Variant 15 (SEQ ID NO: 125) | EVQLVESGGGLVQPGGSLRLSCAASGVTISALNAMAMGWYRQAPGKRREMVAAVSERGNTYYRDSVKGRFTISRDNSKNTLYLQMNSLRAEDTAVYYCHVLEDRVDSFHDYWGQGTQVTVSS |

TABLE 7

| CDR and Framework region sequences of humanized NbALFA nanobodies of the present invention | | | |
|---|---|---|---|
| SEQ ID NO | Region | Applicable to variants | Sequence |
| SEQ ID NO: 94 | CDR1 | Variants 8 to 15 | GVTISALNAMAMG |
| SEQ ID NO: 95 | CDR2 | Variants 8, 9, 11, 14 | VSERGNA |
| SEQ ID NO: 96 | CDR2 | Variants 10, 12, 13, 15 | VSERGNT |
| SEQ ID NO: 97 | CDR2 con-sensus | Variants 8 to 15 | VSERGNX1, wherein X1 is A or T |
| SEQ ID NO: 98 | CDR3 | Variants 8 to 15 | HVLEDRVDSFHDY |

TABLE 7-continued

| CDR and Framework region sequences of humanized NbALFA nanobodies of the present invention | | | |
|---|---|---|---|
| SEQ ID NO | Region | Applicable to variants | Sequence |
| SEQ ID NO: 99 | FR1 | Variants 8 to 15 | EVQLVESGGGLVQPGGSLRLSCAAS |
| SEQ ID NO: 100 | FR2 | Variant 8 | WFRQAPGKRREMVAA |
| SEQ ID NO: 101 | FR2 | Variants 9 to 15 | WYRQAPGKRREMVAA |
| SEQ ID NO: 102 | FR2 con-sensus | Variants 8 to 15 | WXIRQAPGKRREMVAA, wherein X1 is For Y |
| SEQ ID NO: 103 | FR3 | Variants 8 to 10 | MYRESVQGRFTISRDNAKRMVYLQMNSLRAEDTAVYYC |
| SEQ ID NO: 104 | FR3 | Variants 11, 12 | MYRESVKGRFTISRDNAKRMVYLQMNSLRAEDTAVYYC |
| SEQ ID NO: 105 | FR3 | Variant 13 | YYRDSVKGRFTISRDNAKRMVYLQMNSLRAEDTAVYYC |
| SEQ ID NO: 106 | FR3 | Variant 14 | MYRESVKGRFTISRDNSKNTLYLQMNSLRAEDTAVYYC |
| SEQ ID NO: 107 | FR3 | Variant 15 | YYRDSVKGRFTISRDNSKNTLYLQMNSLRAEDTAVYYC |
| SEQ ID NO: 108 | FR3 con-sensus | Variants 8 to 15 | X1YRX2SVX3GRFTISRDNX4KX5X6X7YLQMNSLRAEDTAVYYC, wherein X1 is M or Y, X2 is D or E, X3 is Q or K, X4 is A or S, X5 is N or R, X6 is M or T, X7 is V or L |
| SEQ ID NO: 109 | FR4 | Variants 8 to 15 | WGQGTQVTVSS |

Example 5: Direct Comparison of NbALFA with Three Humanized NbALFA Variants

Aim of the experiment was to perform a comparison of wtNbALFA (SEQ ID NO: 1) with three humanized NbALFA variants (SEQ ID NO: 123 (Variant 13), SEQ ID NO: 121 (Variant 11), and SEQ ID NO: 35 of US2023/0093123A1 ("US2023/0093123A1-Seq35", SEQ ID NO: 129 of the present disclosure) regarding their relative expression levels and glycosylation pattern upon expression in a mammalian expression system (HEK293/ExPi293).

For a direct side-by-side comparison, all four NbALFA variants were expressed, purified and analyzed in parallel using identical settings.

The experiment shows that the humanized Variants 13 and 11 show slightly higher expression levels and yields than wtNbALFA (Table 8).

TABLE 8

| Comparison of yields obtained for four NbALFA variants | | | |
|---|---|---|---|
| | | Yield per liter of culture (mg) | |
| NbALFA variant | Plasmid | Raw | SEC |
| wtNbALFA | pNT3980 | 66.9 | 54.9 |
| Variant 13 | pNT3916 | 93.2 | 72.5 |
| Variant 11 | pNT4220 | 80.2 | 66.2 |
| US2023/0093123A1-Seq35 | pNT4118 | 16.0 4.0 (peak 1) | 10.8 (peak 2) |

All these three variants show very homogeneous behavior when analyzed by SDS-PAGE gels (FIG. 4, A-C) and size exclusion chromatography (FIG. 4, D).

In comparison, the yield of US2023/0093123A1-Seq35 clearly lacks behind all other NbALFA variants analyzed in this experiment (Table 8). US2023/0093123A1-Seq35 is also the only variant showing two distinct species on SDS gels (FIG. 4, A+C), which can clearly be separated by size exclusion chromatography (FIG. 4, D). Judged from its more diffuse appearance on SDS gels, the respective upper band (corresponding to SEC peak 1) can be attributed to a glycosylated species. The SEC elution volume of ~14 mL found for species corresponding to the lower band found on SDS gels is consistent with the other NbALFA variants not showing any second species when analyzed by SDS-PAGE. The minute peaks observed for the humanized Variants 13 and 11 at elution volumes ~12.5 mL most likely correspond to transient dimeric forms, which are often observed when analyzing single-domain antibodies by SEC.

The glycosylation observed for US2023/0093123A1-Seq35 is consistent with the fact that it is the only analyzed NbALFA variant possessing a consensus glycosylation site (Protein sequence EVQLQESGGGLVQAGGSLRLSC-TASGVTISALNAMAMGWYRQAPGKRRVMV-AAVSERGNT MYRESVKGRFTVSRDFTNKTVYL-QMNSLKPEDTAVYYCHVLEDRVDSFHDYWGQGT-QVTVS S, NXT-type consensus glycosylate site bold underlined, (SEQ ID NO: 129).

Example 6: Comparison of Thermal Stability of Humanized NbALFA Variants to the Wild Type NbALFA and Another NbALFA Variant The thermal stability of Variant 13 (SEQ ID NO: 123), wild type NbALFA (SEQ ID NO: 1) and SEQ ID NO: 35 of US2023/0093123A1 (SEQ ID NO: 129) after production in mammalian cells were investigated. In general, higher thermal stabilities of the VHHs were observed when compared in a mammalian production system as compared to procaryotic expression systems (Table 5, Table 5). While the Variant 13 exhibits a significantly higher thermal stability compared to the wildtype NbALFA, SEQ ID NO: 35 of US2023/0093123A1 showed only a marginal improvement over its parental counterpart. In direct comparison, SEQ ID NO: 35 of US2023/0093123A1 exhibited a significantly lower thermal stability compared to the Variant 13.

TABLE 9

| Determination of thermal stability of VHH derived from a mammalian production system | |
|---|---|
| Variant # | Tm [° C.] |
| wtNbALFA (Seq ID No: 1) | 62.60 |
| Variant 13 (SEQ ID NO: 123) | 68.26 |
| US2023/0093123A1-Seq35 (SEQ ID NO: 129) | 64.85 |

Example 7: Comparison of Human Germline Identity with Antibodies which Received an International Nonproprietary Name (INN)

Antibodies are often assigned official and generic names known as International Nonproprietary Names (INN) during early-stage clinical trials. Prior to 2017, these names included infixes indicating the sequence source of the antibody. Those included -u- (human), -xi- (chimeric), -zu- (humanized), -xizu-(chimeric/humanized) (Source: Wilkinson and Hale, 2022 (DOI: 10.1080/19420862.2022.2123299)). While this nomenclature was discontinued and was replaced by a naming convention less focused on the origin of the sequence and more on the engineering done on the sequence, the original infixes allow to determine which antibodies were officially considered humanized. The "Supplementary Table 2" of the Wilkinson and Hale, 2022 (DOI: 10.1080/19420862.2022.2123299) publication listed sequences of antibodies which received INNs. Those were filtered to comprise only those antibodies which fall under the category of being of the "mAb" Typ, exhibiting an "IgG" format and being of the "hulgG1" isotype. The sequence of "Protein 1", being the antibody heavy chain, was extracted and constant domains removed. Finally, of the remaining 339 VHs, the sequences were categorized into five classes: -u- (human), -xi- (chimeric), -zu- (humanized), -xizu- (chimeric/humanized) and uncategorized (no infix of the beforementioned ones). For all these sequences, the highest human V segment identity to an IGHV germline was determined and plotted in a violin plot (FIG. 5).

The descriptive statistics of these germline homology values yielded mean and percentile values in an infix-dependent manner. This allows to compare the humanized NbALFA antibodies with other humanized molecules known in the art (Table 10).

TABLE 10

Descriptive statistics of infixes of 339 VH sequences in relation to V-Segment identity.

| | -xi-mab | -xi-zu-mab | -zu-mab | -u-mab | Uncategorized | All |
|---|---|---|---|---|---|---|
| Number of antibodies | 28 | 5 | 86 | 74 | 146 | 339 |
| Minimum | 57.6 | 68.0 | 70.4 | 78.6 | 66.3 | 57.6 |
| 25% Percentile | 63.55 | 74.70 | 79.35 | 90.55 | 82.65 | 80.6 |
| Median | 67.85 | 84.50 | 83.15 | 94.80 | 88.80 | 87.60 |
| 75% Percentile | 74.50 | 92.35 | 86.90 | 96.23 | 93.90 | 93.80 |

TABLE 10-continued

| Descriptive statistics of infixes of 339 VH sequences in relation to V-Segment identity. | | | | | | |
|---|---|---|---|---|---|---|
| | -xi-mab | -xi-zu-mab | -zu-mab | -u-mab | Uncategorized | All |
| Maximum | 87.9 | 92.9 | 94.9 | 100 | 100 | 100 |
| Range | 30.3 | 24.9 | 24.5 | 21.4 | 33.7 | 42.4 |
| Mean | 69.16 | 83.72 | 83.2 | 93.46 | 87.81 | 86.27 |
| Std. Deviation | 7.452 | 10.030 | 5.475 | 4.375 | 7.213 | 8.870 |
| Std. Error of Mean | 1.4080 | 4.4870 | 0.5903 | 0.5086 | 0.5970 | 0.4818 |

Antibodies comprising the -xi-mab infix are defined as being chimeric. In these molecules the variable regions are grafted onto human constant domains (e.g. murine VH, human CH1-CH3). In the analyzed data set, the lowest human germline identity of such a non-humanized antibody was 57.6%, which was only marginally lower than the human V-segment identity of wtNbALFA (59.6%). Therefore, the wtNbALFA was even for chimeric standards quite distant from the human germline. The SEQ ID NO: 35 of US2023/0093123 exhibited a human V segment identity of 66.7% which was very close to the median value of chimeric antibodies analyzed in this data set (67.85%). Accordingly, SEQ ID NO: 35 of US2023/0093123 cannot be considered a humanized antibody and falls clearly under the chimeric umbrella.

The -xi-zu-mab infix was utilized for chimeric/humanized hybrid antibodies. In those, the VH was humanized while the VL sequence remained unchanged from the parental, animal-derived, sequence. As herein only VH sequences were analyzed due to their higher homology with VHHs, this class was also considered to represent "humanized antibodies". The wtNbALFA and the SEQ ID NO: 35 of US2023/0093123 fail to reach the minimum value of 68.0%, while Variant 11 (73.7%) was located within the first quarter of sequences. The Variant 13 (76.8%) and Variant 15 (80.8%) were even found within the second quarter of sequences, less than one standard deviation distant to the mean value.

Humanized antibodies, exhibiting the -zu-mab infix, happen to have V-segment identities starting form 70.4%. While Variant 11 (73.7%) and Variant 13 (76.8%) fell in the first quarter of this class, wtNbALFA (59.6%) and SEQ ID NO: 35 of US2023/0093123 (66.7%) were again clearly below the found minimum. Further, Variant 15 (80.8%) even reached the second quarter while being less than one standard deviation distant from the mean value of V-segment identity of humanized antibodies. Accordingly, all three antibodies are classified as being similar in V-segment identity as humanized antibodies gaining an INN classification. Even the least humanized candidate presented in this application, Variant 8 (72.7%), exhibited a V-segment identity above the minimum found in-zu-mab classified antibodies.

Antibodies from human origin exhibit an -u-mab infix. The range in the V-segment identity can therefore be considered as the mutational space that somatic hypermutation can utilize to generate a diverse set of human antibodies. While the minimal observed V-segment identity was 78.6%, Variant 15 even occupies the first quarter of this infix class underlining its status as a humanized antibody.

The uncategorized sequences exhibited another naming scheme, devoid of species- or humanization-dependent infixes. While it was not possible to classify antibodies as humanized or human based on that, it was obvious that the wtNbALFA was significantly lower in V-segment identity compared to the minimum value observed for antibodies in this class. While US2023/0093123A1-Seq35 (66.7%) was only marginally above the minimum threshold of 66.3%, all humanized antibodies presented in this application occupy the first quarter of sequences.

Example 8: Methods

Method 1: Affinity Determination

To determine the affinity of humanized NbALFA variants to the epitope tag of SEQ ID NO: 2, an Octet RED96 or an Octet HTX from ForteBio was utilized. The measurement principle is based on biolayer interferometry (BLI). SAX2.0 biosensors were soaked for 10 min in kinetic buffer (KB), supplied by the manufacturer of the instrument. At first, a 60 or 120 sec baseline in KB was measured, followed by a loading step of 240 sec with 83 ng/ml of biotinylated peptide of SEQ ID NO: 2. After loading, free streptavidin entities on the biosensor were quenched during a 120 sec incubation step in a 100 μg/ml biocytin solution. Subsequently, a 60 to 600 sec baseline in KB was measured followed by association of the VHH. The VHH was applied with a maximal concentration of 10 nM and was 1:1 serial diluted in KB. As a reference, only KB was measured. Association was performed for 900 sec, followed by a dissociation time of 1500 sec in KB. The signal of the reference well was subtracted from the signal of all other biosensors and the signals of these processed data were aligned to the average of the second baseline. For inter-step correction, the data were aligned to the dissociation step and Savitzky-Golay filtering was applied to all curves. Association and dissociations were globally fitted using a 1:1 Langmuir binding model.

Method 2: Thermal Stability Analysis

Thermal stability was investigated using the Prometheus Tycho from Nano Temper. 10 μl of a VHH sample was loaded into capillaries. After loading the capillaries into the instrument, a heat ramp of 30° C./min from 35° C. to 95° C. was applied to all samples. During this process the intrinsic fluorescence of the proteins were measured at 350 nm and 330 nm. The ratio was plotted against the temperature and the first derivative was calculated. Minima and maxima correspond to different TM values that are observed in the process of denaturation.

Method 3: SEC Analysis

Aggregation analysis was performed via SEC utilizing an Agilent Infinity II HPLC and a Biozen 1.8 μm dSEC-2, 200 Å LC column (300×4.6 mm). Flowrates were adjusted to 0.25 mL/min, resulting in approximately 255 bar pressure. As mobile phase 0.2 M potassium phosphate, 250 mM KCl, pH 6.2, 5% acetonitrile was used. Each run took 20 min excluding a 2-3 min wash step between each analysis. 10 μL of the VHH proteins were applied and detected by absorption at 280 nm.

Method 4: SpA Binding Determination

45 μg of the purified VHHs were diluted in 200 μL of CHO cell culture supernatant. SpA HP Spin Trap columns from Cytiva were equilibrated once with 600 μL of PBS and subsequently the 200 μL sample was applied and incubated according to the manufactures protocol. Subsequently two washing steps with 600 μL of PBS were performed followed by two elution steps with 400 μL of 100 mM Glycin pH 2.7. Of the VHH in the CHO supernatant, the flow through the two wash steps and the two elution fractions SDS-PAGE analysis was performed.

Method 5: Protein Expression (Example 5)

In parallel side-by-side experiments, 100 mL Expi293 cells per experiment were transiently transfected with analogous eukaryotic expression vectors encoding NbALFA variants under the control of a CMV promoter. For this, Expi 293 cells, cultured in Expi293 Medium (Gibco) were set up at a concentration of $3*10^6$ cells/mL. For a 100 mL transfection volume, 50 μg of plasmid DNA was diluted in 10 mL OptiMEM (Gibco) and then added to 50 μL FectoPro transfection reagent (Polyplus). The mixture was incubated at RT for 10 min and then added to 90 mL Expi293 cells. After one hour, 50 μL booster (FectoPro Kit) was added. The cells were cultured at 37° C., 8% CO2, 85% humidity and 100 rpm. After 5 days, culture supernatants were harvested by centrifugation.

Method 6: Protein Purification (Example 5)

Culture supernatants were filtered through a 0.45 μm membrane and applied by gravity flow to 2 mL of an agarose resin featuring a low-affinity ALFA-like peptide (NanoTag Biotechnologies, #N1530-ALP3). The resin was washed with >10 column volumes of PBS. Bound proteins were eluted with pH3 buffer (100 mM sodium citrate, 100 mM NaCl, pH3.0) and immediately neutralized by addition of 1/10 volume 1 M Tris-HCl pH8.5. Raw eluates obtained from the ALP3 agarose resin were concentrated to 1 mL using a 3 kDa cutoff spin filter (Amicon Ultra-4, Merck) and further purified using an Äkta Pure system (Cytiva) equipped with a Superdex 75 increase 10/30 column (Cytiva) equilibrated with PBS.

Method 7: Protein Quantification (Example 5)

Proteins were quantified by UV absorbance using their specific extinction coefficients at 280 nm.

Method 8: Protein Analysis (Example 5)

Relevant protein fractions were analyzed by SDS-PAGE using pre-cast gels (Bolt 4 to 12%, Bis-Tris gels, Thermo Scientific, #NWO4127BOX). The gels were stained with Coomassie brilliant blue.

Embodiments illustratively described herein may suitably be practiced in the absence of any element or elements, limitation or limitations, not specifically disclosed herein. Thus, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group.

Equivalents: Those skilled in the art will recognize or be able to ascertain using no more than routine experimentation, many equivalents to the specific embodiments of the invention described herein. Such equivalents are intended to be encompassed by the following claims.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent applications, scientific publications, manufacturer's specifications, instructions, etc.) are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

Further embodiments will become apparent from the following claims.

The invention claimed is:

1. A humanized single-domain antibody that specifically binds to an epitope tag comprising the sequence SRLEEELRRRLTE (SEQ ID NO: 2), wherein the antibody comprises the amino acid sequence of SEQ ID NO: 119, SEQ ID NO: 120, SEQ ID NO: 121, SEQ ID NO: 122, SEQ ID NO: 123, SEQ ID NO: 124, or SEQ ID NO: 125.

2. The antibody of claim 1, wherein the antibody comprises the amino acid sequence of SEQ ID NO: 119.

3. The antibody of claim 1, wherein the antibody comprises the amino acid sequence of SEQ ID NO: 120.

4. The antibody of claim 1, wherein the antibody comprises the amino acid sequence of SEQ ID NO: 121.

5. The antibody of claim 1, wherein the antibody comprises the amino acid sequence of SEQ ID NO: 122.

6. The antibody of claim 1, wherein the antibody comprises the amino acid sequence of SEQ ID NO: 123.

7. The antibody of claim 1, wherein the antibody comprises the amino acid sequence of SEQ ID NO: 124.

8. The antibody of claim 1, wherein the antibody comprises the amino acid sequence of SEQ ID NO: 125.

9. A fusion protein comprising the antibody of claim 1 and a peptide or a protein fusion partner.

10. A nucleic acid encoding a humanized antibody of claim 1.

11. A vector comprising the nucleic acid of claim 10.

12. A method of producing an antibody of comprising cultivating a host cell comprising the vector of claim 11 under conditions allowing the expression of the antibody encoded by the vector.

13. A host cell comprising the nucleic acid of claim 10.

14. A method of producing an antibody of comprising cultivating a host cell comprising the nucleic acid of claim 10 under conditions allowing the expression of the antibody encoded by the nucleic acid.

15. A method of binding a protein comprising the amino acid sequence of SRLEEELRRRLTE (SEQ ID NO: 2), comprising contacting the protein with the humanized antibody of claim 1.

16. A method according to claim 15, further comprising detecting binding of the humanized antibody to the protein.

17. A method according to claim 16, wherein the humanized antibody is conjugated to a detectable label and the detecting step comprises detecting a signal from the detectable label.

* * * * *

SEQUENCE LISTING

```
Sequence total quantity: 129
SEQ ID NO: 1            moltype = AA  length = 122
FEATURE                 Location/Qualifiers
source                  1..122
                        mol_type = protein
                        organism = Synthetic construct
SEQUENCE: 1
EVQLQESGGG LVQPGGSLRL SCTASGVTIS ALNAMAMGWY RQAPGERRVM VAAVSERGNA  60
MYRESVQGRF TVTRDFTNKM VSLQMDNLKP EDTAVYYCHV LEDRVDSFHD YWGQGTQVTV  120
```

-continued

```
SS                                                                   122

SEQ ID NO: 2            moltype = AA  length = 13
FEATURE                 Location/Qualifiers
source                  1..13
                        mol_type = protein
                        organism = Synthetic construct
SEQUENCE: 2
SRLEEELRRR LTE                                                       13

SEQ ID NO: 3            moltype = AA  length = 13
FEATURE                 Location/Qualifiers
source                  1..13
                        mol_type = protein
                        organism = Synthetic construct
SITE                    1
                        note = X is G or S or P or T
SITE                    2
                        note = X is R or G or P
SITE                    12
                        note = X is S or T or P or A or D or E
SITE                    13
                        note = X is P or A or S or K or D or E or no amino acid
SEQUENCE: 3
XXLEZEJRRR LXX                                                       13

SEQ ID NO: 4            moltype = AA  length = 13
FEATURE                 Location/Qualifiers
source                  1..13
                        mol_type = protein
                        organism = Synthetic construct
SITE                    1
                        note = X is S or T
SITE                    2
                        note = X is R or G
SITE                    12
                        note = X is T or D
SITE                    13
                        note = X is A or D or E or no amino acid
SEQUENCE: 4
XXLEZELRRR LXX                                                       13

SEQ ID NO: 5            moltype = AA  length = 16
FEATURE                 Location/Qualifiers
source                  1..16
                        mol_type = protein
                        organism = Synthetic construct
SEQUENCE: 5
MPSRLEEELR RRLTEP                                                    16

SEQ ID NO: 6            moltype = AA  length = 15
FEATURE                 Location/Qualifiers
source                  1..15
                        mol_type = protein
                        organism = Synthetic construct
SEQUENCE: 6
PSRLEEELRR RLTEP                                                     15

SEQ ID NO: 7            moltype = AA  length = 14
FEATURE                 Location/Qualifiers
source                  1..14
                        mol_type = protein
                        organism = Synthetic construct
SEQUENCE: 7
PSRLEEELRR RLTE                                                      14

SEQ ID NO: 8            moltype = AA  length = 15
FEATURE                 Location/Qualifiers
source                  1..15
                        mol_type = protein
                        organism = Synthetic construct
SEQUENCE: 8
GRSRLEEELR RRLTA                                                     15

SEQ ID NO: 9            moltype = AA  length = 16
FEATURE                 Location/Qualifiers
source                  1..16
                        mol_type = protein
                        organism = Synthetic construct
```

-continued

```
SEQUENCE: 9
PGSRLEEELR RRLTAP                                                    16

SEQ ID NO: 10           moltype = AA  length = 16
FEATURE                 Location/Qualifiers
source                  1..16
                        mol_type = protein
                        organism = Synthetic construct
SEQUENCE: 10
PSTRLEEELR RRLTAP                                                    16

SEQ ID NO: 11           moltype = AA  length = 16
FEATURE                 Location/Qualifiers
source                  1..16
                        mol_type = protein
                        organism = Synthetic construct
SEQUENCE: 11
SPSRLEEELR RRLTAP                                                    16

SEQ ID NO: 12           moltype = AA  length = 16
FEATURE                 Location/Qualifiers
source                  1..16
                        mol_type = protein
                        organism = Synthetic construct
SEQUENCE: 12
SPSRLEEELR RRLDAP                                                    16

SEQ ID NO: 13           moltype = AA  length = 16
FEATURE                 Location/Qualifiers
source                  1..16
                        mol_type = protein
                        organism = Synthetic construct
SEQUENCE: 13
SPSRLEEELR RRLEAP                                                    16

SEQ ID NO: 14           moltype = AA  length = 16
FEATURE                 Location/Qualifiers
source                  1..16
                        mol_type = protein
                        organism = Synthetic construct
SEQUENCE: 14
SPSRLEEELR RRLTDP                                                    16

SEQ ID NO: 15           moltype = AA  length = 16
FEATURE                 Location/Qualifiers
source                  1..16
                        mol_type = protein
                        organism = Synthetic construct
SEQUENCE: 15
SPSRLEEELR RRLTEP                                                    16

SEQ ID NO: 16           moltype = AA  length = 17
FEATURE                 Location/Qualifiers
source                  1..17
                        mol_type = protein
                        organism = Synthetic construct
SEQUENCE: 16
SPSRLEEELR RRLTADP                                                   17

SEQ ID NO: 17           moltype = AA  length = 16
FEATURE                 Location/Qualifiers
source                  1..16
                        mol_type = protein
                        organism = Synthetic construct
SEQUENCE: 17
SPSGLEEELR RRLTEP                                                    16

SEQ ID NO: 18           moltype = AA  length = 14
FEATURE                 Location/Qualifiers
source                  1..14
                        mol_type = protein
                        organism = Synthetic construct
SEQUENCE: 18
GPSRLEEELR RRLT                                                      14

SEQ ID NO: 19           moltype = AA  length = 15
FEATURE                 Location/Qualifiers
source                  1..15
                        mol_type = protein
```

```
                        organism = Synthetic construct
SEQUENCE: 19
GPSRLEEELR RRLTA                                                   15

SEQ ID NO: 20           moltype = AA  length = 16
FEATURE                 Location/Qualifiers
source                  1..16
                        mol_type = protein
                        organism = Synthetic construct
SEQUENCE: 20
GPSRLEEELR RRLTAA                                                  16

SEQ ID NO: 21           moltype = AA  length = 17
FEATURE                 Location/Qualifiers
source                  1..17
                        mol_type = protein
                        organism = Synthetic construct
SEQUENCE: 21
GPSRLEEELR RRLTAAS                                                 17

SEQ ID NO: 22           moltype = AA  length = 16
FEATURE                 Location/Qualifiers
source                  1..16
                        mol_type = protein
                        organism = Synthetic construct
SEQUENCE: 22
SPSGLEQELR RRLTAP                                                  16

SEQ ID NO: 23           moltype = AA  length = 16
FEATURE                 Location/Qualifiers
source                  1..16
                        mol_type = protein
                        organism = Synthetic construct
SEQUENCE: 23
SPSGLEQELR RRLDAP                                                  16

SEQ ID NO: 24           moltype = AA  length = 16
FEATURE                 Location/Qualifiers
source                  1..16
                        mol_type = protein
                        organism = Synthetic construct
SEQUENCE: 24
SPSGLEQELR RRLEAP                                                  16

SEQ ID NO: 25           moltype = AA  length = 16
FEATURE                 Location/Qualifiers
source                  1..16
                        mol_type = protein
                        organism = Synthetic construct
SEQUENCE: 25
SPSGLEQELR RRLTEP                                                  16

SEQ ID NO: 26           moltype = AA  length = 16
FEATURE                 Location/Qualifiers
source                  1..16
                        mol_type = protein
                        organism = Synthetic construct
SEQUENCE: 26
GPSRLEEELR RRLTAP                                                  16

SEQ ID NO: 27           moltype = AA  length = 16
FEATURE                 Location/Qualifiers
source                  1..16
                        mol_type = protein
                        organism = Synthetic construct
SEQUENCE: 27
GPSRLEEELR RRLTEP                                                  16

SEQ ID NO: 28           moltype = AA  length = 15
FEATURE                 Location/Qualifiers
source                  1..15
                        mol_type = protein
                        organism = Synthetic construct
SEQUENCE: 28
GPSRLEEELR RRLTE                                                   15

SEQ ID NO: 29           moltype = AA  length = 15
FEATURE                 Location/Qualifiers
source                  1..15
```

```
                        mol_type = protein
                        organism = Synthetic construct
SEQUENCE: 29
MSRLEEELRR RLTEP                                                15

SEQ ID NO: 30           moltype = AA  length = 16
FEATURE                 Location/Qualifiers
source                  1..16
                        mol_type = protein
                        organism = Synthetic construct
SEQUENCE: 30
MSSRLEEELR RRLTEP                                               16

SEQ ID NO: 31           moltype = AA  length = 13
FEATURE                 Location/Qualifiers
source                  1..13
                        mol_type = protein
                        organism = Synthetic construct
SITE                    1
                        note = X is G or S or P
SITE                    2
                        note = X is R or G
SITE                    12
                        note = X is S or T or P or A
SITE                    13
                        note = X is P or A or S or no amino acid
SEQUENCE: 31
XXLEZEJRRR LXX                                                  13

SEQ ID NO: 32           moltype = AA  length = 12
FEATURE                 Location/Qualifiers
source                  1..12
                        mol_type = protein
                        organism = Synthetic construct
SEQUENCE: 32
GRLEEELRRR LS                                                   12

SEQ ID NO: 33           moltype = AA  length = 15
FEATURE                 Location/Qualifiers
source                  1..15
                        mol_type = protein
                        organism = Synthetic construct
SEQUENCE: 33
MSGRLEEELR RRLSP                                                15

SEQ ID NO: 34           moltype = AA  length = 16
FEATURE                 Location/Qualifiers
source                  1..16
                        mol_type = protein
                        organism = Synthetic construct
SEQUENCE: 34
SDSGLEQELR RRLSPG                                               16

SEQ ID NO: 35           moltype = AA  length = 16
FEATURE                 Location/Qualifiers
source                  1..16
                        mol_type = protein
                        organism = Synthetic construct
SEQUENCE: 35
PDGGLEQELR RRLTAP                                               16

SEQ ID NO: 36           moltype = AA  length = 16
FEATURE                 Location/Qualifiers
source                  1..16
                        mol_type = protein
                        organism = Synthetic construct
SEQUENCE: 36
PSGGLEQELR RRLTAP                                               16

SEQ ID NO: 37           moltype = AA  length = 16
FEATURE                 Location/Qualifiers
source                  1..16
                        mol_type = protein
                        organism = Synthetic construct
SEQUENCE: 37
DSPGLEQELR RRLTAP                                               16

SEQ ID NO: 38           moltype = AA  length = 16
FEATURE                 Location/Qualifiers
```

```
source                  1..16
                        mol_type = protein
                        organism = Synthetic construct
SEQUENCE: 38
PDSGLEQELR RRLTPA                                                   16

SEQ ID NO: 39           moltype = AA  length = 17
FEATURE                 Location/Qualifiers
source                  1..17
                        mol_type = protein
                        organism = Synthetic construct
SEQUENCE: 39
SPSGLEEELR RRLTAEP                                                  17

SEQ ID NO: 40           moltype = AA  length = 14
FEATURE                 Location/Qualifiers
source                  1..14
                        mol_type = protein
                        organism = Synthetic construct
SEQUENCE: 40
GPSGLEQELR RRLT                                                     14

SEQ ID NO: 41           moltype = AA  length = 17
FEATURE                 Location/Qualifiers
source                  1..17
                        mol_type = protein
                        organism = Synthetic construct
SEQUENCE: 41
GPSGLEQELR RRLTAAS                                                  17

SEQ ID NO: 42           moltype = AA  length = 16
FEATURE                 Location/Qualifiers
source                  1..16
                        mol_type = protein
                        organism = Synthetic construct
SEQUENCE: 42
SPSRLEEELR RRLPSK                                                   16

SEQ ID NO: 43           moltype = AA  length = 16
FEATURE                 Location/Qualifiers
source                  1..16
                        mol_type = protein
                        organism = Synthetic construct
SEQUENCE: 43
SPSGLEQELR RRLTPS                                                   16

SEQ ID NO: 44           moltype = AA  length = 16
FEATURE                 Location/Qualifiers
source                  1..16
                        mol_type = protein
                        organism = Synthetic construct
SEQUENCE: 44
SPGRLEQEIR RRLSPS                                                   16

SEQ ID NO: 45           moltype = AA  length = 16
FEATURE                 Location/Qualifiers
source                  1..16
                        mol_type = protein
                        organism = Synthetic construct
SEQUENCE: 45
PSGRLEEELR RRLSPS                                                   16

SEQ ID NO: 46           moltype = AA  length = 14
FEATURE                 Location/Qualifiers
source                  1..14
                        mol_type = protein
                        organism = Synthetic construct
SEQUENCE: 46
PSGRLEEELR RRLS                                                     14

SEQ ID NO: 47           moltype = AA  length = 14
FEATURE                 Location/Qualifiers
source                  1..14
                        mol_type = protein
                        organism = Synthetic construct
SEQUENCE: 47
PSGRLEEELR RRLA                                                     14

SEQ ID NO: 48           moltype = AA  length = 15
```

```
FEATURE                Location/Qualifiers
source                 1..15
                       mol_type = protein
                       organism = Synthetic construct
SEQUENCE: 48
PSGRLEEELR RRLSP                                                    15

SEQ ID NO: 49          moltype = AA  length = 13
FEATURE                Location/Qualifiers
source                 1..13
                       mol_type = protein
                       organism = Synthetic construct
SITE                   1
                       note = X is S or G or P
SITE                   2
                       note = X is R or G or P
SITE                   12
                       note = X is S or T or D or E
SITE                   13
                       note = X is P or A or D or no amino acid
SEQUENCE: 49
XXLEZELRRR LXX                                                      13

SEQ ID NO: 50          moltype = AA  length = 16
FEATURE                Location/Qualifiers
source                 1..16
                       mol_type = protein
                       organism = Synthetic construct
SEQUENCE: 50
PDSGLEQELR RRLSPG                                                   16

SEQ ID NO: 51          moltype = AA  length = 16
FEATURE                Location/Qualifiers
source                 1..16
                       mol_type = protein
                       organism = Synthetic construct
SEQUENCE: 51
PDSGLEQELR RRLTAP                                                   16

SEQ ID NO: 52          moltype = AA  length = 16
FEATURE                Location/Qualifiers
source                 1..16
                       mol_type = protein
                       organism = Synthetic construct
SEQUENCE: 52
PSSGLEQELR RRLTAP                                                   16

SEQ ID NO: 53          moltype = AA  length = 16
FEATURE                Location/Qualifiers
source                 1..16
                       mol_type = protein
                       organism = Synthetic construct
SEQUENCE: 53
DPSGLEQELR RRLTAP                                                   16

SEQ ID NO: 54          moltype = AA  length = 16
FEATURE                Location/Qualifiers
source                 1..16
                       mol_type = protein
                       organism = Synthetic construct
SEQUENCE: 54
DSGPLEQELR RRLTAP                                                   16

SEQ ID NO: 55          moltype = AA  length = 17
FEATURE                Location/Qualifiers
source                 1..17
                       mol_type = protein
                       organism = Synthetic construct
SEQUENCE: 55
SPSRLEEELR RRLTAEP                                                  17

SEQ ID NO: 56          moltype = AA  length = 16
FEATURE                Location/Qualifiers
source                 1..16
                       mol_type = protein
                       organism = Synthetic construct
SEQUENCE: 56
SPSGLEEELR RRLTAP                                                   16
```

```
SEQ ID NO: 57           moltype = AA  length = 16
FEATURE                 Location/Qualifiers
source                  1..16
                        mol_type = protein
                        organism = Synthetic construct
SEQUENCE: 57
SPSGLEEELR RRLDAP                                                   16

SEQ ID NO: 58           moltype = AA  length = 16
FEATURE                 Location/Qualifiers
source                  1..16
                        mol_type = protein
                        organism = Synthetic construct
SEQUENCE: 58
SPSGLEEELR RRLEAP                                                   16

SEQ ID NO: 59           moltype = AA  length = 16
FEATURE                 Location/Qualifiers
source                  1..16
                        mol_type = protein
                        organism = Synthetic construct
SEQUENCE: 59
SPSGLEEELR RRLTDP                                                   16

SEQ ID NO: 60           moltype = AA  length = 17
FEATURE                 Location/Qualifiers
source                  1..17
                        mol_type = protein
                        organism = Synthetic construct
SEQUENCE: 60
SPSGLEEELR RRLTADP                                                  17

SEQ ID NO: 61           moltype = AA  length = 15
FEATURE                 Location/Qualifiers
source                  1..15
                        mol_type = protein
                        organism = Synthetic construct
SEQUENCE: 61
GPSGLEQELR RRLTA                                                    15

SEQ ID NO: 62           moltype = AA  length = 16
FEATURE                 Location/Qualifiers
source                  1..16
                        mol_type = protein
                        organism = Synthetic construct
SEQUENCE: 62
SPSGLEQELR RRLTDP                                                   16

SEQ ID NO: 63           moltype = AA  length = 17
FEATURE                 Location/Qualifiers
source                  1..17
                        mol_type = protein
                        organism = Synthetic construct
SEQUENCE: 63
SPSGLEQELR RRLTADP                                                  17

SEQ ID NO: 64           moltype = AA  length = 17
FEATURE                 Location/Qualifiers
source                  1..17
                        mol_type = protein
                        organism = Synthetic construct
SEQUENCE: 64
SPSGLEQELR RRLTAEP                                                  17

SEQ ID NO: 65           moltype = AA  length = 16
FEATURE                 Location/Qualifiers
source                  1..16
                        mol_type = protein
                        organism = Synthetic construct
SEQUENCE: 65
SPSGLEQELR RRLSPS                                                   16

SEQ ID NO: 66           moltype =   length =
SEQUENCE: 66
000

SEQ ID NO: 67           moltype = AA  length = 16
FEATURE                 Location/Qualifiers
source                  1..16
```

```
                        mol_type = protein
                        organism = Synthetic construct
SEQUENCE: 67
DSGRLEEELR RRLSKG                                                     16

SEQ ID NO: 68           moltype = AA  length = 16
FEATURE                 Location/Qualifiers
source                  1..16
                        mol_type = protein
                        organism = Synthetic construct
SEQUENCE: 68
DSGRLEEELR RRLSPG                                                     16

SEQ ID NO: 69           moltype = AA  length = 16
FEATURE                 Location/Qualifiers
source                  1..16
                        mol_type = protein
                        organism = Synthetic construct
SEQUENCE: 69
SDSGLEEELR RRLSPG                                                     16

SEQ ID NO: 70           moltype = AA  length = 16
FEATURE                 Location/Qualifiers
source                  1..16
                        mol_type = protein
                        organism = Synthetic construct
SEQUENCE: 70
SDSGVEEELR RRLSPG                                                     16

SEQ ID NO: 71           moltype = AA  length = 16
FEATURE                 Location/Qualifiers
source                  1..16
                        mol_type = protein
                        organism = Synthetic construct
SEQUENCE: 71
SDSAVEEELR RRLSPG                                                     16

SEQ ID NO: 72           moltype = AA  length = 16
FEATURE                 Location/Qualifiers
source                  1..16
                        mol_type = protein
                        organism = Synthetic construct
SEQUENCE: 72
SDSGLQEELR RRLSPG                                                     16

SEQ ID NO: 73           moltype = AA  length = 16
FEATURE                 Location/Qualifiers
source                  1..16
                        mol_type = protein
                        organism = Synthetic construct
SEQUENCE: 73
SDSGLEEQLR RRLSPG                                                     16

SEQ ID NO: 74           moltype = AA  length = 16
FEATURE                 Location/Qualifiers
source                  1..16
                        mol_type = protein
                        organism = Synthetic construct
SEQUENCE: 74
SDSGLEEEIR RRLSPG                                                     16

SEQ ID NO: 75           moltype = AA  length = 16
FEATURE                 Location/Qualifiers
source                  1..16
                        mol_type = protein
                        organism = Synthetic construct
SEQUENCE: 75
SDSGLEEEVR RRLSPG                                                     16

SEQ ID NO: 76           moltype = AA  length = 16
FEATURE                 Location/Qualifiers
source                  1..16
                        mol_type = protein
                        organism = Synthetic construct
SEQUENCE: 76
DSGELEEELR RRLSPG                                                     16

SEQ ID NO: 77           moltype = AA  length = 16
FEATURE                 Location/Qualifiers
```

```
source                  1..16
                        mol_type = protein
                        organism = Synthetic construct
SEQUENCE: 77
DSGRLEQELR RRLSPG                                                         16

SEQ ID NO: 78           moltype = AA  length = 16
FEATURE                 Location/Qualifiers
source                  1..16
                        mol_type = protein
                        organism = Synthetic construct
SEQUENCE: 78
DSGRLEEEIR RRLSPG                                                         16

SEQ ID NO: 79           moltype = AA  length = 16
FEATURE                 Location/Qualifiers
source                  1..16
                        mol_type = protein
                        organism = Synthetic construct
SEQUENCE: 79
DSGRLEQEIR RRLSPG                                                         16

SEQ ID NO: 80           moltype = AA  length = 16
FEATURE                 Location/Qualifiers
source                  1..16
                        mol_type = protein
                        organism = Synthetic construct
SEQUENCE: 80
DSGRLEQEIA RRLSPG                                                         16

SEQ ID NO: 81           moltype = AA  length = 16
FEATURE                 Location/Qualifiers
source                  1..16
                        mol_type = protein
                        organism = Synthetic construct
SEQUENCE: 81
DSGRLEQEIQ RRLSPG                                                         16

SEQ ID NO: 82           moltype = AA  length = 16
FEATURE                 Location/Qualifiers
source                  1..16
                        mol_type = protein
                        organism = Synthetic construct
SEQUENCE: 82
DSGRLEQEIE RRLSPG                                                         16

SEQ ID NO: 83           moltype = AA  length = 16
FEATURE                 Location/Qualifiers
source                  1..16
                        mol_type = protein
                        organism = Synthetic construct
SEQUENCE: 83
DSGRLEQEIR ARLSPG                                                         16

SEQ ID NO: 84           moltype = AA  length = 16
FEATURE                 Location/Qualifiers
source                  1..16
                        mol_type = protein
                        organism = Synthetic construct
SEQUENCE: 84
DSGRLEQEIR QRLSPG                                                         16

SEQ ID NO: 85           moltype = AA  length = 16
FEATURE                 Location/Qualifiers
source                  1..16
                        mol_type = protein
                        organism = Synthetic construct
SEQUENCE: 85
DSGRLEQEIR ERLSPG                                                         16

SEQ ID NO: 86           moltype = AA  length = 13
FEATURE                 Location/Qualifiers
source                  1..13
                        mol_type = protein
                        organism = Synthetic construct
SEQUENCE: 86
GPSRLEEELR RRL                                                            13

SEQ ID NO: 87           moltype = AA  length = 15
```

-continued

```
FEATURE                 Location/Qualifiers
source                  1..15
                        mol_type = protein
                        organism = Synthetic construct
SEQUENCE: 87
MSGLEQELRR RLTPS                                                    15

SEQ ID NO: 88           moltype = AA  length = 16
FEATURE                 Location/Qualifiers
source                  1..16
                        mol_type = protein
                        organism = Synthetic construct
SEQUENCE: 88
MSGRLEEELR RRLSPS                                                   16

SEQ ID NO: 89           moltype = AA  length = 16
FEATURE                 Location/Qualifiers
source                  1..16
                        mol_type = protein
                        organism = Synthetic construct
SEQUENCE: 89
SPSAVEEELR RRLSPS                                                   16

SEQ ID NO: 90           moltype = AA  length = 14
FEATURE                 Location/Qualifiers
source                  1..14
                        mol_type = protein
                        organism = Synthetic construct
SEQUENCE: 90
GPSAVEEELR RRLS                                                     14

SEQ ID NO: 91           moltype = AA  length = 16
FEATURE                 Location/Qualifiers
source                  1..16
                        mol_type = protein
                        organism = Synthetic construct
SEQUENCE: 91
MPSGLEQELR RRLTPS                                                   16

SEQ ID NO: 92           moltype = AA  length = 16
FEATURE                 Location/Qualifiers
source                  1..16
                        mol_type = protein
                        organism = Synthetic construct
SEQUENCE: 92
MSSGLEQELR RRLTPS                                                   16

SEQ ID NO: 93           moltype = AA  length = 17
FEATURE                 Location/Qualifiers
source                  1..17
                        mol_type = protein
                        organism = Synthetic construct
SEQUENCE: 93
MPSGRLEEEL RRRLSPS                                                  17

SEQ ID NO: 94           moltype = AA  length = 13
FEATURE                 Location/Qualifiers
source                  1..13
                        mol_type = protein
                        organism = Synthetic construct
SEQUENCE: 94
GVTISALNAM AMG                                                      13

SEQ ID NO: 95           moltype = AA  length = 7
FEATURE                 Location/Qualifiers
source                  1..7
                        mol_type = protein
                        organism = Synthetic construct
SEQUENCE: 95
VSERGNA                                                             7

SEQ ID NO: 96           moltype = AA  length = 7
FEATURE                 Location/Qualifiers
source                  1..7
                        mol_type = protein
                        organism = Synthetic construct
SEQUENCE: 96
VSERGNT                                                             7
```

-continued

```
SEQ ID NO: 97           moltype = AA  length = 7
FEATURE                 Location/Qualifiers
source                  1..7
                        mol_type = protein
                        organism = Synthetic construct
SITE                    7
                        note = X is A or T
SEQUENCE: 97
VSERGNX                                                      7

SEQ ID NO: 98           moltype = AA  length = 13
FEATURE                 Location/Qualifiers
source                  1..13
                        mol_type = protein
                        organism = Synthetic construct
SEQUENCE: 98
HVLEDRVDSF HDY                                               13

SEQ ID NO: 99           moltype = AA  length = 25
FEATURE                 Location/Qualifiers
source                  1..25
                        mol_type = protein
                        organism = Synthetic construct
SEQUENCE: 99
EVQLVESGGG LVQPGGSLRL SCAAS                                  25

SEQ ID NO: 100          moltype = AA  length = 15
FEATURE                 Location/Qualifiers
source                  1..15
                        mol_type = protein
                        organism = Synthetic construct
SEQUENCE: 100
WFRQAPGKRR EMVAA                                             15

SEQ ID NO: 101          moltype = AA  length = 15
FEATURE                 Location/Qualifiers
source                  1..15
                        mol_type = protein
                        organism = Synthetic construct
SEQUENCE: 101
WYRQAPGKRR EMVAA                                             15

SEQ ID NO: 102          moltype = AA  length = 15
FEATURE                 Location/Qualifiers
source                  1..15
                        mol_type = protein
                        organism = Synthetic construct
SITE                    2
                        note = X is F or Y
SEQUENCE: 102
WXRQAPGKRR EMVAA                                             15

SEQ ID NO: 103          moltype = AA  length = 38
FEATURE                 Location/Qualifiers
source                  1..38
                        mol_type = protein
                        organism = Synthetic construct
SEQUENCE: 103
MYRESVQGRF TISRDNAKRM VYLQMNSLRA EDTAVYYC                    38

SEQ ID NO: 104          moltype = AA  length = 38
FEATURE                 Location/Qualifiers
source                  1..38
                        mol_type = protein
                        organism = Synthetic construct
SEQUENCE: 104
MYRESVKGRF TISRDNAKRM VYLQMNSLRA EDTAVYYC                    38

SEQ ID NO: 105          moltype = AA  length = 38
FEATURE                 Location/Qualifiers
source                  1..38
                        mol_type = protein
                        organism = Synthetic construct
SEQUENCE: 105
YYRDSVKGRF TISRDNAKRM VYLQMNSLRA EDTAVYYC                    38

SEQ ID NO: 106          moltype = AA  length = 38
FEATURE                 Location/Qualifiers
source                  1..38
```

```
                        mol_type = protein
                        organism = Synthetic construct
SEQUENCE: 106
MYRESVKGRF TISRDNSKNT LYLQMNSLRA EDTAVYYC                           38

SEQ ID NO: 107          moltype = AA  length = 38
FEATURE                 Location/Qualifiers
source                  1..38
                        mol_type = protein
                        organism = Synthetic construct
SEQUENCE: 107
YYRDSVKGRF TISRDNSKNT LYLQMNSLRA EDTAVYYC                           38

SEQ ID NO: 108          moltype = AA  length = 38
FEATURE                 Location/Qualifiers
source                  1..38
                        mol_type = protein
                        organism = Synthetic construct
SITE                    1
                        note = X is M or Y
SITE                    4
                        note = X is D or E
SITE                    7
                        note = X is Q or K
SITE                    17
                        note = X is A or S
SITE                    19
                        note = X is N or R
SITE                    20
                        note = X is M or T
SITE                    21
                        note = X is V or L
SEQUENCE: 108
XYRXSVXGRF TISRDNXKXX XYLQMNSLRA EDTAVYYC                           38

SEQ ID NO: 109          moltype = AA  length = 11
FEATURE                 Location/Qualifiers
source                  1..11
                        mol_type = protein
                        organism = Synthetic construct
SEQUENCE: 109
WGQGTQVTVS S                                                        11

SEQ ID NO: 110          moltype = AA  length = 98
FEATURE                 Location/Qualifiers
source                  1..98
                        mol_type = protein
                        organism = Homo sapiens
SEQUENCE: 110
EVQLVESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAK                           98

SEQ ID NO: 111          moltype = AA  length = 122
FEATURE                 Location/Qualifiers
source                  1..122
                        mol_type = protein
                        organism = Synthetic construct
SEQUENCE: 111
EVQLLESGGG LVQPGGSLRL SCAASGVTIS ALNAMAMGWY RQAPGKRREM VSAVSERGNA  60
MYRESVQGRF TISRDNSKNT LYLQMNSLRA EDTAVYYCAK LEDRVDSFHD YWGQGTLVTV  120
SS                                                                  122

SEQ ID NO: 112          moltype = AA  length = 122
FEATURE                 Location/Qualifiers
source                  1..122
                        mol_type = protein
                        organism = Synthetic construct
SEQUENCE: 112
EVQLLESGGG LVQPGGSLRL SCAASGVTIS ALNAMAMGWF RQAPGKEREG VSAVSERGNA  60
MYRESVQGRF TISRDNSKNT LYLQMNSLRA EDTAVYYCAK LEDRVDSFHD YWGQGTLVTV  120
SS                                                                  122

SEQ ID NO: 113          moltype = AA  length = 122
FEATURE                 Location/Qualifiers
source                  1..122
                        mol_type = protein
                        organism = Synthetic construct
SEQUENCE: 113
EVQLLESGGG LVQPGGSLRL SCAASGVTIS ALNAMAMGWF RQAPGKGLEF VAAVSERGNA  60
```

```
MYRESVQGRF TISRDNSKNT LYLQMNSLRA EDTAVYYCAA LEDRVDSFHD YWGQGTLVTV  120
SS                                                                122

SEQ ID NO: 114          moltype = AA  length = 122
FEATURE                 Location/Qualifiers
source                  1..122
                        mol_type = protein
                        organism = Synthetic construct
SEQUENCE: 114
EVQLLESGGG LVQPGGSLRL SCAASGVTIS ALNAMAMGWF RQAPGKGLEF VAAVSERGNA  60
YYRDSVKGRF TISRDNSKNT LYLQMNSLRA EDTAVYYCAA LEDRVDSFHD YWGQGTLVTV  120
SS                                                                122

SEQ ID NO: 115          moltype = AA  length = 122
FEATURE                 Location/Qualifiers
source                  1..122
                        mol_type = protein
                        organism = Synthetic construct
SEQUENCE: 115
EVQLQASGGG FVQPGGSLRL SCAASGVTIS ALNAMAMGWF RQAPGKEREF VSAISERGNA  60
YYRDSVKGRF TISRDNSKNT VYLQMNSLRA EDTATYYCAA LEDRVDSFHD YWGQGTQVTV  120
SS                                                                122

SEQ ID NO: 116          moltype = AA  length = 122
FEATURE                 Location/Qualifiers
source                  1..122
                        mol_type = protein
                        organism = Synthetic construct
SEQUENCE: 116
EVQLQASGGG FVQPGGSLRL SCAASGVTIS ALNAMAMGWF RQAPGKEREF VSAVSERGNA  60
MYRESVQGRF TISRDNSKNT VYLQMNSLRA EDTATYYCAA LEDRVDSFHD YWGQGTQVTV  120
SS                                                                122

SEQ ID NO: 117          moltype = AA  length = 122
FEATURE                 Location/Qualifiers
source                  1..122
                        mol_type = protein
                        organism = Synthetic construct
SEQUENCE: 117
EVQLVESGGG LVQPGGSLRL SCAASGVTIS ALNAMAMGWF RQAPGKGREL VAAVSERGNA  60
MYRESVQGRF TISRDNAKRM VYLQMNSLRA EDTAVYYCHV LEDRVDSFHD YWGQGTQVTV  120
SS                                                                122

SEQ ID NO: 118          moltype = AA  length = 122
FEATURE                 Location/Qualifiers
source                  1..122
                        mol_type = protein
                        organism = Synthetic construct
SEQUENCE: 118
EVQLVESGGG LVQPGGSLRL SCAASGVTIS ALNAMAMGWF RQAPGKRREM VAAVSERGNA  60
MYRESVQGRF TISRDNAKRM VYLQMNSLRA EDTAVYYCHV LEDRVDSFHD YWGQGTQVTV  120
SS                                                                122

SEQ ID NO: 119          moltype = AA  length = 122
FEATURE                 Location/Qualifiers
source                  1..122
                        mol_type = protein
                        organism = Synthetic construct
SEQUENCE: 119
EVQLVESGGG LVQPGGSLRL SCAASGVTIS ALNAMAMGWY RQAPGKRREM VAAVSERGNA  60
MYRESVQGRF TISRDNAKRM VYLQMNSLRA EDTAVYYCHV LEDRVDSFHD YWGQGTQVTV  120
SS                                                                122

SEQ ID NO: 120          moltype = AA  length = 122
FEATURE                 Location/Qualifiers
source                  1..122
                        mol_type = protein
                        organism = Synthetic construct
SEQUENCE: 120
EVQLVESGGG LVQPGGSLRL SCAASGVTIS ALNAMAMGWY RQAPGKRREM VAAVSERGNT  60
MYRESVQGRF TISRDNAKRM VYLQMNSLRA EDTAVYYCHV LEDRVDSFHD YWGQGTQVTV  120
SS                                                                122

SEQ ID NO: 121          moltype = AA  length = 122
FEATURE                 Location/Qualifiers
source                  1..122
                        mol_type = protein
                        organism = Synthetic construct
SEQUENCE: 121
```

-continued

```
EVQLVESGGG LVQPGGSLRL SCAASGVTIS ALNAMAMGWY RQAPGKRREM VAAVSERGNA  60
MYRESVKGRF TISRDNAKRM VYLQMNSLRA EDTAVYYCHV LEDRVDSFHD YWGQGTQVTV  120
SS                                                                122

SEQ ID NO: 122          moltype = AA  length = 122
FEATURE                 Location/Qualifiers
source                  1..122
                        mol_type = protein
                        organism = Synthetic construct
SEQUENCE: 122
EVQLVESGGG LVQPGGSLRL SCAASGVTIS ALNAMAMGWY RQAPGKRREM VAAVSERGNT  60
MYRESVKGRF TISRDNAKRM VYLQMNSLRA EDTAVYYCHV LEDRVDSFHD YWGQGTQVTV  120
SS                                                                122

SEQ ID NO: 123          moltype = AA  length = 122
FEATURE                 Location/Qualifiers
source                  1..122
                        mol_type = protein
                        organism = Synthetic construct
SEQUENCE: 123
EVQLVESGGG LVQPGGSLRL SCAASGVTIS ALNAMAMGWY RQAPGKRREM VAAVSERGNT  60
YYRDSVKGRF TISRDNAKRM VYLQMNSLRA EDTAVYYCHV LEDRVDSFHD YWGQGTQVTV  120
SS                                                                122

SEQ ID NO: 124          moltype = AA  length = 122
FEATURE                 Location/Qualifiers
source                  1..122
                        mol_type = protein
                        organism = Synthetic construct
SEQUENCE: 124
EVQLVESGGG LVQPGGSLRL SCAASGVTIS ALNAMAMGWY RQAPGKRREM VAAVSERGNA  60
MYRESVKGRF TISRDNSKNT LYLQMNSLRA EDTAVYYCHV LEDRVDSFHD YWGQGTQVTV  120
SS                                                                122

SEQ ID NO: 125          moltype = AA  length = 122
FEATURE                 Location/Qualifiers
source                  1..122
                        mol_type = protein
                        organism = Synthetic construct
SEQUENCE: 125
EVQLVESGGG LVQPGGSLRL SCAASGVTIS ALNAMAMGWY RQAPGKRREM VAAVSERGNT  60
YYRDSVKGRF TISRDNSKNT LYLQMNSLRA EDTAVYYCHV LEDRVDSFHD YWGQGTQVTV  120
SS                                                                122

SEQ ID NO: 126          moltype = AA  length = 11
FEATURE                 Location/Qualifiers
source                  1..11
                        mol_type = protein
                        organism = Homo sapiens
SEQUENCE: 126
WGQGTTVTVS S                                                      11

SEQ ID NO: 127          moltype = AA  length = 11
FEATURE                 Location/Qualifiers
source                  1..11
                        mol_type = protein
                        organism = Synthetic construct
SEQUENCE: 127
GVTISALNAM A                                                      11

SEQ ID NO: 128          moltype = AA  length = 8
FEATURE                 Location/Qualifiers
source                  1..8
                        mol_type = protein
                        organism = Synthetic construct
SEQUENCE: 128
ALNAMAMG                                                          8

SEQ ID NO: 129          moltype = AA  length = 130
FEATURE                 Location/Qualifiers
source                  1..130
                        mol_type = protein
                        organism = Synthetic construct
SEQUENCE: 129
EVQLQESGGG LVQAGGSLRL SCTASGVTIS ALNAMAMGWY RQAPGKRRVM VAAVSERGNT  60
MYRESVKGRF TVSRDFTNKT VYLQMNSLKP EDTAVYYCHV LEDRVDSFHD YWGQGTQVTV  120
SSLEHHHHHH                                                        130
```